United States Patent
Ballell Pages et al.

(10) Patent No.: US 8,524,750 B2
(45) Date of Patent: Sep. 3, 2013

(54) (PYRAZOL-3-YL)-1,3,4-THIADIAZOL-2-AMINE AND (PYRAZOL-3-YL)-1,3,4-THIAZOL-2-AMINE COMPOUNDS

(75) Inventors: Lluis Ballell Pages, Madrid (ES); Julia Castro Pichel, Madrid (ES); Raquel Fernandez Menendez, Madrid (ES); Esther Pilar Fernandez Velando, Madrid (ES); Silvia Gonzalez Del Valle, Madrid (ES); Maria Luisa Leon Diaz, Madrid (ES); Alfonso Mendoza Losana, Madrid (ES); Matthew James Wolfendale, Middlesex (GB)

(73) Assignee: Glaxo Group Limited, Brentford, Middlesex (GB)

( * ) Notice: Subject to any disclaimer, the term of this patent is extended or adjusted under 35 U.S.C. 154(b) by 34 days.

(21) Appl. No.: 13/264,169

(22) PCT Filed: Apr. 13, 2010

(86) PCT No.: PCT/EP2010/002265
§ 371 (c)(1),
(2), (4) Date: Oct. 13, 2011

(87) PCT Pub. No.: WO2010/118852
PCT Pub. Date: Oct. 21, 2010

(65) Prior Publication Data
US 2012/0095064 A1 Apr. 19, 2012

(30) Foreign Application Priority Data
Apr. 13, 2009 (EP) ..................... 09382049

(51) Int. Cl.
A61K 31/433 (2006.01)
A61K 31/427 (2006.01)
A61K 31/4155 (2006.01)
C07D 285/135 (2006.01)
C07D 231/16 (2006.01)
C07D 417/14 (2006.01)

(52) U.S. Cl.
USPC ........ 514/363; 514/406; 514/370; 548/364.1; 548/138; 548/190

(58) Field of Classification Search
USPC .............. 514/406, 363, 370; 548/364.1, 138, 548/190
See application file for complete search history.

(56) References Cited
PUBLICATIONS

Wang et al., Journal of Chromotography B, (2008), vol. 862, p. 1-14.*
Ballell, et al., New Small-Molecule Synthetic Anti Mycobacterials, Antimicrobial Agents and Chemotherapy, American Society for Microbiology, Washington, DC, 49(6):2153-2163 (2005).

* cited by examiner

Primary Examiner — Yong Chu
(74) Attorney, Agent, or Firm — Bonnie L. Deppenbrock

(57) ABSTRACT

A compound of Formula (I)

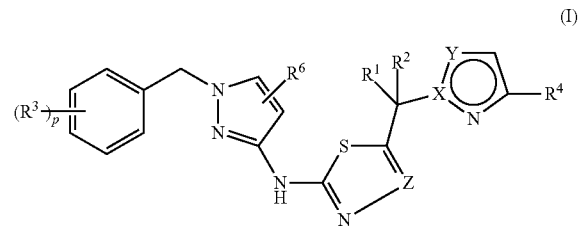

wherein: either X is N and Y is $CR^5$ or X is C and Y is S; Z is selected from N and CH; $R^1$ is selected from H and Me; $R^2$ is selected from H, OH, OMe and Me; each $R^3$ is independently selected from $C_{1-3}$alkyl, F, Cl, Br, $CF_3$ and $NH_2$; $R^4$ is selected from Me, $CF_3$, $NO_2$ and $CHF_2$; $R^5$ is selected from H, Me and $CHF_2$; $R^6$ is selected from H and Me; and p is 0-3, compositions containing them, their use in therapy, for example in the treatment of tuberculosis, and methods for the preparation of such compounds, are provided.

21 Claims, No Drawings

(PYRAZOL-3-YL)-1,3,4-THIADIAZOL-2-AMINE AND (PYRAZOL-3-YL)-1,3,4-THIAZOL-2-AMINE COMPOUNDS

This application is filed pursuant to 35 U.S.C. §371 as a United States National Phase Application of International Patent Application Serial No. PCT/2010/002265 filed Apr. 13, 2010, which claims priority to European Application No. EP 09382049.6 filed Apr. 13, 2009, the contents of which are incorporated herein by reference.

FIELD OF THE INVENTION

This invention relates to compounds, compositions containing them, their use in therapy, for example in the treatment of tuberculosis, and methods for the preparation of such compounds.

BACKGROUND OF THE INVENTION

Synthetic drugs for treating tuberculosis (TB) have been available for over half a century, but incidences of the disease continue to rise world-wide. In 2004, it is estimated that 24,500 people developed active disease and close to 5,500 died each day from TB (World Health Organization, Global Tuberculosis Control: Surveillance, Planning, Financing. WHO Report 2006, Geneva, Switzerland, ISBN 92-4 156314-1). Co-infection with HIV is driving the increase in incidence (Williams, B. G.; Dye, C. *Science,* 2003, 301, 1535) and the cause of death in 31% of AIDS patients in Africa can be attributed to TB (Corbett, E. L.; Watt, C. J.; Catherine, J.; Walker, N.; Maher D.; Williams, B. G.; Raviglione, M. C.; Dye, C. *Arch. Intl. Med.,* 2003, 163, 1009, Septkowitz, A.; Raffalli, J.; Riley, T.; Kiehn, T. E.; Armstrong, D. *Clin. Microbiol. Rev.* 1995, 8, 180). When coupled with the emergence of multi-drug resistant strains of *Mycobacterium tuberculosis* (MDR-TB), the scale of the problem is amplified. It is now more than a decade since the WHO declared TB "a global health emergency" (World Health Organization, Global Tuberculosis Control: Surveillance, Planning, Financing. WHO Report 2006, Geneva, Switzerland, ISBN 92-4 156314-1).

The limitations of tuberculosis therapy and prevention are well-known. The current available vaccine, BCG was introduced in 1921 and fails to protect most people past childhood. Patients who do become infected with active disease currently endure combination therapy with isoniazid (INH), rifampin, pyrazinamide and ethambutol for two months and then continue taking isoniazid and rifampin for a further four months. Daily dosing is required and poor compliance drives the emergence and spread of multi-drug-resistant strains, which are challenging to treat. A recently-published detailed review discusses many aspects of TB such as pathogenesis, epidemiology, drug discovery and vaccine development to date (Nature Medicine, Vol 13(3), pages 263-312).

Shorter courses of more active agents which can be taken less frequently and which present a high barrier to the emergence of resistance, i.e. agents which are effective against multi-drug resistant strains of TB, are urgently required. There is therefore a need to discover and develop new chemical entities to treat TB. Recent synthetic leads are reviewed in: Ballell, L.; Field, R. A.; Duncan, K.; Young, R. J. *Antimicrob. Agents Chemother.* 2005, 49, 2153.

Lipid metabolism is especially important for the genus *Mycobacterium* and it represents a well-validated target for the development of selective antitubercular agents. The enzyme which is denoted "InhA" is an NADH-dependent (dependent on the reduced form of nicotinamide adenine dinucleotide), 2-trans enoyl-ACP (acyl carrier protein) reductase of the type 2 fatty acid synthesis (FASII) pathway in *Mycobacterium tuberculosis*. There is a strong body of evidence indicating that InhA is the primary target of the frontline antitubercular drug isoniazid (INH). Clinical isolates as well as laboratory modified mycobacteria over-expressing InhA show resistance to INH. The drug inhibits InhA enzymatic activity inducing an accumulation of saturated C24-C26 fatty acids and blocking the production of longer molecules, including mycolic acids. This inhibition correlates with mycobacterial cell death.

The essentiality of InhA has also been demonstrated by the use of temperature-sensitive mutants of InhA in *Mycobacterium smegmatis*, where a shift to the non-permissive temperature results in rapid lysis and cell death.

INH is a bactericidal drug, showing specific activity against *Mycobacterium tuberculosis*, and is part of the first-line drug combination regimen for antitubercular therapy. INH is activated within the mycobacterial cell by the KatG catalase. The activated form is thought to react covalently with NADH within the InhA active site to form an inhibitory adduct. X-Ray structures of InhA bound to several inhibitors are available and are being used to design new inhibitors.

In vitro-activated INH forms adducts with NAD(P) cofactors which bind to and inhibit InhA and other enzymes like DHFR (dehydrofolate reductase); the physiological relevance of these interactions in vivo is clear in the case of the enoyl-reductase, but it has been shown to be almost irrelevant in the case of DHFR; the potential role of other possible targets of INH in the antitubercular activity of the drug seems minimal or non-existent.

Resistance to INH has been associated with at least five different genes (KatG, InhA, ahpC, kasA, and ndh); 60-70% of resistant isolates can be directly linked to defects in the KatG gene (often with compensatory mutations in other genes) and less commonly in the InhA structural gene and upstream promoter region.

It is anticipated that a drug targeted at InhA, not requiring activation by KatG, would interact with the enzyme in a different way from the complex NAD-INH, would also have a different pharmacological profile from INH, would kill the majority of the current INH$^R$ (isoniazid-resistant) strains and would replace INH in the existing therapy against *Mycobacterium tuberculosis*.

DETAILED DESCRIPTION OF THE INVENTION

The present invention provides a compound of Formula (I) or a pharmaceutically acceptable salt thereof:

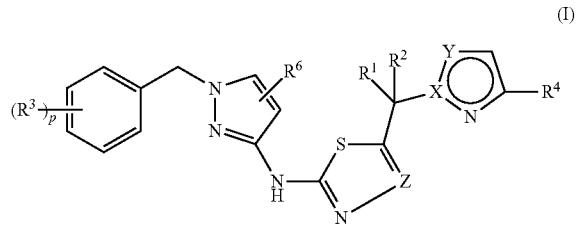

(I)

wherein:
either X is N and Y is CR$^5$; or X is C and Y is S;
Z is selected from N and CH;

$R^1$ is selected from H and Me, $R^2$ is selected from H, OH, OMe and Me;

each $R^3$ is independently selected from $C_{1-3}$alkyl, F, Cl, Br, $CF_3$ and $NH_2$;

$R^4$ is selected from Me, $CF_3$, $NO_2$ and $CHF_2$;

$R^5$ is selected from H, Me and $CHF_2$;

$R^6$ is selected from H and Me; and p is 0-3.

In one aspect of the invention there is provided a compound of Formula (I) as defined hereinabove.

The invention further provides a pharmaceutical composition comprising a compound of Formula (I), or a pharmaceutically acceptable salt thereof, and one or more pharmaceutically acceptable carriers, excipients or diluents.

In one aspect of the invention there is provided a pharmaceutical composition comprising a compound of Formula (I) and one or more pharmaceutically acceptable carriers, excipients or diluents.

The invention also provides a method of treatment of tuberculosis in mammals, particularly in man, which method comprises the administration to a mammal in need of such treatment an effective amount of a compound of Formula (I), or a pharmaceutically acceptable salt thereof.

In one aspect of the invention there is provided a method of treatment of tuberculosis in mammals, particularly in man, which method comprises the administration to a mammal in need of such treatment an effective amount of a compound of Formula (I).

The invention further provides a compound of Formula (I), or a pharmaceutically acceptable salt thereof, for use in therapy.

In one aspect of the invention there is provided a compound of Formula (I) for use in therapy The invention yet further provides a compound of Formula (I), or a pharmaceutically acceptable salt thereof, for use in the treatment of tuberculosis in mammals, particularly in man.

In one aspect of the invention there is provided a compound of Formula (I) for use in the treatment of tuberculosis in mammals, particularly in man.

The invention still further provides the use of a compound of Formula (I), or a pharmaceutically acceptable salt thereof, in the manufacture of a medicament for use in the treatment of tuberculosis in mammals, particularly in man.

In one aspect of the invention there is provided the use of a compound of Formula (I) in the manufacture of a medicament for use in the treatment of tuberculosis in mammals, particularly in man.

The invention also provides a pharmaceutical composition comprising a compound of Formula (I), or a pharmaceutically acceptable salt thereof, and one or more pharmaceutically acceptable carriers, excipients or diluents, for use in the treatment of tuberculosis in mammals, particularly in man.

In one aspect of the invention there is provided a pharmaceutical composition comprising a compound of Formula (I) and one or more pharmaceutically acceptable carriers, excipients or diluents, for use in the treatment of tuberculosis in mammals, particularly in man.

In one aspect of the invention, the absolute stereochemistry of the compound of Formula (I), or a pharmaceutically acceptable salt thereof, is as shown in Formula (I*):

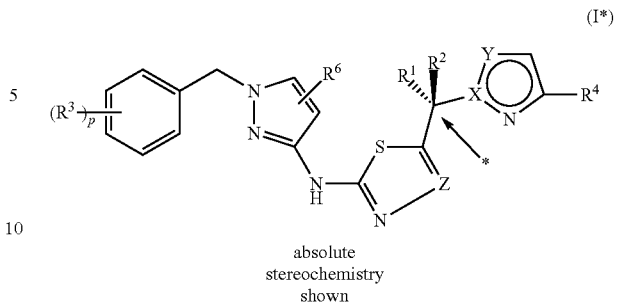

absolute stereochemistry shown

In one aspect of the invention, $R^2$ is selected from H, OH and Me.

In one aspect of the invention, when X is N and Y is $CR^5$, $R^2$ is selected from H and Me.

In one aspect of the invention, X is C and Y is S.

In one aspect of the invention, $R^1$ is Me. In a further aspect of the invention, $R^1$ is Me and $R^2$ is H, OH or OMe. In a yet further aspect, $R^1$ is Me and $R^2$ is OH. In embodiments of the invention in which $R^1$ is Me and $R^2$ is H, OH or OMe, the carbon atom to which groups $R^1$ and $R^2$ are bonded (labelled "*" in Formula (I*) above) is a stereogenic centre. Such embodiments may be in the form of a mixture of isomers, for example a racemic mixture of enantiomers, or a single isomer. In one embodiment, the invention provides a single isomer of a compound of the invention wherein $R^1$ is Me and $R^2$ is H, OH or OMe. In another embodiment, the invention provides a single isomer of a compound of the invention wherein $R^1$ is Me and $R^2$ is OH. In a further embodiment, the invention provides a compound of Formula (I) or a pharmaceutically acceptable salt thereof having the absolute chemistry shown in Formula (I*), wherein $R^1$ is Me and $R^2$ is H, OH or OMe. In a yet further embodiment, the invention provides a compound of Formula (I) or a pharmaceutically acceptable salt thereof having the absolute chemistry shown in Formula (I*), wherein $R^1$ is Me and $R^2$ is OH.

In one aspect, the invention provides compounds of the Formula (I) or pharmaceutically acceptable salts thereof in which the stereogenic centre marked * in Formula (I-S) below is in the (S)-configuration:

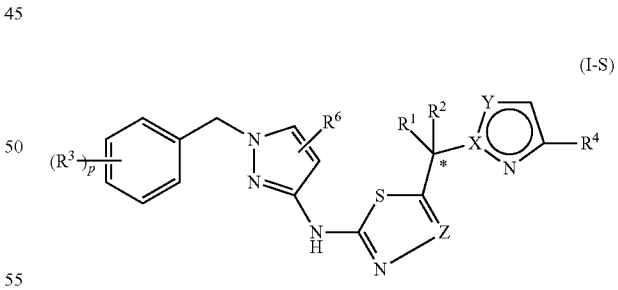

In one aspect, compounds which are useful in the present invention include those mentioned in the Examples and their pharmaceutically acceptable salts.

In one aspect of the invention, at least one $R^3$ group is selected from $C_{1-3}$alkyl, $CF_3$ and $NH_2$. In one embodiment p is 1 and $R^3$ is selected from $C_{1-3}$alkyl, $CF_3$ and $NH_2$. In a further embodiment, p is 2, one $R^3$ group is selected from $C_{1-3}$alkyl, $CF_3$ and $NH_2$ and the other $R^3$ group is selected from $C_{1-3}$alkyl, F, Cl, Br, $CF_3$ and $NH_2$. In a yet further embodiment, p is 3, one $R^3$ group is selected from $C_{1-3}$alkyl, $CF_3$ and $NH_2$ and the other two $R^3$ groups are selected from $C_{1-3}$alkyl, F, Cl, Br, $CF_3$ and $NH_2$. In a further aspect of the invention at least two $R^3$ groups are F. In one embodiment, p is 2 and both $R^3$ groups are F. In a further embodiment, p is 3, two $R^3$ groups are F and the remaining $R^3$ group is selected from $C_{1-3}$alkyl, F, Cl, Br, $CF_3$ and $NH_2$. For example, two $R^3$ groups are F and the remaining $R^3$ group is Me.

In another aspect, compounds which are useful in the present invention include:

1. 5-[1-(3,5-dimethyl-1H-pyrazol-1-yl)ethyl]-N-(1-{[2-(trifluoromethyl)phenyl]methyl}-1H-pyrazol-3-yl)-1,3,4-thiadiazol-2-amine
2. N-{1-[(2,5-dichlorophenyl)methyl]-1H-pyrazol-3-yl}-5-[1-(3,5-dimethyl-1H-pyrazol-1-yl)ethyl]-1,3,4-thiadiazol-2-amine
3. N-{1-[(2-bromophenyl)methyl]-1H-pyrazol-3-yl}-5-[1-(3,5-dimethyl-1H-pyrazol-1-yl)ethyl]-1,3,4-thiadiazol-2-amine
4. N-{1-[(2,5-dichlorophenyl)methyl]-1H-pyrazol-3-yl}-5-[1-(3-methyl-1H-pyrazol-1-yl)ethyl]-1,3,4-thiadiazol-2-amine
5. N-{1-[(2-bromophenyl)methyl]-1H-pyrazol-3-yl}-5-[1-(3-methyl-1H-pyrazol-1-yl)ethyl]-1,3,4-thiadiazol-2-amine
6. 5-[1-(3,5-dimethyl-1H-pyrazol-1-yl)ethyl]-N-{1-[(2-fluorophenyl)methyl]-1H-pyrazol-3-yl}-1,3,4-thiadiazol-2-amine
7. N-{1-[(3-chloro-2-fluorophenyl)methyl]-1H-pyrazol-3-yl}-5-[1-(3,5-dimethyl-1H-pyrazol-1-yl)ethyl]-1,3,4-thiadiazol-2-amine
8. N-(1-{[2,5-bis(trifluoromethyl)phenyl]methyl}-1H-pyrazol-3-yl)-5-[1-(3,5-dimethyl-1H-pyrazol-1-yl)ethyl]-1,3,4-thiadiazol-2-amine
9. 5-[1-(3,5-dimethyl-1H-pyrazol-1-yl)ethyl]-N-(1-{[5-fluoro-2-(trifluoromethyl)phenyl]methyl}-1H-pyrazol-3-yl)-1,3,4-thiadiazol-2-amine
10. N-{1-[(2,3-difluorophenyl)methyl]-1H-pyrazol-3-yl}-5-[1-(3,5-dimethyl-1H-pyrazol-1-yl)ethyl]-1,3,4-thiadiazol-2-amine
11. N-(1-{[2-chloro-5-(trifluoromethyl)phenyl]methyl}-1H-pyrazol-3-yl)-5-[1-(3,5-dimethyl-1H-pyrazol-1-yl)ethyl]-1,3,4-thiadiazol-2-amine
12. N-{1-[(2,6-difluorophenyl)methyl]-1H-pyrazol-3-yl}-5-[1-(3,5-dimethyl-1H-pyrazol-1-yl)ethyl]-1,3,4-thiadiazol-2-amine
13. N-{1-[(2-fluoro-3-methylphenyl)methyl]-1H-pyrazol-3-yl}-5-[1-(3-methyl-1H-pyrazol-1-yl)ethyl]-1,3,4-thiadiazol-2-amine
14. N-{1-[(3-chloro-2-fluorophenyl)methyl]-1H-pyrazol-3-yl}-5-[1-(3-methyl-1H-pyrazol-1-yl)ethyl]-1,3,4-thiadiazol-2-amine
15. N-{1-[(2,3-difluorophenyl)methyl]-1H-pyrazol-3-yl}-5-[1-(3-methyl-1H-pyrazol-1-yl)ethyl]-1,3,4-thiadiazol-2-amine
16. N-{1-[(2,3-difluorophenyl)methyl]-1H-pyrazol-3-yl}-5-[1-(4-methyl-1,3-thiazol-2-yl)ethyl]-1,3,4-thiadiazol-2-amine
17. N-{1-[(2-chloro-4-fluorophenyl)methyl]-1H-pyrazol-3-yl}-5-[1-(3,5-dimethyl-1H-pyrazol-1-yl)ethyl]-1,3,4-thiadiazol-2-amine
18. N-{1-[(2-chloro-4-fluorophenyl)methyl]-1H-pyrazol-3-yl}-5-[1-(3-methyl-1H-pyrazol-1-yl)ethyl]-1,3,4-thiadiazol-2-amine
19. N-{1-[(2-chloro-6-fluorophenyl)methyl]-5-methyl-1H-pyrazol-3-yl}-5-[1-(3,5-dimethyl-1H-pyrazol-1-yl)ethyl]-1,3,4-thiadiazol-2-amine
20. 5-[1-(3,5-dimethyl-1H-pyrazol-1-yl)ethyl]-N-{1-[(2-methylphenyl)methyl]-1H-pyrazol-3-yl}-1,3,4-thiadiazol-2-amine
21. 5-[1-(3,5-dimethyl-1H-pyrazol-1-yl)ethyl]-N-[1-(phenylmethyl)-1H-pyrazol-3-yl]-1,3,4-thiadiazol-2-amine
22. N-{1-[(6-chloro-2-fluoro-3-methylphenyl)methyl]-1H-pyrazol-3-yl}-5-[1-(3,5-dimethyl-1H-pyrazol-1-yl)ethyl]-1,3,4-thiadiazol-2-amine
23. N-{1-[(2-chloro-6-fluoro-3-methylphenyl)methyl]-1H-pyrazol-3-yl}-5-[1-(3,5-dimethyl-1H-pyrazol-1-yl)ethyl]-1,3,4-thiadiazol-2-amine
24. 5-[1-(3,5-dimethyl-1H-pyrazol-1-yl)ethyl]-N-{1-[(2-fluoro-3-methylphenyl)methyl]-1H-pyrazol-3-yl}-1,3,4-thiadiazol-2-amine
25. N-{1-[(2-fluoro-3-methylphenyl)methyl]-1H-pyrazol-3-yl}-5-[1-(4-methyl-1,3-thiazol-2-yl)ethyl]-1,3,4-thiadiazol-2-amine
26. N-{1-[(5-amino-2-chlorophenyl)methyl]-1H-pyrazol-3-yl}-5-[1-(3,5-dimethyl-1H-pyrazol-1-yl)ethyl]-1,3,4-thiadiazol-2-amine
27. N-{1-[(3-amino-2-methylphenyl)methyl]-1H-pyrazol-3-yl}-5-[1-(3,5-dimethyl-1H-pyrazol-1-yl)ethyl]-1,3,4-thiadiazol-2-amine
28. N-{1-[(2-chloro-6-fluorophenyl)methyl]-1H-pyrazol-3-yl}-5-[1-(3,5-dimethyl-1H-pyrazol-1-yl)ethyl]-1,3,4-thiadiazol-2-amine
29. N-{1-[(2-chloro-6-fluorophenyl)methyl]-1H-pyrazol-3-yl}-5-[1-(4-methyl-1,3-thiazol-2-yl)ethyl]-1,3,4-thiadiazol-2-amine
30. 1-[5-({1-[(2-chloro-6-fluorophenyl)methyl]-1H-pyrazol-3-yl}amino)-1,3,4-thiadiazol-2-yl]-1-(4-methyl-1,3-thiazol-2-yl)ethanol
31. N-{1-[(2-chloro-6-fluorophenyl)methyl]-1H-pyrazol-3-yl}-5-{1-[4-(trifluoromethyl)-1,3-thiazol-2-yl]ethyl}-1,3,4-thiadiazol-2-amine
32. N-{1-[(2-chloro-6-fluorophenyl)methyl]-1H-pyrazol-3-yl}-5-[(4-methyl-1,3-thiazol-2-yl)methyl]-1,3,4-thiadiazol-2-amine
33. N-{1-[(3-chloro-2-fluorophenyl)methyl]-1H-pyrazol-3-yl}-5-[1-(4-methyl-1,3-thiazol-2-yl)ethyl]-1,3,4-thiadiazol-2-amine
34. N-{1-[(4-chlorophenyl)methyl]-1H-pyrazol-3-yl}-5-[1-(3,5-dimethyl-1H-pyrazol-1-yl)ethyl]-1,3,4-thiadiazol-2-amine
35. 5-[1-(3,5-dimethyl-1H-pyrazol-1-yl)ethyl]-N-(1-{[4-(trifluoromethyl)phenyl]methyl}-1H-pyrazol-3-yl)-1,3,4-thiadiazol-2-amine
36. N-{1-[(2-chloro-5-fluorophenyl)methyl]-1H-pyrazol-3-yl}-5-[1-(3,5-dimethyl-1H-pyrazol-1-yl)ethyl]-1,3,4-thiadiazol-2-amine
37. N-{1-[(2-chloro-6-fluorophenyl)methyl]-1H-pyrazol-3-yl}-5-[(3,5-dimethyl-1H-pyrazol-1-yl)methyl]-1,3-thiazol-2-amine
38. N-{1-[(2-chloro-6-fluorophenyl)methyl]-1H-pyrazol-3-yl}-5-[1-(3-methyl-1H-pyrazol-1-yl)ethyl]-1,3,4-thiadiazol-2-amine
39. N-{1-[(2-chloro-6-fluorophenyl)methyl]-1H-pyrazol-3-yl}-5-[(3-methyl-1H-pyrazol-1-yl)methyl]-1,3,4-thiadiazol-2-amine
40. N-{1-[(2-chlorophenyl)methyl]-1H-pyrazol-3-yl}-5-[1-(5-methyl-3-nitro-1H-pyrazol-1-yl)ethyl]-1,3,4-thiadiazol-2-amine
41. N-{1-[(2-chlorophenyl)methyl]-1H-pyrazol-3-yl}-5-{1-[3-(difluoromethyl)-5-methyl-1H-pyrazol-1-yl]ethyl}-1,3,4-thiadiazol-2-amine 42 N-{1-[(2-chlorophenyl)methyl]-1H-pyrazol-3-yl}-5-[1-(3-methyl-1H-pyrazol-1-yl)ethyl]-1,3,4-thiadiazol-2-amine 43 5-{1-[3-(difluoromethyl)-5-methyl-1H-pyrazol-1-yl]ethyl}-N-[1-(phenylmethyl)-1H-pyrazol-3-yl]-1,3,4-thiadiazol-2-amine 44 5-[1-(3-methyl-1H-pyrazol-1-yl)ethyl]-N-[1-(phenylmethyl)-1H-pyrazol-3-yl]-1,3,4-thiadiazol-2-amine 45 5-{[3-(difluoromethyl)-5-methyl-1H-pyrazol-1-yl]methyl}-N-[1-(phenylmethyl)-1H-pyrazol-3-yl]-1,3,4-thiadiazol-2-amine 46 N-{1-[(2-chlorophenyl)methyl]-1H-pyrazol-3-yl}-5-{[3-(difluoromethyl)-5-methyl-1H-pyrazol-1-yl]methyl}-1,3,4-thiadiazol-2-amine 47 N-{1-[(2,6-dichlorophenyl)methyl]-1H-pyrazol-3-yl}-5-[(3-nitro-1H-pyrazol-1-yl)methyl]-1,3,4-thiadiazol-2-amine 48 N-{1-[(2-chlorophenyl)methyl]-1H-pyrazol-3-yl}-5-{[5-methyl-3-(trifluoromethyl)-1H-pyrazol-1-yl]methyl}-1,3,4-thiadiazol-2-amine 49 N-{1-[(2-chlorophenyl)methyl]-1H-pyrazol-3-yl}-5-[(3-nitro-1H-pyrazol-1-yl)methyl]-1,3,4-thiadiazol-2-amine 50 N-{1-[(2-chloro-6-fluorophenyl)methyl]-1H-pyrazol-3-yl}-5-[(5-methyl-3-nitro-1H-pyrazol-1-yl)methyl]-1,3,4-thiadiazol-2-amine 51 N-{1-[(2-chloro-6-fluorophenyl)methyl]-1H-pyrazol-3-yl}-5-[(3,5-dimethyl-1H-pyrazol-1-yl)methyl]-1,3,4-thiadiazol-2-amine 52 N-{1-[(2-chloro-6-fluorophenyl)methyl]-1H-pyrazol-3-yl}-5-[(3-nitro-1H-pyrazol-1-yl)methyl]-1,3,4-thiadiazol-2-amine 53 N-{1-[(2,6-dichlorophenyl)methyl]-1H-pyrazol-3-yl}-5-[(3,5-dimethyl-1H-pyrazol-1-yl)methyl]-1,3,4-thiadiazol-2-amine 54 N-{1-[(2,6-dichlorophenyl)methyl]-1H-pyrazol-3-yl}-5-[1-(3-methyl-1H-pyrazol-1-yl)ethyl]-1,3,4-thiadiazol-2-amine 55 N-{1-[(2-chloro-6-fluorophenyl)methyl]-1H-pyrazol-3-yl}-5-{[3-(difluoromethyl)-5-methyl-1H-pyrazol-1-yl]methyl}-1,3,4-thiadiazol-2-amine 56 N-{1-[(2-chlorophenyl)methyl]-1H-pyrazol-3-yl}-5-[(3,5-dimethyl-1H-pyrazol-1-yl)methyl]-1,3,4-thiadiazol-2-amine 57 N-{1-[(2,6-dichlorophenyl)methyl]-1H-pyrazol-3-yl}-5-[(3-methyl-1H-pyrazol-1-yl)methyl]-1,3,4-thiadiazol-2-amine 58 N-{1-[(2-chlorophenyl)methyl]-1H-pyrazol-3-yl}-5-[(5-methyl-3-nitro-1H-pyrazol-1-yl)methyl]-1,3,4-thiadiazol-2-amine 59 N-{1-[(2-chlorophenyl)methyl]-1H-pyrazol-3-yl}-5-{[3-(trifluoromethyl)-1H-pyrazol-1-yl]methyl}-1,3,4-thiadiazol-2-amine 60 5-[(3-methyl-1H-pyrazol-1-yl)methyl]-N-[1-(phenylmethyl)-1H-pyrazol-3-yl]-1,3,4-thiadiazol-2-amine 61 N-[1-(phenylmethyl)-1H-pyrazol-3-yl]-5-{[3-(trifluoromethyl)-1H-pyrazol-1-yl]methyl}-1,3,4-thiadiazol-2-amine 62 5-[(5-methyl-3-nitro-1H-pyrazol-1-yl)methyl]-N-[1-(phenylmethyl)-1H-pyrazol-3-yl]-1,3,4-thiadiazol-2-amine 63 N-{1-[(2-chloro-6-fluorophenyl)methyl]-1H-pyrazol-3-yl}-5-{[3-(trifluoromethyl)-1H-pyrazol-1-yl]methyl}-1,3,4-thiadiazol-2-amine 64 5-[(3,5-dimethyl-1H-pyrazol-1-yl)methyl]-N-[1-(phenylmethyl)-1H-pyrazol-3-yl]-1,3,4-thiadiazol-2-amine 65 N-{1-[(2,6-dichlorophenyl)methyl]-1H-pyrazol-3-yl}-5-[1-(5-methyl-3-nitro-1H-pyrazol-1-yl)methyl]-1,3,4-thiadiazol-2-amine 66 N-{1-[(2-chloro-6-fluorophenyl)methyl]-1H-pyrazol-3-yl}-5-[(1R)-1-(3-methyl-1H-pyrazol-1-yl)ethyl]-1,3,4-thiadiazol-2-amine 67 N-{1-[(2-chloro-6-fluorophenyl)methyl]-1H-pyrazol-3-yl}-5-[(1S)-1-(3-methyl-1H-pyrazol-1-yl)ethyl]-1,3,4-thiadiazol-2-amine 68 N-{1-[(2-chloro-6-fluorophenyl)methyl]-1H-pyrazol-3-yl}-5-[(1R)-1-(3,5-dimethyl-1H-pyrazol-1-yl)ethyl]-1,3,4-thiadiazol-2-amine 69 N-{1-[(2-chloro-6-fluorophenyl)methyl]-1H-pyrazol-3-yl}-5-[(1S)-1-(3,5-dimethyl-1H-pyrazol-1-yl)ethyl]-1,3,4-thiadiazol-2-amine 70 (1S)-1-[5-({1-[(2-chloro-6-fluorophenyl)methyl]-1H-pyrazol-3-yl}amino)-1,3,4-thiadiazol-2-yl]-1-(4-methyl-1,3-thiazol-2-yl)ethanol 71 (1R)-1-[5-({1-[(2-chloro-6-fluorophenyl)methyl]-1H-pyrazol-3-yl}amino)-1,3,4-thiadiazol-2-yl]-1-(4-methyl-1,3-thiazol-2-yl)ethanol 72 N-{1-[(2-chloro-6-fluorophenyl)methyl]-1H-pyrazol-3-yl}-5-[1-(methyloxy)-1-(4-methyl-1,3-thiazol-2-yl)ethyl]-1,3,4-thiadiazol-2-amine 73 N-{1-[(2,6-difluorophenyl)methyl]-1H-pyrazol-3-yl}-5-[(methyloxy)(4-methyl-1,3-thiazol-2-yl)methyl]-1,3,4-thiadiazol-2-amine 74 N-{1-[(2-chloro-6-fluorophenyl)methyl]-1H-pyrazol-3-yl}-5-[1-methyl-1-(4-methyl-1,3-thiazol-2-yl)ethyl]-1,3,4-thiadiazol-2-amine 75 5-[1-(3,5-dimethyl-1H-pyrazol-1-yl)ethyl]-N-{1-[(4-fluorophenyl)methyl]-1H-pyrazol-3-yl}-1,3,4-thiadiazol-2-amine 76 N-{1-[(2,6-difluorophenyl)methyl]-1H-pyrazol-3-yl}-5-[1-(3-methyl-1H-pyrazol-1-yl)ethyl]-1,3,4-thiadiazol-2-amine 77 5-[1-(3,5-dimethyl-1H-pyrazol-1-yl)ethyl]-N-{1-[(2,3,6-trifluorophenyl)methyl]-1H-pyrazol-3-yl}-1,3,4-thiadiazol-2-amine 78 1-[5-({1-[(2,6-difluorophenyl)methyl]-1H-pyrazol-3-yl}amino)-1,3,4-thiadiazol-2-yl]-1-(4-methyl-1,3-thiazol-2-yl)ethanol 79 1-[5-({1-[(3-chloro-2-fluorophenyl)methyl]-1H-pyrazol-3-yl}amino)-1,3,4-thiadiazol-2-yl]-1-(4-methyl-1,3-thiazol-2-yl)ethanol 80 1-[5-({1-[(2,3-difluorophenyl)methyl]-1H-pyrazol-3-yl}amino)-1,3,4-thiadiazol-2-yl]-1-(4-methyl-1,3-thiazol-2-yl)ethanol 81. N-{1-[(2,6-difluoro-3-methylphenyl)methyl]-1H-pyrazol-3-yl}-5-[1-(3,5-dimethyl-1H-pyrazol-1-yl)ethyl]-1,3,4-thiadiazol-2-amine 82 5-[1-(3,5-dimethyl-1H-pyrazol-1-yl)ethyl]-N-(1-{[2-(ethyloxy)-3,6-difluorophenyl]methyl}-1H-pyrazol-3-yl)-1,3,4-thiadiazol-2-amine 83 1-[5-({1-[(2-fluoro-3-methylphenyl)methyl]-1H-pyrazol-3-yl}amino)-1,3,4-thiadiazol-2-yl]-1-(4-methyl-1,3-thiazol-2-yl)ethanol 84 1-[5-({1-[(2,6-difluoro-3-methylphenyl)methyl]-1H-pyrazol-3-yl}amino)-1,3,4-thiadiazol-2-yl]-1-(4-methyl-1,3-thiazol-2-yl)ethanol 85 N-{1-[(2,6-difluoro-3-methylphenyl)methyl]-1H-pyrazol-3-yl}-5-[1-(4-methyl-1,3-thiazol-2-yl)ethyl]-1,3,4-thiadiazol-2-amine 86 N-{1-[(2,6-difluoro-3-methylphenyl)methyl]-1H-pyrazol-3-yl}-5-[1-(3-methyl-1H-pyrazol-1-yl)ethyl]-1,3,4-thiadiazol-2-amine 87 N-{1-[(3-amino-2,6-difluorophenyl)methyl]-1H-pyrazol-3-yl}-5-[1-(3,5-dimethyl-1H-pyrazol-1-yl)ethyl]-1,3,4-thiadiazol-2-amine 88 1-[5-({1-[(3-amino-2-fluorophenyl)methyl]-1H-pyrazol-3-yl}amino)-1,3,4-thiadiazol-2-yl]-1-(4-methyl-1,3-thiazol-2-yl)ethanol 89 (1S)-1-[5-({1-[(2,6-difluorophenyl)methyl]-1H-pyrazol-3-yl}amino)-1,3,4-thiadiazol-2-yl]-1-(4-methyl-1,3-thiazol-2-yl)ethanol and 90 (1R)-1-[5-({1-[(2,6-difluorophenyl)methyl]-1H-pyrazol-3-yl}amino)-1,3,4-thiadiazol-2-yl]-1-(4-methyl-1,3-thiazol-2-yl)ethanol, or a pharmaceutically acceptable salt thereof.

In one aspect, the invention provides a compound selected from:

1 5-[1-(3,5-dimethyl-1H-pyrazol-1-yl)ethyl]-N-(1-{[2-(trifluoromethyl)phenyl]methyl}-1H-pyrazol-3-yl)-1,3,4-thiadiazol-2-amine 2 N-{1-[(2,5-dichlorophenyl)methyl]-1H-pyrazol-3-yl}-5-[1-(3,5-dimethyl-1H-pyrazol-1-yl)ethyl]-1,3,4-thiadiazol-2-amine 3 N-{1-[(2-bromophenyl)methyl]-1H-pyrazol-3-yl}-5-[1-(3,5-dimethyl-1H-pyrazol-1-yl)ethyl]-1,3,4-thiadiazol-2-amine 4 N-{1-[(2,5-dichlorophenyl)methyl]-1H-pyrazol-3-yl}-5-[1-(3-methyl-1H-pyrazol-1-yl)ethyl]-1,3,4-thiadiazol-2-amine 5 N-{1-[(2-bromophenyl)methyl]-1H-pyrazol-3-yl}-5-[1-(3-methyl-1H-pyrazol-1-yl)ethyl]-1,3,4-thiadiazol-2-amine 6 5-[1-(3,5-dimethyl-1H-pyrazol-1-yl)ethyl]N-{1-[(2-fluorophenyl)methyl]-1H-pyrazol-3-yl}-1,3,4-thiadiazol-2-amine 7 N-{1-[(3-chloro-2-fluorophenyl)methyl]-1H-pyrazol-3-yl}-5-[1-(3,5-dimethyl-1H-pyrazol-1-yl)ethyl]-1,3,4-thiadiazol-2-amine 8 N-(1-{[2,5-bis(trifluoromethyl)phenyl]methyl}-1H-pyrazol-3-yl)-5-[1-(3,5-dimethyl-1H-pyrazol-1-yl)ethyl]-1,3,4-thiadiazol-2-amine 9 5-[1-(3,5-dimethyl-1H-pyrazol-1-yl)ethyl]-N-(1-{[5-fluoro-2-(trifluoromethyl)phenyl]methyl}-1H-pyrazol-3-yl)-1,3,4-thiadiazol-2-amine 10 N-{1-[(2,3-difluorophenyl)methyl]-1H-pyrazol-3-yl}-5-[1-(3,5-dimethyl-1H-pyrazol-1-yl)ethyl]-1,3,4-thiadiazol-2-amine 11 N-(1-{[2-chloro-5-(trifluoromethyl)phenyl]methyl}-1H-pyrazol-3-yl)-5-[1-(3,5-dimethyl-1H-pyrazol-1-yl)ethyl]-1,3,4-thiadiazol-2-amine 12 N-{1-[(2,6-difluorophenyl)methyl]-1H-pyrazol-3-yl}-5-[1-(3,5-dimethyl-1H-pyrazol-1-yl)ethyl]-1,3,4-thiadiazol-2-amine 13 N-{1-[(2-fluoro-3-methylphenyl)methyl]-1H-pyrazol-3-yl}-5-[1-(3-methyl-1H-pyrazol-1-yl)ethyl]-1,3,4-thiadiazol-2-amine 14 N-{1-[(3-chloro-2-fluorophenyl)methyl]-1H-pyrazol-3-yl}-5-[1-(3-methyl-1H-pyrazol-1-yl)ethyl]-1,3,4-thiadiazol-2-amine 15 N-{1-[(2,3-difluorophenyl)methyl]-1H-pyrazol-3-yl}-5-[1-(3-methyl-1H-pyrazol-1-yl)ethyl]-1,3,4-thiadiazol-2-amine 16 N-{1-[(2,3-difluorophenyl)methyl]-1H-pyrazol-3-yl}-5-[1-(4-methyl-1,3-thiazol-2-yl)ethyl]-1,3,4-thiadiazol-2-amine 17 N-{1-[(2-chloro-4-fluorophenyl)methyl]-1H-pyrazol-3-yl}-5-[1-(3,5-dimethyl-1H-pyrazol-1-yl)ethyl]-1,3,4-thiadiazol-2-amine 18 N-{1-[(2-chloro-4-fluorophenyl)methyl]-1H-pyrazol-3-yl}-5-[1-(3-methyl-1H-pyrazol-1-yl)ethyl]-1,3,4-thiadiazol-2-amine 19 N-{1-[(2-chloro-6-fluorophenyl)methyl]-5-methyl-1H-pyrazol-3-yl}-5-[1-(3,5-dimethyl-1H-pyrazol-1-yl)ethyl]-1,3,4-thiadiazol-2-amine 20 5-[1-(3,5-dimethyl-1H-pyrazol-1-ethyl]-N-{1-[(2-methylphenyl)methyl]-1H-pyrazol-3-yl}-1,3,4-thiadiazol-2-amine.

21 5-[1-(3,5-dimethyl-1H-pyrazol-1-yl)ethyl]-N-[1-(phenylmethyl)-1H-pyrazol-3-yl]-1,3,4-thiadiazol-2-amine N-{1-[(6-chloro-2-fluoro-3-methylphenyl)methyl]-1H-pyrazol-3-yl}-5-[1-(3,5-dimethyl-1H-pyrazol-1-yl)ethyl]-1,3,4-thiadiazol-2-amine 23 N-{1-[(2-chloro-6-fluoro-3-methylphenyl)methyl]-1H-pyrazol-3-yl}-5-[1-(3,5-dimethyl-1H-pyrazol-1-yl)ethyl]-1,3,4-thiadiazol-2-amine 24 5-[1-(3,5-dimethyl-1H-pyrazol-1-yl)ethyl]-N-{1-[(2-fluoro-3-methylphenyl)methyl]-1H-pyrazol-3-yl}-1,3,4-thiadiazol-2-amine 25 N-{1-[(2-fluoro-3-methylphenyl)methyl]-1H-pyrazol-3-yl}-5-[1-(4-methyl-1,3-thiazol-2-yl)ethyl]-1,3,4-thiadiazol-2-amine 26 N-{1-[(5-amino-2-chlorophenyl)methyl]-1H-pyrazol-3-yl}-5-[1-(3,5-dimethyl-1H-pyrazol-1-yl)ethyl]-1,3,4-thiadiazol-2-amine 27 N-{1-[(3-amino-2-methylphenyl)methyl]-1H-pyrazol-3-yl}-5-[1-(3,5-dimethyl-1H-pyrazol-1-yl)ethyl]-1,3,4-thiadiazol-2-amine 28 N-{1-[(2-chloro-6-fluorophenyl)methyl]-1H-pyrazol-3-yl}-5-[1-(3,5-dimethyl-1H-pyrazol-1-yl)ethyl]-1,3,4-thiadiazol-2-amine 29 N-{1-[(2-chloro-6-fluorophenyl)methyl]-1H-pyrazol-3-yl}-5-[1-(4-methyl-1,3-thiazol-2-yl)ethyl]-1,3,4-thiadiazol-2-amine 30 1-[5-({1-[(2-chloro-6-fluorophenyl)methyl]-1H-pyrazol-3-yl}amino)-1,3,4-thiadiazol-2-yl]-1-(4-methyl-1,3-thiazol-2-yl)ethanol 31 N-{1-[(2-chloro-6-fluorophenyl)methyl]-1H-pyrazol-3-yl}-5-{1-[4-(trifluoromethyl)-1,3-thiazol-2-yl]ethyl}-1,3,4-thiadiazol-2-amine 32 N-{1-[(2-chloro-6-fluorophenyl)methyl]-1H-pyrazol-3-yl}-5-[(4-methyl-1,3-thiazol-2-yl)methyl]-1,3,4-thiadiazol-2-amine 33 N-{1-[(3-chloro-2-fluorophenyl)methyl]-1H-pyrazol-3-yl}-5-[1-(4-methyl-1,3-thiazol-2-yl)ethyl]-1,3,4-thiadiazol-2-amine 34 N-{1-[(4-chlorophenyl)methyl]-1H-pyrazol-3-yl}-5-[1-(3,5-dimethyl-1H-pyrazol-1-yl)ethyl]-1,3,4-thiadiazol-2-amine 35 5-[1-(3,5-dimethyl-1H-pyrazol-1-yl)ethyl]-N-(1-{[4-(trifluoromethyl)phenyl]methyl}-1H-pyrazol-3-yl)-1,3,4-thiadiazol-2-amine 36 N-{1-[(2-chloro-5-fluorophenyl)methyl]-1H-pyrazol-3-yl}-5-[1-(3,5-dimethyl-1H-pyrazol-1-yl)ethyl]-1,3,4-thiadiazol-2-amine and 37 N-{1-[(2-chloro-6-fluorophenyl)methyl]-1H-pyrazol-3-yl}-5-[(3,5-dimethyl-1H-pyrazol-1-yl)methyl]-1,3-thiazol-2-amine, or a pharmaceutically acceptable salt thereof.

In one aspect, the invention provides a compound selected from:

72 N-{1-[(2-chloro-6-fluorophenyl)methyl]-1H-pyrazol-3-yl}-5-[1-(methyloxy)-1-(4-methyl-1,3-thiazol-2-yl)ethyl]-1,3,4-thiadiazol-2-amine 73 N-{1-[(2,6-difluorophenyl)methyl]-1H-pyrazol-3-yl}-5-[(methyloxy)(4-methyl-1,3-thiazol-2-yl)methyl]-1,3,4-thiadiazol-2-amine 74 N-{1-[(2-chloro-6-fluorophenyl)methyl]-1H-pyrazol-3-yl}-5-[1-methyl-1-(4-methyl-1,3-thiazol-2-yl)ethyl]-1,3,4-thiadiazol-2-amine 75 5-[1-(3,5-dimethyl-1H-pyrazol-1-yl)ethyl]-N-{1-[(4-fluorophenyl)methyl]-1H-pyrazol-3-yl}-1,3,4-thiadiazol-2-amine 76 N-{1-[(2,6-difluorophenyl)methyl]-1H-pyrazol-3-yl}-5-[1-(3-methyl-1H-pyrazol-1-yl)ethyl]-1,3,4-thiadiazol-2-amine 77 5-[1-(3,5-dimethyl-1H-pyrazol-1-yl)ethyl]-N-{1-[(2,3,6-trifluorophenyl)methyl]-1H-pyrazol-3-yl}-1,3,4-thiadiazol-2-amine 78 1-[5-({1-[(2,6-difluorophenyl)methyl]-1H-pyrazol-3-yl}amino)-1,3,4-thiadiazol-2-yl]-1-(4-methyl-1,3-thiazol-2-yl)ethanol 79 1-[5-({1-[(3-chloro-2-fluorophenyl)methyl]-1H-pyrazol-3-yl}amino)-1,3,4-thiadiazol-2-yl]-1-(4-methyl-1,3-thiazol-2-yl)ethanol 80 1-[5-({1-[(2,3-difluorophenyl)methyl]-1H-pyrazol-3-yl}amino)-1,3,4-thiadiazol-2-yl]-1-(4-methyl-1,3-thiazol-2-yl)ethanol 81 N-{1-[(2,6-difluoro-3-methylphenyl)methyl]-1H-pyrazol-3-yl}-5-[1-(3,5-dimethyl-1H-pyrazol-1-yl)ethyl]-1,3,4-thiadiazol-2-amine and 82 5-[1-(3,5-dimethyl-1H-pyrazol-1-yl)ethyl]-N-(1-{[2-(ethyloxy)-3,6-difluorophenyl]methyl}-1H-pyrazol-3-yl)-1,3,4-thiadiazol-2-amine, or a pharmaceutically acceptable salt thereof.

In one aspect, the invention provides a compound selected from:

83 1-[5-({1-[(2-fluoro-3-methylphenyl)methyl]-1H-pyrazol-3-yl}amino)-1,3,4-thiadiazol-2-yl]-1-(4-methyl-1,3-thiazol-2-yl)ethanol 84 1-[5-({1-[(2,6-difluoro-3-methylphenyl)methyl]-1H-pyrazol-3-yl}amino)-1,3,4-thiadiazol-2-yl]-1-(4-methyl-1,3-thiazol-2-yl)ethanol 85 N-{1-[(2,6-difluoro-3-methylphenyl)methyl]-1H-pyrazol-3-yl}-5-[1(4-methyl-1,3-thiazol-2-yl)ethyl]-1,3,4-thiadiazol-2-amine 86 N{1-[(2,6-difluoro-3-methylphenyl)methyl]-1H-pyrazol-3-yl}-5-[1-(3-methyl-1H-pyrazol-1-yl)ethyl]-1,3,4-thiadiazol-2-amine 87 N-{1-[(3-amino-2,6-difluorophenyl)methyl]-1H-pyrazol-3-yl}-5-[1-(3,5-dimethyl-1H-pyrazol-1-yl)ethyl]-1,3,4-thiadiazol-2-amine and 88 1-[5-({1-[(3-amino-2-fluorophenyl)methyl]-1H-pyrazol-3-yl}amino)-1,3,4-thiadiazol-2-yl]-1-(4-methyl-1,3-thiazol-2-yl)ethanol, or a pharmaceutically acceptable salt thereof.

In one aspect, the invention provides a compound selected from:

66 N-{1-[(2-chloro-6-fluorophenyl)methyl]-1H-pyrazol-3-yl}-5-[(1R)-1-(3-methyl-1H-pyrazol-1-yl)ethyl]-1,3,4-thiadiazol-2-amine 67 N-{1-[(2-chloro-6-fluorophenyl)methyl]-1H-pyrazol-3-yl}-5-[(1S)-1-(3-methyl-1H-pyrazol-1-yl-ethyl]-1,3,4-thiadiazol-2-amine 68 N-{1-[(2-chloro-6-fluorophenyl)methyl]-1H-pyrazol-3-yl}-5-[(1R)-1-(3,5-dimethyl-1H-pyrazol-1-yl)ethyl]-1,3,4-thiadiazol-2-amine 69 N-{1-[(2-chloro-6-fluorophenyl)methyl]-1H-pyrazol-3-yl}-5-[(1S)-1-(3,5-dimethyl-1H-pyrazol-1-yl)ethyl]-1,3,4-thiadiazol-2-amine 70 (1S)-1-[5-({1-[(2-chloro-6-fluorophenyl)methyl]-1H-pyrazol-3-yl}amino)-1,3,4-thiadiazol-2-yl]-1-(4-methyl-1,3-thiazol-2-yl)ethanol and 71 (1R)-1-[5-({1-[(2-chloro-6-fluorophenyl)methyl]-1H-pyrazol-3-yl}amino)-1,3,4-thiadiazol-2-yl]-1-(4-methyl-1,3-thiazol-2-yl)ethanol, or a pharmaceutically acceptable salt thereof.

In one aspect, the invention provides a compound selected from:

89 (1S)-1-[5-({1-[(2,6-difluorophenyl)methyl]-1H-pyrazol-3-yl}amino)-1,3,4-thiadiazol-2-yl]-1-(4-methyl-1,3-thiazol-2-yl)ethanol and 90 (1R)-1-[5-({1-[(2,6-difluorophenyl)methyl]-1H-pyrazol-3-yl}amino)-1,3,4-thiadiazol-2-yl]-1-(4-methyl-1,3-thiazol-2-yl)ethanol, or a pharmaceutically acceptable salt thereof.

In another aspect, the invention provides a compound of Examples 66 to 71, 89 and 90 as a single enantiomer, for example, in at least 98% enantiomeric excess (e.e.).

In one aspect, the invention provides a compound selected from:

67 N-{1-[(2-chloro-6-fluorophenyl)methyl]-1H-pyrazol-3-yl}-5-[(1S)-1-(3-methyl-1H-pyrazol-1-yl)ethyl]-1,3,4-thiadiazol-2-amine 69 N-{1-[(2-chloro-6-fluorophenyl)methyl]-1H-pyrazol-3-yl}-5-[(1S)-1-(3,5-dimethyl-1H-pyrazol-1-yl)ethyl]-1,3,4-thiadiazol-2-amine 70 (1S)-1-[5-({1-[(2-chloro-6-fluorophenyl)methyl]-1H-pyrazol-3-yl}amino)-1,3,4-thiadiazol-2-yl]-1-(4-methyl-1,3-thiazol-2-yl)ethanol and 89 (1S)-1-[5-({1-[(2,6-difluorophenyl)methyl]-1H-pyrazol-3-yl}amino)-1,3,4-thiadiazol-2-yl]-1-(4-methyl-1,3-thiazol-2-yl)ethanol, or a pharmaceutically acceptable salt thereof.

In another aspect, compounds which are useful in the present invention include:

38 N-{1-[(2-chloro-6-fluorophenyl)methyl]-1H-pyrazol-3-yl}-5-[1-(3-methyl-1H-pyrazol-1-yl)ethyl]-1,3,4-thiadiazol-2-amine 39 N-{1-[(2-chloro-6-fluorophenyl)methyl]-1H-pyrazol-3-yl}-5-[(3-methyl-1H-pyrazol-1-yl)methyl]-1,3,4-thiadiazol-2-amine 40 N-{1-[(2-chlorophenyl)methyl]-1H-pyrazol-3-yl}-5-[1-(5-methyl-3-nitro-1H-pyrazol-1-yl)ethyl]-1,3,4-thiadiazol-2-amine 41 N-{1-[(2-chlorophenyl)methyl]-1H-pyrazol-3-yl}-5-{1-[3-(difluoromethyl)-5-methyl-1H-pyrazol-1-yl]ethyl}-1,3,4-thiadiazol-2-amine 42 N-{1-[(2-chlorophenyl)methyl]-1H-pyrazol-3-yl}-5-[1-(3-methyl-1H-pyrazol-1-yl)ethyl]-1,3,4-thiadiazol-2-amine 43 5-{1-[3-(difluoromethyl)-5-methyl-1H-pyrazol-1-yl]ethyl}-N-[1-(phenylmethyl)-1H-pyrazol-3-yl]-1,3,4-thiadiazol-2-amine 44 5-[1-(3-methyl-1H-pyrazol-1-yl)ethyl]-N-[1-(phenylmethyl)-1H-pyrazol-3-yl]-1,3,4-thiadiazol-2-amine 5-{[3-(difluoromethyl)-5-methyl-1H-pyrazol-1-yl]methyl}-N-[1-(phenylmethyl)-1H-pyrazol-3-yl]-1,3,4-thiadiazol-2-amine 46 N-{1-[(2-chlorophenyl)methyl]-1H-pyrazol-3-yl}-5-{[3-(difluoromethyl)-5-methyl-1H-pyrazol-1-yl]methyl}-1,3,4-thiadiazol-2-amine 47 N-{1-[(2,6-dichlorophenyl)methyl]-1H-pyrazol-3-yl}-5-[(3-nitro-1H-pyrazol-1-yl)methyl]-1,3,4-thiadiazol-2-amine 48 N-{1-[(2-chlorophenyl)methyl]-1H-pyrazol-3-yl}-5-{[5-methyl-3-(trifluoromethyl)-1H-pyrazol-1-yl]methyl}-1,3,4-thiadiazol-2-amine
49 N-{1-[(2-chlorophenyl)methyl]-1H-pyrazol-3-yl}-5-[(3-nitro-1H-pyrazol-1-yl)methyl]-1,3,4-thiadiazol-2-amine
50 N-{1-[(2-chloro-6-fluorophenyl)methyl]-1H-pyrazol-3-yl}-5-[(5-methyl-3-nitro-1H-pyrazol-1-yl)methyl]-1,3,4-thiadiazol-2-amine
51 N-{1-[(2-chloro-6-fluorophenyl)methyl]-1H-pyrazol-3-yl}-5-[(3,5-dimethyl-1H-pyrazol-1-yl)methyl]-1,3,4-thiadiazol-2-amine
52 N-{1-[(2-chloro-6-fluorophenyl)methyl]-1H-pyrazol-3-yl}-5-[(3-nitro-1H-pyrazol-1-yl)methyl]-1,3,4-thiadiazol-2-amine
53 N-{1-[(2,6-dichlorophenyl)methyl]-1H-pyrazol-3-yl}-5-[(3,5-dimethyl-1H-pyrazol-1-yl)methyl]-1,3,4-thiadiazol-2-amine
54 N-{1-[(2,6-dichlorophenyl)methyl]-1H-pyrazol-3-yl}-5-[1-(3-methyl-1H-pyrazol-1-yl)ethyl]-1,3,4-thiadiazol-2-amine
55 N-{1-[(2-chloro-6-fluorophenyl)methyl]-1H-pyrazol-3-yl}-5-{[3-(difluoromethyl)-5-methyl-1H-pyrazol-1-yl]methyl}-1,3,4-thiadiazol-2-amine
56 N-{1-[(2-chlorophenyl)methyl]-1H-pyrazol-3-yl}-5-[(3,5-dimethyl-1H-pyrazol-1-yl)methyl]-1,3,4-thiadiazol-2-amine
57 N-{1-[(2,6-dichlorophenyl)methyl]-1H-pyrazol-3-yl}-5-[(3-methyl-1H-pyrazol-1-yl)methyl]-1,3,4-thiadiazol-2-amine
58 N-{1-[(2-chlorophenyl)methyl]-1H-pyrazol-3-yl}-5-[(5-methyl-3-nitro-1H-pyrazol-1-yl)methyl]-1,3,4-thiadiazol-2-amine
59 N-{1-[(2-chlorophenyl)methyl]-1H-pyrazol-3-yl}-5-{[3-(trifluoromethyl)-1H-pyrazol-1-yl]methyl}-1,3,4-thiadiazol-2-amine
60 5-[(3-methyl-1H-pyrazol-1-yl)methyl]-N-[1-(phenylmethyl)-1H-pyrazol-3-yl]-1,3,4-thiadiazol-2-amine
61 N-[1-(phenylmethyl)-1H-pyrazol-3-yl]-5-{[3-(trifluoromethyl)-1H-pyrazol-1-yl]methyl}-1,3,4-thiadiazol-2-amine
62 5-[(5-methyl-3-nitro-1H-pyrazol-1-yl)methyl]-N-[1-(phenylmethyl)-1H-pyrazol-3-yl]-1,3,4-thiadiazol-2-amine
63 N-{1-[(2-chloro-6-fluorophenyl)methyl]-1H-pyrazol-3-yl}-5-{[3-(trifluoromethyl)-1H-pyrazol-1-yl]methyl}-1,3,4-thiadiazol-2-amine
64 5-[(3,5-dimethyl-1H-pyrazol-1-yl)methyl]-N-[1-(phenylmethyl)-1H-pyrazol-3-yl]-1,3,4-thiadiazol-2-amine and
65 N-{1-[(2,6-dichlorophenyl)methyl]-1H-pyrazol-3-yl}-5-[1-(5-methyl-3-nitro-1H-pyrazol-1-yl)methyl]-1,3,4-thiadiazol-2-amine,
or a pharmaceutically acceptable salt thereof.

In another aspect, a compound of Formula (X) is useful in the present invention:

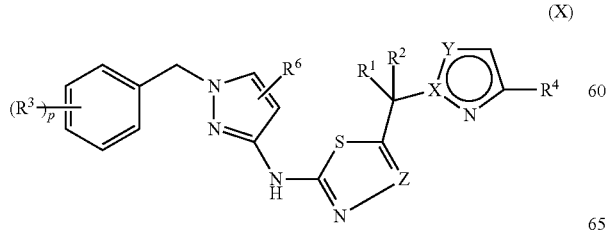

wherein:
either X is N and Y is $CR^5$; or X is C and Y is S;
Z is selected from N and CH;
$R^1$ is selected from H and Me,
$R^2$ is selected from H, OH, OMe and Me;
One $R^3$ group is $NHR^A$ and the remaining $R^3$ groups are independently selected from $C_{1-3}$alkyl, F, Cl, Br, $CF_3$ and $NHR^A$;
$R^4$ is selected from Me, $CF_3$, $NO_2$ and $CHF_2$;
$R^5$ is selected from H, Me and $CHF_2$;
$R^6$ is selected from H and Me;
Each $R^A$ is independently selected from —C(O)$C_{1-4}$alkyl or —C(O)O$C_{1-4}$alkyl; and
p is 0-3.

In another aspect, compounds which are useful in the present invention include:
A Ethyl (2-fluoro-3-{[3-({5-[1-hydroxy-1-(4-methyl-1,3-thiazol-2-yl)ethyl]-1,3,4-thiadiazol-2-yl}amino)-1H-pyrazol-1-yl]methyl}phenyl)carbamate and
B N-(3-{[3-({5-[1-(3,5-dimethyl-1H-pyrazol-1-yl)ethyl]-1,3,4-thiadiazol-2-yl}amino)-1H-pyrazol-1-yl]methyl}-2,4-difluorophenyl)acetamide,
or a pharmaceutically acceptable salt thereof.

In one aspect the invention provides a process for the preparation of a compound of Formula (Ia) wherein:
either X is N and Y is $CR^S$; or X is C and Y is S;
$R^1$ is selected from H and Me,
$R^2$ is selected from H, OH, OMe and Me;
each $R^3$ is independently selected from $C_{1-3}$alkyl, F, Cl, Br, $CF_3$ and $NH_2$;
$R^4$ is selected from Me, $CF_3$, $NO_2$ and $CHF_2$;
$R^6$ is selected from H, Me and $CHF_2$;
$R^6$ is selected from H and Me; and
p is 0-3,
comprising the step of reacting of compound of Formula (II) with a compound of Formula (III):

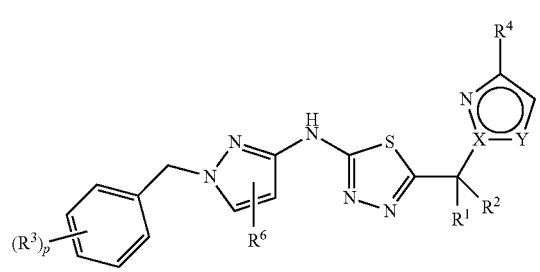

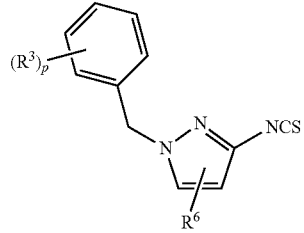

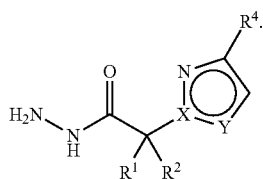

In another aspect, the compound of Formula (II) is reacted with the compound of Formula (III) in a suitable solvent such as DCM or ethanol. In another aspect the process of preparing a compound of Formula (Ia) comprises the step of reacting a hydrazinecarbothioamide intermediate prepared from the reaction of a compound of Formula (II) with the compound of Formula (III) with a dehydrating reagent, such as $H_2SO_4$ or $POCl_3$.

In one aspect the invention provides a process for the preparation of a compound of Formula (Ib) wherein:
either X is N and Y is $CR^5$; or X is C and Y is S;
$R^1$ is selected from H and Me;
$R^2$ is selected from H, OH, OMe and Me;
each $R^3$ is independently selected from $C_{1-3}$alkyl, F, Cl, Br, $CF_3$ and $NH_2$;
$R^4$ is selected from Me, $CF_3$, $NO_2$ and $CHF_2$;
$R^5$ is selected from H, Me and $CHF_2$;
$R^6$ is selected from H and Me; and
p is 0-3,
comprising the step of reacting a compound of Formula (IIb) with a compound of Formula (IIIb)

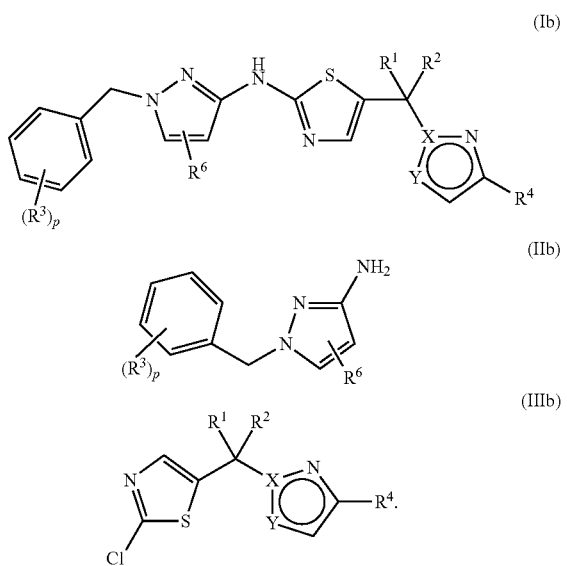

In another aspect the compound of Formula (IIIb) is reacted with the compound of Formula (IIIb) in the presence of a base, for example, a hindered, non-nucleophilic base, such as $^t$BuONa or $^t$BuOK.

Terms and Definitions

The term "$(C_{1-3})$alkyl" as used herein refers to a straight or branched chain alkyl group having 1 to 3 carbon atoms. Examples of $(C_{1-3})$alkyl groups include methyl (Me), ethyl (Et), n-propyl, iso-propyl The term "$(C_{1-4})$alkyl" as used herein refers to a straight or branched chain alkyl group having 1 to 4 carbon atoms. Examples of $(C_{1-4})$alkyl groups include methyl (Me), ethyl (Et), propyl (Pr) (for example n-propyl, iso-propyl), butyl (Bu) (for example n-butyl, sec-butyl, iso-butyl, tert-butyl (t-Bu)).

The term "halo" as used herein refers to fluoro, chloro, bromo and iodo groups. In one aspect, the term "halo" as used herein refers to fluoro, chloro and bromo groups. In another aspect, the term "halo" as used herein refers to chloro, bromo and iodo groups.

The term "$(C_{1-3})$alkoxy" as used herein refers to a straight or branched chain alkoxy group having 1 to 3 carbon atoms. Examples of $(C_{1-3})$alkoxy groups include, methoxy, ethoxy, propoxy and isopropoxy.

The term "compounds of the invention" as used herein means a compound of Formula (I) or a pharmaceutically acceptable salt thereof. The term "a compound of the invention" means any one of the compounds of the invention as defined above.

Furthermore, it will be understood that phrases such as "a compound of Formula (I) or a pharmaceutically acceptable salt thereof" or "compounds of the invention" are intended to encompass the compound of Formula (I), a pharmaceutically acceptable salt or solvate of the compound of Formula (I), or any pharmaceutically acceptable combination of these. Thus by way of non-limiting example used here for illustrative purpose, "a compound of Formula (I) or a pharmaceutically acceptable salt thereof" encompasses a pharmaceutically acceptable salt of a compound of Formula (I) which is present as a solvate, or this phrase may include a mixture of a compound of Formula (I) and a salt of a compound of Formula (I).

It will be appreciated by those skilled in the art that whilst certain compounds of the invention can form pharmaceutically acceptable salts with an acid or a base, certain other compounds of the invention may not readily form such salts. It will be appreciated that all possible pharmaceutically acceptable salts of a compound of Formula (I) are contemplated to be within the scope of the present invention.

It will be further appreciated that all crystalline forms, polymorphs and enantiomers of the compounds of the invention, or mixtures thereof, are contemplated to be within the scope of the present invention. Unless otherwise specified (for example when the absolute stereochemistry is shown), for compounds of the invention which possess at least one stereocentre, and which can therefore form enantiomers (for example, when $R^1$ and $R^2$ are different from one another, e.g. when $R^1$ is as defined for Formula (I) and $R^2$ represents hydroxy (OH)), the compound can contain a mixture of enantiomers, for example a 1:1 mixture of enantiomers, i.e. a racemic mixture of enantiomers. These may be separated using conventional techniques such as chiral HPLC. For an isomer of compound of the invention for which the absolute stereochemistry is stated or which is otherwise described as a single enantiomer, said isomer of a compound of the invention has, in one embodiment, at least 80% e.e. In another embodiment, said isomer of a compound of the invention has at least 90% e.e., for example at least 95% e.e. In another embodiment said isomer of compound of the invention corresponds to at least 98% e.e, for example at least 99% e.e.

Some of the compounds of this invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Since the compounds of Formula (I) are intended for use in pharmaceutical compositions it will readily be understood that in particular embodiments they are provided in substantially pure form, for example at least 60% pure, more suitably at least 75% pure and particularly at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and more particularly from 10 to 59% of a compound of Formula (I) or pharmaceutically acceptable salt and/or solvate thereof.

Compound Preparation

The general procedures used to synthesise the compounds of Formula (I), are described in reaction Schemes 1-13 and are illustrated in the Examples.

Preparation of Compounds of Formula (I)

Compounds of Formula (Ia) which are thiadiazole compounds of Formula (I) wherein Z is N may be prepared according to Scheme 1 by reaction of an isothiacyanate of Formula (II), wherein p, $R^3$ and $R^6$ are as for Formula (I), and an hydrazide of formula (III), wherein $R^1$, $R^2$ and $R^4$ are as for Formula (I), via a hydrazinecarbothioamide intermediate which can either be isolated and purified, or employed directly in the next step without purification Compounds of Formula (Ib) which are thiazole compounds of Formula (I) wherein Z is CH may be prepared according to Scheme 2 by reaction of an amide of Formula (IIb), wherein p, $R^3$ and $R^6$ are as for Formula (I) and an halogenated thiazole of Formula (IIIb), wherein $R^1$, $R^2$ and $R^4$ are as for Formula (I), respectively.

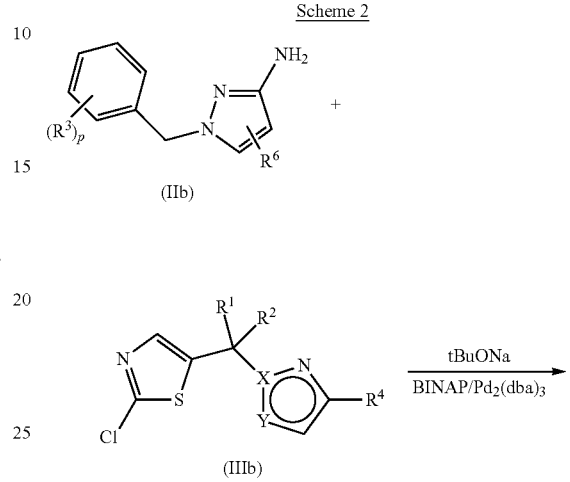

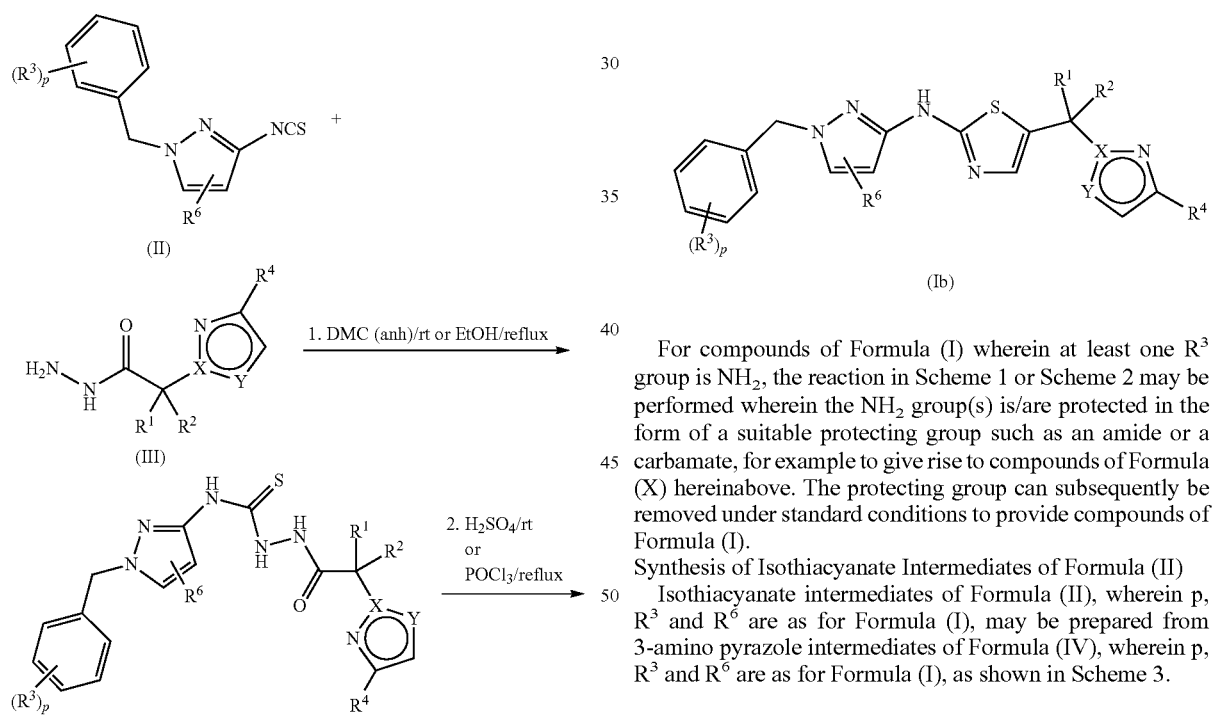

For compounds of Formula (I) wherein at least one $R^3$ group is $NH_2$, the reaction in Scheme 1 or Scheme 2 may be performed wherein the $NH_2$ group(s) is/are protected in the form of a suitable protecting group such as an amide or a carbamate, for example to give rise to compounds of Formula (X) hereinabove. The protecting group can subsequently be removed under standard conditions to provide compounds of Formula (I).

Synthesis of Isothiacyanate Intermediates of Formula (II)

Isothiacyanate intermediates of Formula (II), wherein p, $R^3$ and $R^6$ are as for Formula (I), may be prepared from 3-amino pyrazole intermediates of Formula (IV), wherein p, $R^3$ and $R^6$ are as for Formula (I), as shown in Scheme 3.

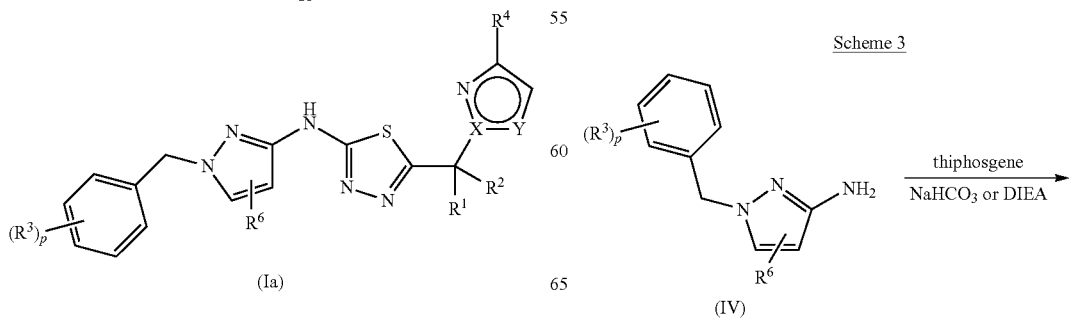

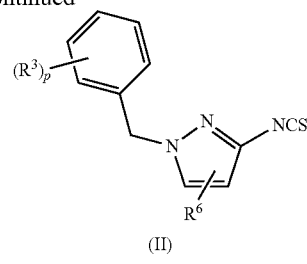

(II)

3-amino pyrazole intermediates of Formula (IV) can be prepared from protected intermediates of the Formula (V), wherein p, $R^3$ and $R^6$ are as for Formula (I), or intermediates of Formula (VI), wherein p, $R^3$ and $R^6$ are as for Formula (I), as shown in Schemes 4 and 5 respectively.

Scheme 4

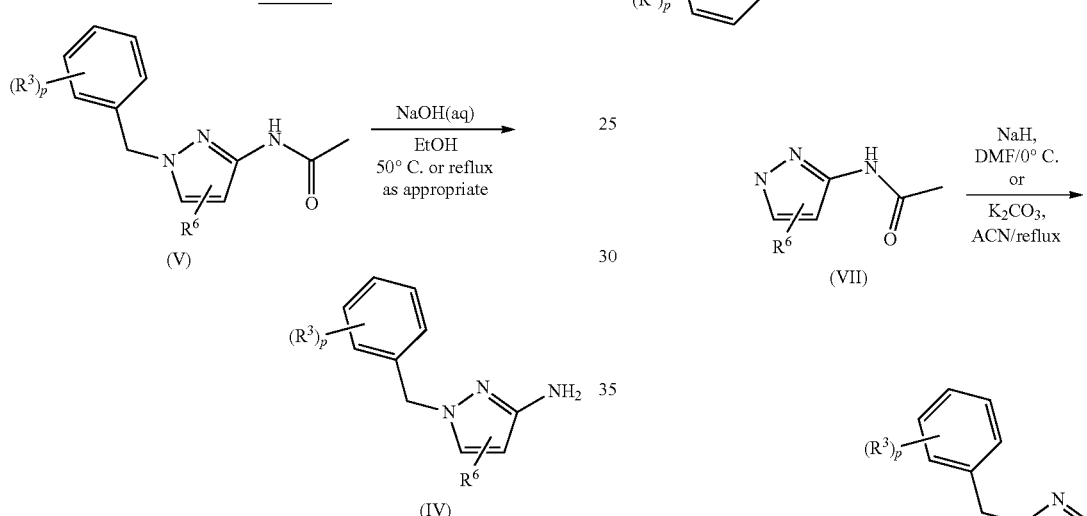

Scheme 5

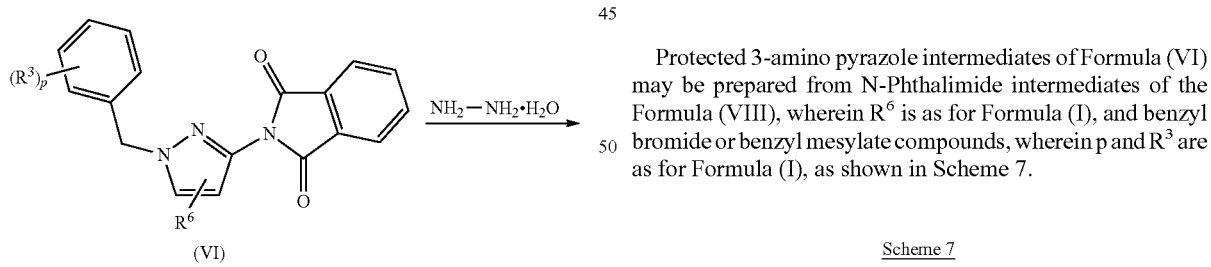

Protected 3-amino pyrazole compounds of Formula (V) may be prepared from a reaction between a 3-acetylamino pyrazole compound of the Formula (VII), wherein $R^6$ is as for Formula (I), and a benzyl bromide compound or a benzyl methylsulfonate (mesylate or OMs) compound, wherein p and $R^3$ are as for Formula (I), as shown in Scheme 6.

Scheme 6

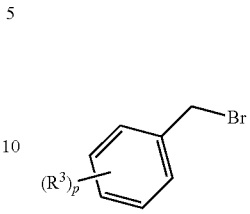

Protected 3-amino pyrazole intermediates of Formula (VI) may be prepared from N-Phthalimide intermediates of the Formula (VIII), wherein $R^6$ is as for Formula (I), and benzyl bromide or benzyl mesylate compounds, wherein p and $R^3$ are as for Formula (I), as shown in Scheme 7.

Scheme 7

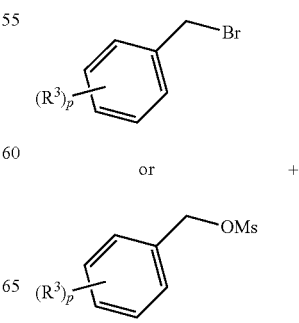

-continued

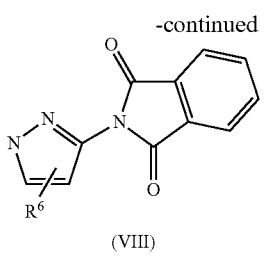
(VIII)

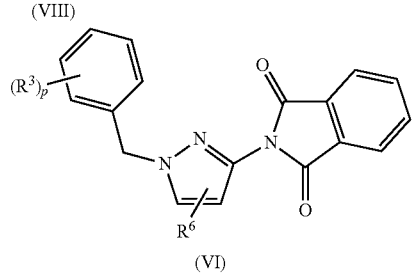
(VI)

Non-commercially available benzyl bromide compounds, or benzyl mesylate compounds in which one $R^3$ group is a protected amine, such as a Boc-protected amine, ethyloxycarbonyl-protected amine or acetyl-protected amine, may be prepared as shown in Scheme 8. In each case, the amine protecting group may be removed at a suitable stage in the preparation of compounds of Formula (I) to provide a compound of Formula (I) in which one $R^3$ group is $NH_2$.

Scheme 8

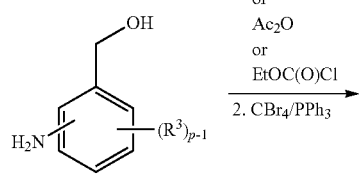

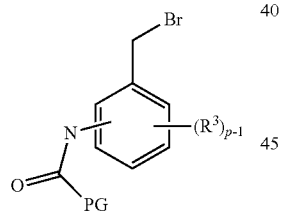

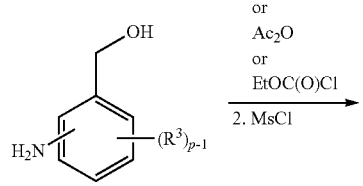

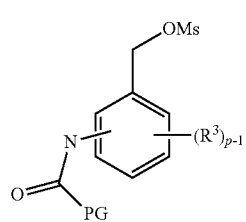

PG = t-BuO, EtO or Et

Protected 3-amino pyrazole intermediates of Formula (VII) and Formula (VIII) may be prepared from commercially available 3-amino pyrazoles, wherein $R^6$ is as for Formula (I), as shown in Schemes 9 and 10.

Scheme 9

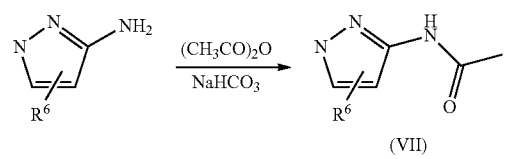
(VII)

Scheme 10

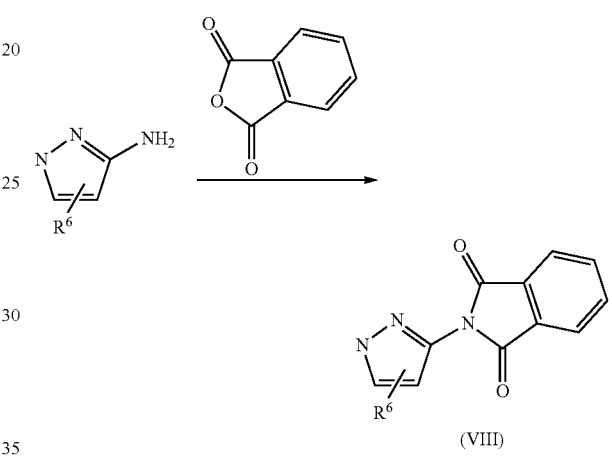
(VIII)

Synthesis of Hydrazine Intermediates of Formula (III)

Hydrazine intermediates of Formula (III), wherein $R^1$, $R^2$ and $R^4$ are as for Formula (I), may be prepared from N-alkyl pyrazole intermediates of the Formula (IX), wherein $R^1$, $R^2$ and $R^4$ are as for Formula (I) and $R^7$ is $(C_{1-4})$alkyl, as shown in Scheme 11.

Scheme 11

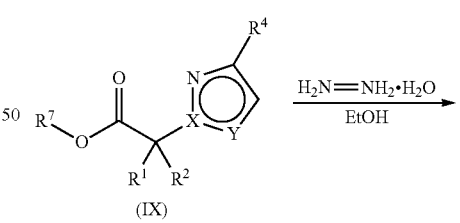
(IX)

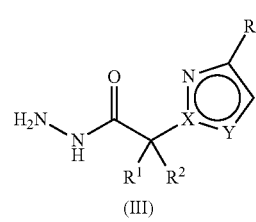
(III)

Compounds of Formula (IXa), which are N-alkyl pyrazole compounds of Formula (IX) wherein X is N and Y is $CR^5$ and $R^1$ and $R^4$ are as for Formula (I), $R^2$ is H or Me and $R^7$ is $(C_{1-4})$alkyl, may be prepared as shown in Scheme 12 from a commercially available alkyl bromide, wherein $R^1$ and $R^2$ are as for Formula (I) and $R^7$ is $(C_{1-4})$alkyl. Compounds of Formula (IXb), which are 2-alkyl 1,3 thiazole compounds of Formula (IX) wherein X is C and Y is S and $R^1$, $R^2$ and $R^4$ are as for Formula (I), and $R^7$ is $(C_{1-4})$alkyl, may be prepared as shown in Scheme 13, starting from a commercially available nitrile compound, wherein $R^1$ and $R^2$ are as for Formula (I) and $R^7$ is $(C_{1-4})$alkyl, via a thioamide intermediate compound.

Scheme 12

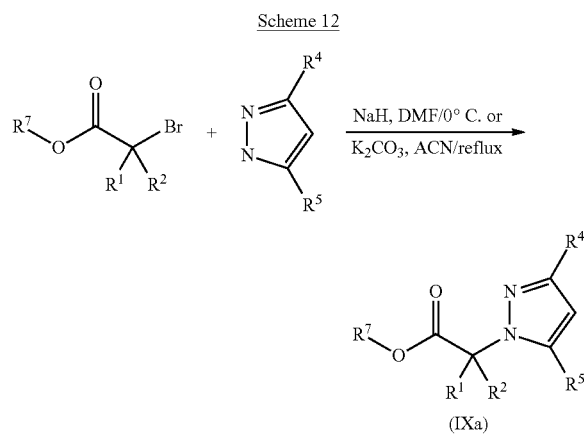

Scheme 13

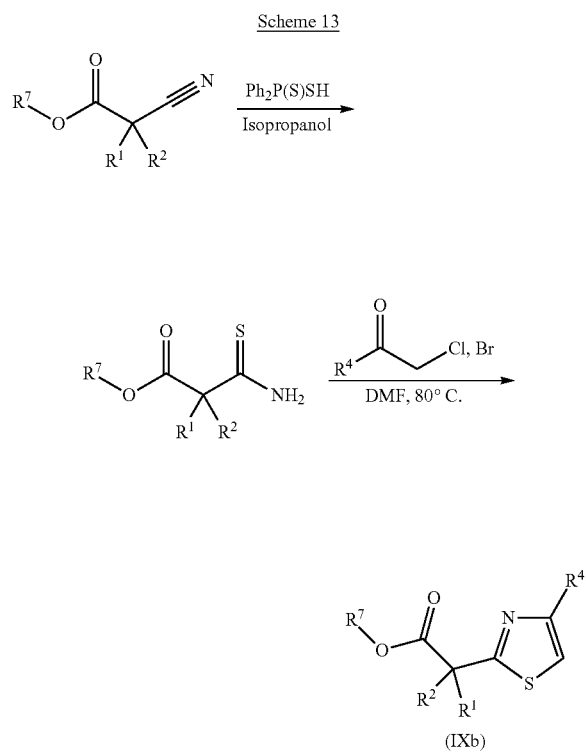

Compounds of Formula (IXb(i)), which are compounds of Formula (IXb) wherein $R^1$ is Me and $R^2$ is OH, may be prepared from compounds of Formula (IXb(ii)), which are compounds of Formula (IXb) wherein $R^1$ is Me and $R^2$ is H, according to Scheme 14.

Scheme 14

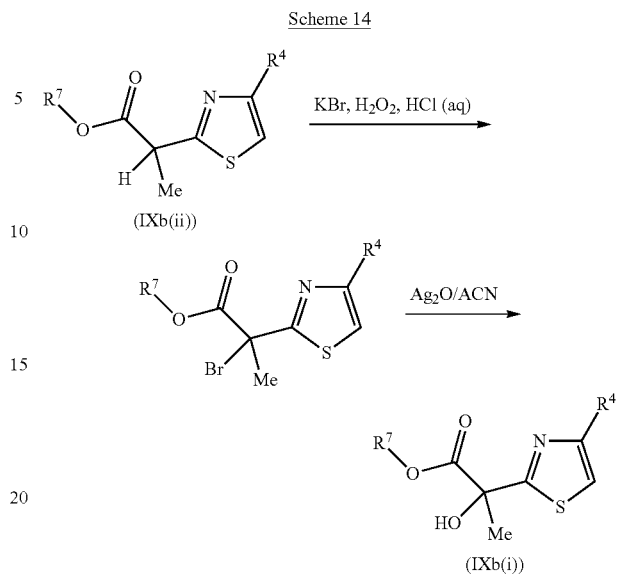

It should be noted that for compound (IXb(ii)) wherein $R^1$ is Me and $R^2$ is H, this compound will undergo slow autooxidation to give compound (IXb(i)) wherein $R^1$ is Me and $R^2$ is OH. Therefore compound (IXb(ii)) is best employed in the next reaction step (Scheme 11) as soon as it has been synthesised, to minimise autooxidation.

Those skilled in the art will appreciate that in the preparation of the compound of Formula (I), it may be necessary and/or desirable to protect one or more sensitive groups in the molecule or the appropriate intermediate to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), N-tert-butyloxycarbonyl (Boc), isopropyloxycarbonyl, cyclohexyloxycarbonyl, ethyloxycarbonyl) and alkyl or aralkyl type protecting groups (e.g. benzyl, trityl, chlorotrityl). Examples of suitable oxygen protecting groups may include for example alky silyl groups, such as trimethylsilyl or tert-butyldimethylsilyl; alkyl ethers such as tetrahydropyranyl or tert-butyl; or esters such as acetate.

It will be readily apparent to those skilled in the art that other compounds of Formula (I) may be prepared using methods analogous to those outlined above, or by reference to the experimental procedures detailed in the Examples provided herein. Further details for the preparation of compounds of Formula (I) are found in the Examples.

Compositions and Formulations

The compounds of the invention may be formulated for administration in any convenient way for use in human or veterinary medicine, by analogy with formulation of antibacterials, or formulation of other antitubercular agents.

The compounds of the invention will normally, but not necessarily, be formulated into pharmaceutical compositions prior to administration to a patient. In one aspect, the invention is directed to a pharmaceutical composition comprising a compound of Formula (I), or a pharmaceutically acceptable salt thereof. In another aspect the invention is directed to a pharmaceutical composition comprising a compound of Formula (I), or a pharmaceutically acceptable salt thereof, and one or more pharmaceutically acceptable carriers, excipients or diluents. The carrier, excipient or diluent must be "acceptable" in the sense of being compatible with the other ingredients of the formulation and not deleterious to the recipient thereof.

A therapeutically effective amount of the compound of the present invention can be determined by methods known in the art. The therapeutically effective quantities will depend on the age and on the general physiological condition of the subject, the route of administration and the pharmaceutical formulation used. The therapeutic doses will generally be between about 1 and 2000 mg/day. The daily dose as employed for acute or chronic human treatment will range from 0.01 to 250 mg/kg body weight, which may be administered in one to four daily doses, for example, depending on the route of administration and the condition of the subject. When the composition comprises dosage units, each unit will contain 1 mg to 2 g of active ingredient.

The present invention is further related to a pharmaceutical composition for the treatment of tuberculosis, comprising the compound of Formula (I) or a pharmaceutically acceptable salt thereof.

The present invention is even further related to a pharmaceutical composition comprising a) 1 to 2000 mg of the compound of Formula (I) or a pharmaceutically acceptable salt thereof, and b) 0.1 to 2 g of one or more pharmaceutically acceptable excipients.

The pharmaceutical compositions of the invention include those in a form adapted for oral, or parenteral use and may be used for the treatment of tuberculosis in mammals including humans.

The pharmaceutical compositions of the invention include those in a form adapted for oral or parenteral use in mammals including humans.

The composition may be formulated for administration by any convenient route. For the treatment of tuberculosis, the compositions may be in the form of tablets, capsules, powders, granules, lozenges, aerosols or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

In one aspect of the invention, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compound of Formula (I), or a pharmaceutically acceptable salt thereof, may be the sole therapeutic agent in the compositions of the invention, or it may be present in the formulation in combination with one or more additional therapeutic agents.

The invention thus provides in a further aspect, a combination comprising a compound of Formula (I), or a pharmaceutically acceptable salt thereof together with one or more additional therapeutic agents. Examples of such one or more additional therapeutic agents are anti-tuberculosis agents including, but not limited to, amikacin, aminosalicylic acid, capreomycin, cycloserine, ethambutol, ethionamide, isoniazid, kanamycin, pyrazinamide, rifamycins (such as rifampin, rifapentine and rifabutin), streptomycin, clarithromycin, azithromycin, oxazolidinones and fluoroquinolones (such as ofloxacin, ciprofloxacin, moxifloxacin and gatifloxacin). Such chemotherapy is determined by the judgment of the treating physician using preferred drug combinations. "First-line" chemotherapeutic agents used to treat a *Mycobacterium tuberculosis* infection that is not drug resistant include isoniazid, rifampin, ethambutol, streptomycin and pyrazinamide. "Second-line" chemotherapeutic agents used to treat a *Mycobacterium tuberculosis* infection that has demonstrated drug resistance to one or more "first-line" drugs include ofloxacin, ciprofloxacin, ethionamide, aminosalicylic acid, cycloserine, amikacin, kanamycin and capreomycin. In addition to the aforementioned, there is a number of new anti-tuberculosis therapeutic agents emerging from clinical studies that may also be employed as the one or more additional therapeutic agents in a combination with a compound of Formula (I), including, but not limited to, TMC-207, OPC-67683, PA-824, LL-3858 and SQ-109.

In another aspect, the invention provides a combination comprising a compound of Formula (I), or a pharmaceutically acceptable salt thereof together with one or more additional therapeutic agents, such as an anti-tuberculosis agent, especially isoniazid (INH), rifampin, pyrazinamide and ethambutol and/or an anti-bacterial agent or an anti-AIDS agent.

In a further aspect, the one or more additional therapeutic agent is, for example, an agent useful for the treatment of tuberculosis in a mammal, therapeutic vaccines, anti-bacterial agents, anti-viral agents; antibiotics and/or agents for the treatment of HIV/AIDS.

Examples of such therapeutic agents include isoniazid (INH), ethambutol, rifampin, pirazinamide, streptomycin, capreomycin, ciprofloxacin and clofazimine.

In one aspect, the one or more additional therapeutic agent is a therapeutic vaccine. A compound of Formula (I), or a pharmaceutically acceptable salt thereof, may thus be administered in conjunction with vaccination against mycobacterial infection, in particular vaccination against *Mycobacterium tuberculosis* infection. Existing vaccines against mycobacterial infection include *Bacillus* Calmette Guerin (BCG). Vaccines currently under development for the treatment, prophylaxis or amelioration of mycobacterial infection include: modified BCG strains which recombinantly express additional antigens, cytokines and other agents intended to improve efficacy or safety; attenuated mycobacteria which express a portfolio of antigens more similar to *Mycobacterium tuberculosis* than BCG; and subunit vaccines. Subunit vaccines may be administered in the form of one or more individual protein antigens, or a fusion or fusions of multiple protein antigens, either of which may optionally be adjuvanted, or in the form of a polynucleotide encoding one or more individual protein antigens, or encoding a fusion or fusions of multiple protein antigens, such as where the polynucleotide is administered in an expression vector. Examples of subunit vaccines include, but are not limited to: M72, a fusion protein derived from the antigens Mtb32a and Mtb39; HyVac-1, a fusion protein derived from antigen 85b and ESAT-6; HyVac-4, a fusion protein derived from antigen 85b and Tb10.4; MVA85a, a modified vaccinia virus Ankara expressing antigen 85a; and Aeras-402, adenovirus 35 expressing a fusion protein derived from antigen 85a, antigen 85b and Tb10.4.

The compound of Formula (I), or a pharmaceutically acceptable salt thereof, may be either i) administered to an individual who has previously been vaccinated against mycobacterial infection; ii) administered to an individual who is subsequently vaccinated against mycobacterial infection; or iii) may be co-administered with a vaccine against mycobacterial infection, either by administering the compound of the invention and the vaccine together in the same dosage form or co-administering the compound of the invention and the vaccine in separate dosage forms.

When a compound of Formula (I), or a pharmaceutically acceptable salt thereof is used in combination with one or more additional therapeutic agents, the dose of the compound or agent may differ from that when the compound or agent is used alone. Appropriate doses will be readily appreciated by those skilled in the art. It will be appreciated that the amount of a compound of the invention and the one or more additional therapeutic agents required for use in treatment will vary with the nature of the condition being treated and the age and the condition of the patient and will be ultimately at the discretion of the attendant physician or veterinarian.

The combinations may conveniently be presented for use in the form of a pharmaceutical formulation. In a further aspect of the present invention there is provided a pharmaceutical combination comprising a compound of Formula (I), or a pharmaceutically acceptable salt thereof, together with one or more additional therapeutic agents, and one or more pharmaceutically acceptable carriers, excipients or diluents. The individual components of such combinations may be administered either sequentially or simultaneously in separate or combined pharmaceutical formulations by any convenient route.

When administration is sequential, either the compound of the present invention or one or more additional therapeutic agent may be administered first. When administration is simultaneous, the combination may be administered either in the same or different pharmaceutical composition. When combined in the same formulation it will be appreciated that the compound and agents must be stable and compatible with each other and the other components of the formulation. When formulated separately they may be provided in any convenient formulation, conveniently in such manner as are known for such compounds in the art.

Abbreviations

In describing the invention, chemical elements are identified in accordance with the Periodic Table of the Elements. Abbreviations and symbols utilized herein are in accordance with the common usage of such abbreviations and symbols by those skilled in the chemical arts. The following abbreviations are used herein:

| | |
|---|---|
| EtOAc | ethyl acetate |
| Ac | acetyl |
| AcOH | acetic acid |
| Ac$_2$O | acetic anhydride |
| anh | anhydrous |
| Boc | N-tert-butoxycarbonyl |
| Boc anhydride | di-tert-butyl dicarbonate |
| Celite ® | a filter aid composed of acid-washed diatomaceous silica, (a trademark of Manville Corp., Denver, Colorado) |
| DME | dimethoxyethane |
| DCM | dichloromethane |
| DIBAL-H | diisobutyl aluminium hydride |
| DMF | dimethylformamide |
| DMSO-d6 | deuterated dimethylsulfoxide |
| DMSO | dimethylsulfoxide |
| ES MS | Electrospray mass spectrometry |
| Et | Ethyl |
| EtOH | ethanol |
| h | hours |
| HPLC | high performance liquid chromatography |
| Int. | Intermediate |
| LCMS | Liquid chromatography mass spectroscopy |
| Mesylate | methylsulfonate |
| Me | methyl |
| MeOH | methanol |
| Ms | methylsulfonate |
| min(s) | minutes |
| NaBH(OAc)$_3$ | sodium triacetoxyborohydride |
| NMR | Nuclear Magnetic Resonance spectroscopy |
| Rt | retention time |
| t-BuOMe | methyl t-butyl ether |
| t-BuO | tert-butyloxy |
| TFA | trifluoroacetic acid |
| THF | tetrahydrofuran |
| uv | ultraviolet |

EXAMPLES

The following Examples illustrate the invention. These Examples are not intended to limit the scope of the invention, but rather to provide guidance to the skilled artisan to prepare and use the compounds, compositions, and methods of the invention. While particular embodiments of the invention are described, the skilled artisan will appreciate that various changes and modifications can be made. References to preparations carried out in a similar manner to, or by the general method of, other preparations, may encompass variations in routine parameters such as time, temperature, workup conditions, minor changes in reagent amounts etc.

Proton nuclear magnetic resonance ($^1$H NMR) spectra were recorded, and chemical shifts are reported in parts per million (δ) downfield from the internal standard tetramethylsilane (TMS). Abbreviations for NMR data are as follows: s=singlet, d=doublet, t=triplet, q=quartet, m=multiplet, dd=doublet of doublets, dt=doublet of triplets, app=apparent, br=broad. Mass spectra were obtained using electrospray (ES) ionization techniques. All temperatures are reported in degrees centigrade.

Reactions involving metal hydrides including lithium hydride, lithium aluminium hydride, di-isobutylaluminium hydride, sodium hydride, sodium borohydride and sodium triacetoxyborohydride are carried out under argon or nitrogen unless otherwise specified.

Intermediates

Intermediate 1

N-1H-pyrazol-3-ylacetamide

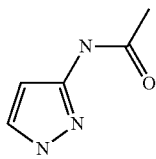

1H-pyrazol-3-amine (ALDRICH, 11.32 g, 0.136 mol) was dissolved in 100 mL of distilled water. NaHCO$_3$ (34 g, 0.408 mol) was slowly added. Acetic anhydride (27.55 g, 0.272 mol) was then added dropwise and the resulting suspension was heated at reflux overnight. Then, the mixture was allowed to cool down to r.t. and the solid obtained was filtered off and characterized as the title compound (8.4 g, 0.067 mol, 49%). After concentration of the filtrate, a second precipitate was obtained (2.7 g, 0.021 mol, 16%), also characterized as the title compound. $^1$H NMR (300 MHz, DMSO-d$_6$) δ ppm: 12.23 (br s, 1H), 10.30 (br s, 1H), 7.55 (br s, 1H), 6.45 (br s, 1H), 1.97 (s, 3H). [ES+MS] m/z 126 (MH$^+$).

Intermediate 2

1,1-dimethylethyl [4-chloro-3-(hydroxymethyl)phenyl]carbamate

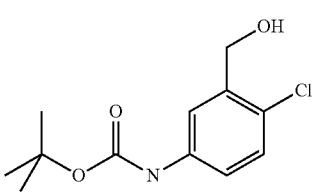 [SMILES: CC(C)(C)OC(=O)Nc1ccc(Cl)c(CO)c1]

To a solution of (5-amino-2-chlorophenyl)methanol (Aldrich, 500 mg, 3.17 mmol) in a mixture of dioxane (7.5 mL), water (7.5 mL) was added sodium carbonate (336 mg, 3.17 mmol) previously dissolved in 4 mL of water. Solution was stirred and cooled in an ice bath. Boc-anhydride (Aldrich, 692 mg, 3.17 mmol) was added in one portion, and stirring was continued at room temperature for 3 h. Dioxane was removed in vacuo conditions and the aqueous layer chilled, covered with a layer of ethyl acetate, and acidified to pH 4 with dilute KHSO$_4$ (10%, aq) (ALDRICH). This was followed by extraction (EtOAc) and purification by chromatographic column 25 g cartridge (ISOLUTE silice) using Hex/EtOAc 100/0 to 50/50, giving 1,1-dimethylethyl [4-chloro-3-(hydroxymethyl)phenyl]carbamate (560 mg, 2.17 mmol, 68%). $^1$H NMR (300 MHz, DMSO-d$_6$) δ ppm: 9.46 (br s, 1H), 7.72 (s, 1H), 7.21-7.32 (m, 2H), 5.35 (t, 1H), 4.48 (d, 2H), 1.47 (s, 9H).

Intermediate 3

1,1-dimethylethyl [3-(hydroxymethyl)-2-methylphenyl]carbamate

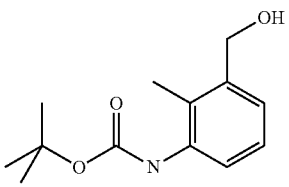 [SMILES: Cc1c(CO)cccc1NC(=O)OC(C)(C)C]

The title compound was prepared following the procedure described above for Intermediate 2. (3-amino-2-methylphenyl)methanol (Aldrich, 300 mg, 2.18 mmol) and Boc-anhydride (Aldrich, 716 mg, 3.28 mmol) were used as starting reactants. 1,1-dimethylethyl [3-(hydroxymethyl)-2-methylphenyl]carbamate (452 mg, 1.905 mmol, 87%) was obtained as a white solid. $^1$H NMR (300 MHz, DMSO-d$_6$) δ ppm: 8.53 (br s, 1H), 7.06-7.17 (m, 3H), 5.06 (t, 1H), 4.46 (d, 2H), 2.07 (s, 3H), 1.44 (s, 9H).

Intermediate 4

1,1-dimethylethyl [3-(bromomethyl)-4-chlorophenyl]carbamate

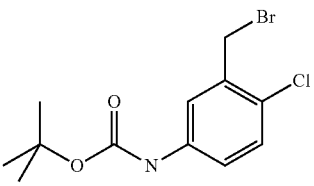 [SMILES: CC(C)(C)OC(=O)Nc1ccc(Cl)c(CBr)c1]

To a solution of Intermediate 2 (200 mg, 0.776 mmol) in DCM (5 mL) were added triphenylphospine (Aldrich, 244 mg, 0.931 mmol) and carbon tetrabromide (Aldrich, 386 mg, 1.164 mmol) in an ice-water bath. After 15 min, reaction mixture was stirred at room temperature for 15 min, mixture of reaction was checked by TLC (Hex:EtOAc) (1:1), and by LCMS reaction was completed. Solvent was evaporated under vacuum conditions. Residue was purified by chromatographic column 10 gr cartridge (ISOLUTE silica) using Hex/EtOAc 100/0 to 0/100. To yield 1,1-dimethylethyl [3-(bromomethyl)-4-chlorophenyl]carbamate (206 mg, 0.643 mmol, 83%) as a light yellow solid. $^1$H NMR (300 MHz, DMSO-d$_6$) δ ppm: 9.58 (br.s, 1H), 7.77 (br.s, 1H), 7.35 (m, 2H), 4.67 (s, 2H), 1.48 (s, 9H).

Intermediate 5

1,1-dimethylethyl [3-(bromomethyl)-2-methylphenyl]carbamate

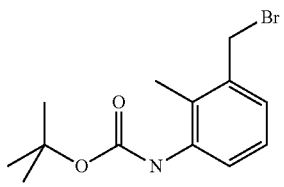 [SMILES: Cc1c(CBr)cccc1NC(=O)OC(C)(C)C]

The title compound was prepared following the procedure described above for Intermediate 4. Intermediate 3 (443 mg, 1.86 mmol), triphenylphospine (Aldrich, 588 mg, 2.24 mmol) and carbon tetrabromide (Aldrich, 929 mg, 2.80 mmol) as starting reactants. The title compound (293 mg, 0.976 mmol, 52%) was obtained as a white solid. $^1$H NMR (300 MHz, DMSO-d$_6$) δ ppm: 8.64 (br.s, 1H), 7.20-7.27 (m, 2H), 7.09-7.15 (m, 1H), 4.73-4.79 (m, 2H), 2.19-2.21 (m, 3H), 1.45 (s, 9H).

Intermediate 6

N-{1-[(2-chloro-6-fluorophenyl)methyl]-1H-pyrazol-3-yl}acetamide

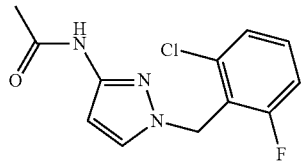 [SMILES: CC(=O)Nc1ccn(Cc2c(F)cccc2Cl)n1]

To a solution of Intermediate 1 (3 g, 24 mmol.) in dry DMF (40 mL) at 0° C., sodium hydride (0.63 g, 26.4 mmol.) was added and the mixture was kept at ice cold temperature with stirring for 30 min. To this solution, 2-(bromomethyl)-1-chloro-3-fluorobenzene (Aldrich, 5.36 g, 24 mmol.) was added dropwise over a period of 30 min, followed by another 30 min of stirring at ice cold temperature. The reaction was then quenched by the addition of water (1 mL). The resulting solution was diluted with EtOAc (150 mL) and washed with saturated NH$_4$Cl (3×60 mL). The organic fraction was dried over Na$_2$SO$_4$ and concentrated to dryness. Silica column chromatography (100% Hex to 100% EtOAc, 100 g, 30 min) gave N-{1-[(2-chloro-6-fluorophenyl)methyl]-1H-pyrazol-3-yl}acetamide (4.12 g, 64.2%). $^1$H NMR (300 MHz, CDCl$_3$) δ ppm: 7.71 (s, 1H), 7.05-7.36 (m, 4H), 6.65 (d, 1H), 5.34 (d, 2H), 210 (s, 3H) [ES+MS] m/z: 268 (MH+).

Intermediates 7-25 were prepared by a method analogous to that described for Intermediate 6 but replacing the benzyl bromide (2-(bromomethyl)-1-chloro-3-fluorobenzene) with that indicated in Table A.

TABLE A

| Int. | Structure | Benzyl bromide | Physical data |
|---|---|---|---|
| 7 | | LANCASTER | $^1$H NMR (300 MHz, DMSO-d$_6$) δ ppm: 10.43 (br. s, 1H), 7.75 (d, 1H), 7.51-7.54 (m, 1H), 7.41-7.45 (m, 1H), 7.08 (m, 1H), 6.51 (d, 1H), 5.31 (s, 2H), 1.96 (s, 3H). [ES + MS] m/z 285 (MH+). |
| 8 | | ALDRICH | $^1$H NMR (300 MHz, DMSO-d$_6$) δ ppm: 10.37 (br. s, 1H), 7.61 (d, 1H), 7.14-7.20 (m, 3H), 6.94-7.13 (m, 1H), 6.46 (d, 1H), 5.21 (s, 2H), 2.26 (s, 3H), 1.95 (s, 3H), [ES + MS] m/z 230 (MH+). |

TABLE A-continued

| Int. | Structure | Benzyl bromide | Physical data |
|---|---|---|---|
| 9 | 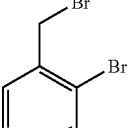 | 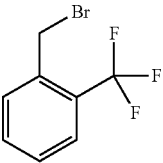 ALDRICH | $^1$H NMR (300 MHz, DMSO-d$_6$) δ ppm: 10.42 (br. s, 1H), 7.71 (d, 1H), 7.62-7.65 (m, 1H), 7.33-7.38 (m, 1H), 7.22-7.28 (m, 1H), 6.93-6.96 (m, 1H), 6.50 (d, 1H), 5.29 (s, 2H), 1.96 (s, 3H). [ES + MS] m/z 295 (MH+). |
| 10 | 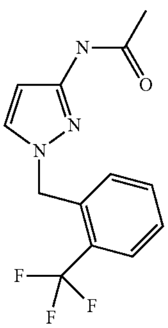 [SMILES: CC(=O)Nc1ccn(Cc2ccccc2C(F)(F)F)n1] | ALDRICH | $^1$H NMR (300 MHz, CDCl$_3$) δ ppm: 7.68-7.73 (m, 2H), 7.37-7.51 (m, 2H), 7.35 (d, 2H), 6.91 (d, 1H), 6.77 (d, 1H), 5.41 (br. s, 2H), 2.15 (s, 3H) [ES + MS] m/z 284 MH$^+$) |
| 11 | 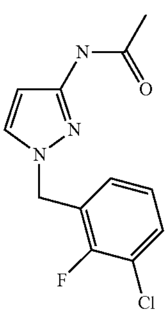 [SMILES: CC(=O)Nc1ccn(Cc2cccc(Cl)c2F)n1] | ALFAAESAR | $^1$H NMR (300 MHz, CDCl$_3$) δ ppm: 7.70 (br. s, 1H), 7.32-7.39 (m, 2H), 7.00-7.08 (m, 2H), 6.72 (d, 1H), 5.24 (s, 2H), 2.14 (s, 3H). [ES + MS] m/z 268 MH$^+$). |
| 12 | 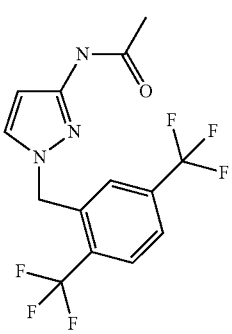 [SMILES: CC(=O)Nc1ccn(Cc2cc(C(F)(F)F)ccc2C(F)(F)F)n1] | JRD | $^1$H NMR (300 MHz, DMSO-d$_6$) δ ppm: 10.44 (br. s, 1H), 7.91-8.05 (m, 2H), 7.80 (d, 1H), 7.28 ( br. s, 1H), 6.56 (d, 1H), 5.52 (s, 2H), 1.96 (s, 3H). [ES + MS] m/z 352 MH$^+$). |
| 13 | 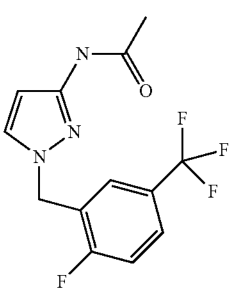 [SMILES: CC(=O)Nc1ccn(Cc2cc(C(F)(F)F)ccc2F)n1] | ALFAAESAR | $^1$H NMR (300 MHz, DMSO-d$_6$) δ ppm: 10.44 (br. s, 1H), 7.83-7.88 (m, 1H), 7.78 (d, 1H), 7.35-7.41 (m, 1H), 6.66-6.69 (m, 1H), 6.55 (d, 1H), 5.43 (s, 2H) 1.96 (s, 3H). [ES + MS] m/z 302 MH$^+$). |

TABLE A-continued

| Int. | Structure | Benzyl bromide | Physical data |
|---|---|---|---|
| 14 | 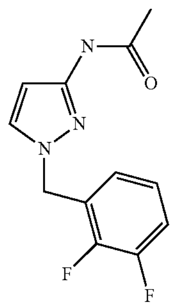 [SMILES: CC(=O)Nc1ccn(Cc2cccc(F)c2F)n1] | ALDRICH | $^1$H NMR (300 MHz, DMSO-d$_6$) δ ppm: 10.41 (br. s, 1H), 7.73 (d, 1H), 7.34-7.43 (m, 1H), 7.15-7.22 (m, 1H), 6.98-7.03 (m, 1H), 6.47 (d, 1H), 5.31 (s, 2H) 1.94 (s, 3H). [ES + MS] m/z 252 MH$^+$). |
| 15 | 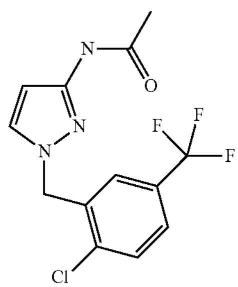 [SMILES: CC(=O)Nc1ccn(Cc2cc(C(F)(F)F)ccc2Cl)n1] | ALFAAESAR | $^1$H NMR (300 MHz, DMSO-d$_6$) δ ppm: 10.43 (br. s, 1H), 7.78 (d, 1H), 7.74 (m, 2H), 7.43 (br. s, 1H), 6.52 (d, 1H), 5.41 (s, 2H), 1.95 (s, 3H). [ES + MS] m/z 318 MH$^+$). |
| 16 | 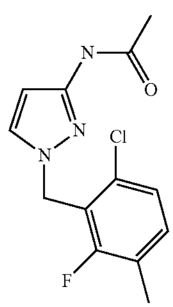 [SMILES: CC(=O)Nc1ccn(Cc2c(Cl)ccc(C)c2F)n1] | FLUOROCHEM | $^1$H NMR (300 MHz, DMSO-d$_6$) δ ppm: 10.38 (br. s, 1H), 7.66 (d, 1H), 7.23-7.34 (m, 2H), 6.43 (d, 1H), 5.31 (d, 2H), 2.22 (d, 3H), 1.92 (s, 3H), [ES + MS] m/z 282 MH$^+$). |
| 17 | 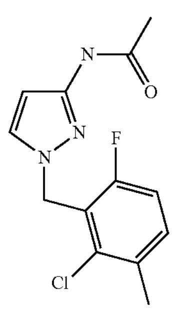 [SMILES: CC(=O)Nc1ccn(Cc2c(F)ccc(C)c2Cl)n1] | FLUOROCHEM | $^1$H NMR (300 MHz, DMSO-d$_6$) δ ppm: 10.37 (br. s, 1H), 7.67 (d, 1H), 7.38-7.43 (m, 1H), 7.16-7.22 (m, 1H), 6.43 (d, 1H), 5.34 (d, 2H), 2.31 (s, 3H), 1.92 (s, 3H), [ES + MS] m/z 282 MH$^+$). |
| 18 | 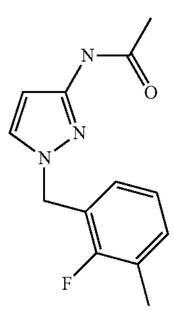 [SMILES: CC(=O)Nc1ccn(Cc2cccc(C)c2F)n1] | ALFAAESAR | $^1$H NMR (300 MHz, DMSO-d$_6$) δ ppm: 10.39 (br. s, 1H), 7.68 (d, 1H), 7.20-7.25 (m, 1H), 6.97-7.07 (m, 2H), 6.45 (d, 1H), 5.23 (br. s, 2H), 2.22 (d, 3H), 1.94 (s, 3H). [ES + MS] m/z 248 (MH$^+$). |

TABLE A-continued
| Int. | Structure | Benzyl bromide | Physical data |
|---|---|---|---|
| 19 | 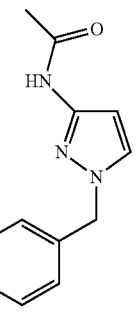 | 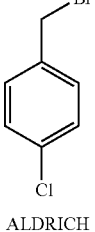  ALDRICH | $^1$H NMR (300 MHz, CDCl$_3$) δ ppm:: 10.37 (s, 1H), 7.69 (d, 1H), 7.38 (d, 2H), 7.19 (d, 2H), 6.46 (d, 2H), 1.93 (s, 3H); [ES + MS] m/z: 250 (MH$^+$). |
| 21 | 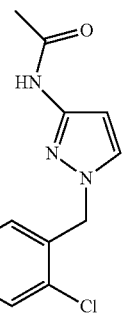 | 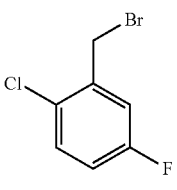  ALDRICH | $^1$H NMR (300 MHz, CDCl$_3$) δ ppm:: 7.80 (s, 1H), 7.39 (d, 1H), 7.35 (dd, 1H), 6.96 (m, 1H), 6.76 (d, 1H), 6.62 (dd, 1H), 5.26 (s, 2H), 2.15 (s, 3H); [ES + MS] m/z: 268 (MH+). |
| 22 | 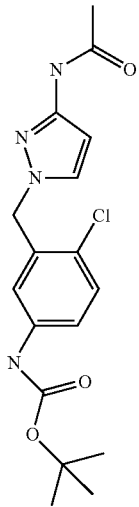 [SMILES: CC(=O)Nc1ccn(Cc2cc(NC(=O)OC(C)(C)C)ccc2Cl)n1] | Intermediate 4  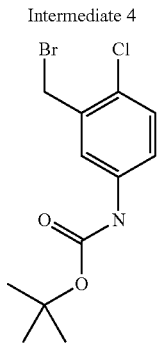 | $^1$H NMR (300 MHz, DMSO-d$_6$) δ ppm: 10.42 (br. s, 1H), 9.51 (br. s, 1H), 7.68 (d, 1H), 7.26-7.50 (m, 3H), 6.47 (d, 1H), 5.23 (br. s, 2H), 1.95 (s, 3H), 1.45 (s, 9H). [ES + MS] m/z 365 [MH$^+$] |

TABLE A-continued

| Int. | Structure | Benzyl bromide | Physical data |
|---|---|---|---|
| 23 | 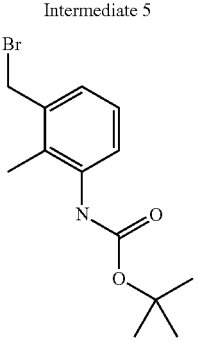 | Intermediate 5 | $^1$H NMR (300 MHz, DMSO-d$_6$) δ ppm: 10.37 (br. s, 1H), 8.60 (br. s, 1H), 7.60 (d, 1H), 7.17-7.20 (m, 1H), 7.06-7.11 (m, 1H), 6.77-6.80 (m, 1H), 6.46 (d, 1H), 5.21 (br. s, 2H), 2.10 (s, 3H), 1.95 (s, 3H), 1.44 (s, 9H), . [ES + MS] m/z 345 [MH$^+$] |
| 24 | 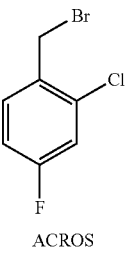 | ACROS | $^1$H NMR (300 MHz, DMSO-d$_6$) δ ppm: 10.41 (br. s, 1H), 7.71 (d, 1H), 7.46-7.50 (m, 1H), 7.19-7.26 (m, 1H), 7.10-7.15 (m, 1H), 6.49 (d, 1H), 5.29 (s, 2H), 1.96 (s, 3H) . [ES + MS] m/z 253 (MH+) |
| 25 | 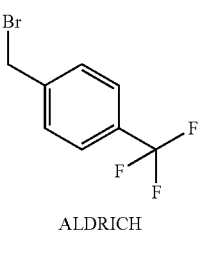 [SMILES: FC(F)(F)c1ccc(CBr)cc1] | ALDRICH | $^1$H NMR (300 MHz, DMSO-d$_6$) δ ppm: 10.39 (s, 1H), 7.74 (d, 1H), 7.69 (d, 2H), 7.35 (d, 2H), 7.08 (m, 1H), 6.48 (d, 1H), 5.31 (s, 2H), 1.94 (s, 3H). [ES + MS] m/z 284 (MH+). |

Intermediate 20

N-{1-[(2,6-difluorophenyl)methyl]-1H-pyrazol-3-yl}acetamide

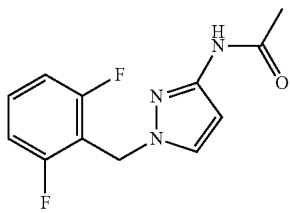 [SMILES: CC(=O)Nc1ccn(Cc2c(F)cccc2F)n1]

Intermediate 1 (300 mg; 2.398 mmol) was dissolved in 3 mL of anhydrous DMF, at 0° C., then NaH (96 mg, 2.4 mmol) was added and reaction mixture was left stirring in the same conditions of temperature during 20 min, after that time 2,6-difluorobenzyl bromide (496 mg, 2.4 mmol) was added dropwise, previously dissolved in 2 ml of anhydrous DMF. Reaction was left in the same conditions reaching room temperature for 20 h. Then reaction mixture was diluted with AcOEt and NH$_4$Cl. Phases were separated and organic phase was washed with brine. Organic phase was dried over MgSO$_4$, filtered and concentrated to dryness under vacuum. Crude was purified by chromatography on silica gel using a Hex/EtOAc gradient (0%-70%). Appropriate fractions were combined and evaporated to yield title compound as a white solid (377 mg; 63%). $^1$H NMR (300 MHz, DMSO-d$_6$) δ ppm: 10.39 (br s, 1H), 7.66 (d, 1H), 7.39-7.49 (m, 1H), 7.07-7.15 (m, 2H), 6.43 (d, 1H), 5.25 (s, 2H), 1.91 (s, 3H). [ES+MS] m/z 252 (MH$^+$).

Method B

Intermediate 26

N-{1-[(2-fluorophenyl)methyl]-1H-pyrazol-3-yl}acetamida

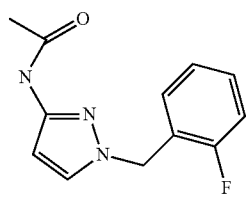 [SMILES: CC(=O)Nc1ccn(Cc2ccccc2F)n1]

To a solution of Intermediate 1 (200 mg, 1.598 mmol) in 10 mL of ACN, under $N_2$(g) atmosphere, was added $K_2CO_3$ (Aldrich, 331 mg, 2.398 mmol) and 1-(bromomethyl)-2-fluorobenzene (Aldrich, 302 mg, 1.598 mmol). Mixture of reaction was stirred and heated to reflux during one hour. Solvent was removed, and crude was partitioned between EtOAc and brine, organic layer was dried over $Na_2SO_4$ (anh) and filtered. EtOAc was evaporated under vacuum conditions. Residue was purified by Si(II) chromatography cartridge using Hex:EtOAc mixtures as eluents to yield the title compound (123 mg, 0.527 mmol, 33%). $^1$H NMR (300 MHz, $CDCl_3$) δ ppm: 7.72 (br,s, 1H), 7.33-7.37 (m, 3H), 7.17-7.20 (m, 2H), 6.70 (d, 1H), 5.18 (s, 2H), 2.13 (s, 3H). [ES+MS] m/z 234 (MH+).

Intermediate 27

2-(1H-pyrazol-3-yl)-1H-isoindole-1,3(2H)-dione

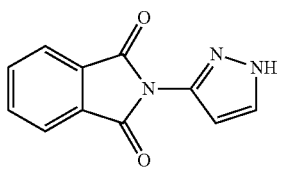 [SMILES: O=C1c2ccccc2C(=O)N1c1cc[nH]n1]

In a 500 mL round-bottom flask a mixture of 3-aminopyrazole (Aldrich, 10 g, 120 mmol) and phthalic anhydride (Aldrich, 24.96 g, 168 mmol) in 1,4-dioxane (150 mL) was stirred at reflux for 17 hours. The reaction was allowed to reach room temperature and solvent was evaporated to dryness. Residue was washed with EtOH and a yellowish solid was filtered to afford 23.6 g (yield 92%) of the title compound. $^1$H NMR (300 MHz, DMSO-$d_6$) δ ppm: 13.09 (br s, 1H), 7.89-7.98 (m, 4H), 7.86 (br s, 1H), 6.36 (d, 1H). [ES+MS] m/z 214 (MH+).

Intermediate 28

2-(5-methyl-1H-pyrazol-3-yl)-1H-isoindole-1,3(2H)-dione

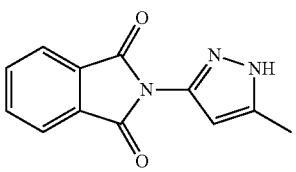 [SMILES: Cc1cc(N2C(=O)c3ccccc3C2=O)n[nH]1]

In a 100 mL round-bottom flask a mixture of 5-methyl-1H-pyrazol-3-amine (Aldrich, 500 mg, 5.15 mmol) and phthalic anhydride (ALDRICH) (1.07 g, 7.21 mmol) in 1,4-dioxane (30 mL) was stirred at reflux for 25 hours. Reaction was allowed to reach room temperature and the formed precipitate was filtered and washed with EtOH to afford 589 mg of the title compound as a yellowish solid. Filtrate was evaporated to dryness and after washing the residue with EtOH, an additional batch of 331 mg was obtained (total yield: 79%). $^1$H NMR (300 MHz, DMSO-$d_6$) δ ppm: 12.77 (br s, 1H), 7.87-7.98 (m, 4H), 6.09 (s, 1H), 2.28 (s, 3H). [ES+MS] m/z 228 (MH+).

Intermediate 29

2-{1-[(3-chloro-2-fluorophenyl)methyl]-1H-pyrazol-3-yl}-1H-isoindole-1,3(2H)-dione

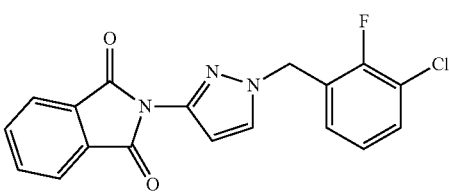 [SMILES: O=C1c2ccccc2C(=O)N1c1ccn(Cc2cccc(Cl)c2F)n1]

In a 100 mL round-bottom flask a mixture of Intermediate 27 (2-(1H-pyrazol-3-yl)-1H-isoindole-1,3(2H)-dione, 500 mg, 2.345 mmol), 1-(bromomethyl)-3-chloro-2-fluoro-benzene (ALFAAESAR, 629 mg, 2.81 mmol), and potassium carbonate (ALDRICH) (389 mg, 2.81 mmol) in acetonitrile (20 mL) was stirred at reflux for 4 hours. 0.5 eq (262 mg) more of 1-(bromomethyl)-3-chloro-2-fluorobenzene (ALFAAESAR) were added and the reaction was stirred at reflux for 20 hours. Reaction was allowed to reach room temperature; potassium carbonate was filtered and was washed with DCM. The filtrate was evaporated to dryness to afford 887 mg of crude that was purified via silica gel chromatography with ethyl acetate/hexane gradient (8% to 70%) to separate the non-desired 2-{1-[(3-chloro-2-fluorophenyl)methyl]-1H-pyrazol-5-yl}-1H-isoindole-1,3(2H)-dione isomer. 452 mg (yield: 54%) of 2-{1-[(3-chloro-2-fluorophenyl)methyl]-1H-pyrazol-3-yl}-1H-isoindole-1,3(2H)-dione were obtained as white solid. $^1$H NMR (300 MHz, DMSO-$d_6$) δ ppm: 7.99 (d, 1H), 7.88-7.95 (m, 4H), 7.54-7.60 (m, 1H), 7.20-7.27 (m, 2H), 6.41 (d, 1H), 5.49 (s, 2H). [ES+MS] m/z 356 (MH+).

Intermediate 30

2-{1-[(2-fluoro-3-methylphenyl)methyl]-1H-pyrazol-3-yl}-1H-isoindole-1,3(2H)-dione

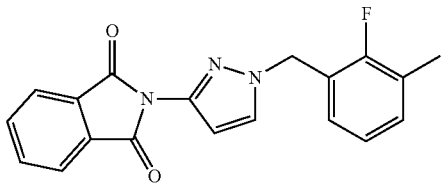 [SMILES: Cc1cccc(Cn2ccc(N3C(=O)c4ccccc4C3=O)n2)c1F]

1.00 g (4.69 mmol) of Intermediate 27 was dissolved in 15 mL of DMF (dry) at 0° C. 0.188 g of NaH (Aldrich, 4.69 mmol) were added to the solution and the mixture was stirred and kept at 0° C. for 30 min. To this mixture of reaction, was added dropwise a solution of 1-(bromomethyl)-2-fluoro-3-methylbenzene (ALFAAESAR, 953 mg, 4.69 mmol) in 5 mL DMF (dry), over a period of 2 min. The mixture was stirred at r.t. for 3 h. 1 eq more of 1-(bromomethyl)-2-fluoro-3-methylbenzene (953 mg, 4.69 mmoll) was added to the reaction and was heated to 80° C. 0.2 eq of NaH c.a. every 2 h until 0.8 eq were added. After 44 hours reaction was partitioned between NH4Cl (aq, sat) and EtOAc. Organic fraction was dried over MgSO4 (anh) and concentrated to dryness to yield 1.64 g of a crude that was purified three times by Si(II) chromatography with gradient Hex/EtOAc. 491 mg (yield: 31%) of 2-{1-[(2-fluoro-3-methylphenyl)methyl]-1H-pyrazol-3-yl}-1H-isoindole-1,3(2H)-dione were obtained as white solid. $^1$H NMR (300 MHz, DMSO-$d_6$) δ ppm: 7.88-7.96 (m, 5H), 7.23-7.28 (m, 1H), 7.07-7.11 (m, 2H), 6.39 (d, 1H), 5.40 (s, 2H), 2.24 (d, 3H). [ES+MS] m/z 336 (MH+).

Intermediate 31

2-[1-(phenylmethyl)-1H-pyrazol-3-yl]-1H-isoindole-1,3(2H)-dione

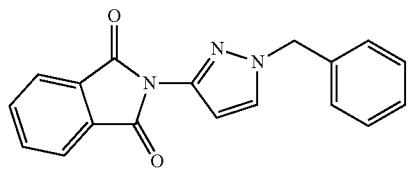 [SMILES: O=C1c2ccccc2C(=O)N1c1ccn(Cc2ccccc2)n1]

The title compound was prepared following the procedure described above for Intermediate 30, using benzyl bromide (Aldrich, 401 mg, 2.345 mmol) and Intermediate 27 (500 mg, 2.345 mmol) as starting materials. 262 mg (yield: 37%) of 2-[1-(phenylmethyl)-1H-pyrazol-3-yl]-1H-isoindole-1,3(2H)-dione were obtained as white solid. $^1$H NMR (300 MHz, DMSO-$d_6$) δ ppm: 7.89-7.98 (m, 5H), 7.29-7.40 (m, 5H), 6.39 (d, 1H), 5.38 (s, 2H). [ES+MS] m/z 304 (MH+).

Intermediate 32

2-{1-[(2-chloro-6-fluorophenyl)methyl]-5-methyl-1H-pyrazol-3-yl}-1H-isoindole-1,3(2H)-dione

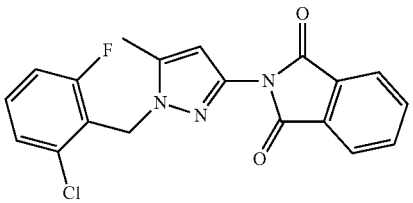 [SMILES: Cc1cc(N2C(=O)c3ccccc3C2=O)nn1Cc1c(F)cccc1Cl]

In a 100 mL round-bottom flask a mixture of 2-(bromomethyl)-1-chloro-3-fluorobenzene (Aldrich, 0.427 mL, 3.11 mmol), Intermediate 28 (589 mg, 2.59 mmol) and potassium carbonate (Aldrich, 430 mg, 3.11 mmol) in ACN (40 mL) was stirred at reflux for 20 h. Reaction was allowed to reach room temperature; potassium carbonate was filtered and was washed with DCM. The filtrate was evaporated to dryness to afford 1.03 g of crude that was purified via silica gel chromatography with Hex/EtOAc gradient (10%-80%-100%) to separate the non-desired isomer (2-{1-[(2-chloro-6-fluorophenyl)methyl]-3-methyl-1H-pyrazol-5-yl}-1H-isoindole-1,3(2H)-dione). 314 mg (yield 33%) of the title compound were obtained. $^1$H NMR (300 MHz, DMSO-$d_6$) δ ppm: 7.85-7.93 (m, 4H), 7.25-7.48 (m, 3H), 6.15 (s, 1H), 5.36 (d, 2H), 2.43 (s, 3H). [ES+MS] m/z 370 (MH+).

Intermediate 33

1-[(3-chloro-2-fluorophenyl)methyl]-1H-ppyrazol-3-amine

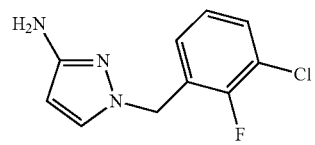 [SMILES: Nc1ccn(Cc2cccc(Cl)c2F)n1]

In a 50 mL round-bottom flask Intermediate 29 (532 mg, 1.495 mmol) was dissolved in ethanol (20 mL) and hydrazine monohydrate (FLUKA) (0.363 mL, 7.48 mmol) was added. Mixture was stirred at 80° C. for 16 hours. The white precipitate was filtered and washed with ethanol. Filtrate was evaporated to dryness to afford 530 mg of crude that was purified in silica chromatography with gradient DCM/MeOH (1%-10%-20%). 337 mg (yield: quantitative) of 1-[(3-chloro-2-fluorophenyl)methyl]-1H-pyrazol-3-amine were obtained as white solid. $^1$H NMR (300 MHz, DMSO-$d_6$) δ ppm: 7.47-

7.53 (m, 1H), 7.44 (d, 1H), 7.15-7.20 (m, 1H), 7.05-7.10 (m, 1H), 5.41 (d, 1H), 5.11 (s, 2H), 4.60 (br s, 2H). [ES+MS] m/z 226 (MH$^+$).

Intermediate 34

1-[(2-fluoro-3-methylphenyl)methyl]-1H-pyazol-3-amine

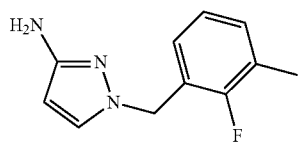

The title compound was prepared following the procedure described above for Intermediate 33, using Intermediate 30 (677 mg, 2.019 mmol) as starting material. 340 mg (yield: 82%) of 1-[(2-fluoro-3-methylphenyl)methyl]-1H-pyrazol-3-amine were obtained as orange syrup. $^1$H NMR (300 MHz, DMSO-d$_6$) δ ppm: 7.39 (d, 1H), 7.16-7.21 (m, 1H), 6.99-7.04 (m, 1H), 6.89-6.94 (m, 1H), 5.39 (d, 1H), 5.04 (s, 2H), 4.56 (br s, 2H), 2.22 (d, 3H). [ES+MS] m/z 206 (MH$^+$).

Intermediate 35

1-(phenylmethyl)-1H-pyrazol-3-amine

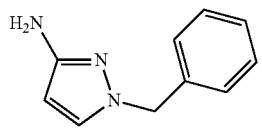 [SMILES: Nc1ccn(Cc2ccccc2)n1]

The title compound was prepared following the procedure described above for Intermediate 33, using Intermediate 31 (262 mg, 0.864 mmol) as starting material. 140 mg (yield: 94%) of 1-(phenylmethyl)-1H-pyrazol-3-amine were obtained. $^1$H NMR (300 MHz, DMSO-d$_6$) 5 ppm: 7.42 (d, 1H), 7.16-7.33 (m, 5H), 5.40 (d, 1H), 5.02 (s, 2H), 4.55 (br s, 2H). [ES+MS] m/z 174 (MH$^+$).

Intermediate 36

1-[(2-chloro-6-fluorophenyl)methyl]-5-methyl-1H-pyrazol-3-amine

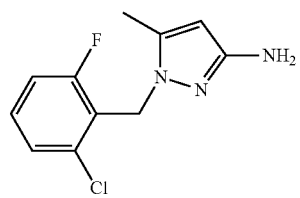 [SMILES: Cc1cc(N)nn1Cc1c(F)cccc1Cl]

In a 100 mL round-bottom flask Intermediate 32 (314 mg, 0.849 mmol) was dissolved in EtOH (40 mL) and hydrazine monohydrate (Aldrich, 0.095 mL, 1.953 mmol) was added. Mixture was stirred at room temperature for 50 hours. The white precipitate was filtered and washed with EtOH. Filtrate was evaporated to dryness to afford 330 mg of crude that was purified in silica chromatography with gradient DCM/MeOH (0%-6%-20%). 148 mg (yield 73%) of 1-[(2-chloro-6-fluorophenyl)methyl]-5-methyl-1H-pyrazol-3-amine were obtained. $^1$H NMR (300 MHz, DMSO-d$_6$) δ ppm: 7.18-7.42 (m, 3H), 5.18 (s, 1H), 5.01-5.02 (m, 2H), 4.41 (br s, 2H), 2.23 (s, 3H). [ES+MS] m/z 240 (MH$^+$).

Intermediate 37

1-[(2-chloro-6-fluorophenyl)methyl]-1H-pyrazol-3-amine

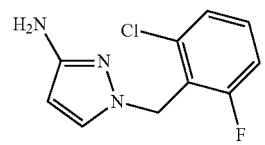 [SMILES: Nc1ccn(Cc2c(F)cccc2Cl)n1]

Intermediate 6 (4 g, 15 mmol.) was dissolved in a mixture of EtOH (30 mL) and a 25% aq. Solution of NaOH (37.5 mL). The mixture was heated to reflux overnight. The EtOH was then evaporated off and the remaining aqueous fraction was partitioned between sat. aq. NaCl (50 mL) and EtOAc (50 mL). The aqueous fractioned was extracted with EtOAc (3×50 mL) and the resulting organic layer was dried over Na$_2$SO$_4$ and concentrated to dryness to give 1-[(2-chloro-6-fluorophenyl)methyl]-1H-pyrazol-3-amine (3.28 g, 14.6 mmol., 97%) as a yellow crystalline solid. $^1$H NMR (300 MHz, CDCl$_3$) δ ppm: 7.17-7.30 (m, 3H), 7.04 (m, 1H), 5.56 (d, 1H), 5.27 (d, 2H), 3.61 (br s, 2H); 210 (s, 3H) [ES+MS] m/z: 226.

Intermediates 38-54 were prepared by a method analogous to that described for Intermediate 37 but replacing corresponding Intermediate 6 (the acetyl intermediate) with the Intermediate indicated in Table B.

TABLE B

| Int. | Structure | Acetyl intermediate to replace Int. 6 | Physical data |
|---|---|---|---|
| 38 | pyrazol-NH2, N-CH2-(2,5-dichlorophenyl) | 7 | $^1$H NMR (300 MHz, DMSO-d$_6$) δ ppm: 7.48-7.51 (m, 2H), 7.36-7.41 (m, 1H), 6.89 (d, 1H), 5.46 (d, 1H), 5.13 (s, 2H), 4.69 (br. s, 2H). [ES + MS] m/z 243 (MH$^+$). |
| 39 | pyrazol-NH2, N-CH2-(2-methylphenyl) | 8 | $^1$H NMR (300 MHz, DMSO-d$_6$) δ ppm: 7.32 (d, 1H), 7.09-7.17 (m, 3H), 6.89-6.91 (m, 1H), 5.41 (d, 1H), 5.02 (s, 2H), 4.5 (br. s, 2H), 2.27 (s, 3H). [ES + MS] m/z 188 (MH$^+$). |
| 40 | pyrazol-NH2, N-CH2-(2-bromophenyl) | 9 | $^1$H NMR (300 MHz, DMSO-d$_6$) δ ppm: 7.60-7.63 (m, 1H), 7.45 (d, 1H), 7.30-7.36 (m, 1H), 7.19-7.25 (m, 1H), 6.85-6.88 (m, 1H), 5.45 (d, 1H), 5.10 (s, 2H), 4.62 (br. s, 2H). [ES + MS] m/z 253 (MH$^+$). |
| 41 | pyrazol-NH2, N-CH2-(2-trifluoromethylphenyl) | 10 | $^1$H NMR (300 MHz, DMSO-d$_6$) δ ppm: 7.72-7.74 (m, 1H), 7.58-7.63 (m, 1H), 7.45-7.50 (m, 2H), 6.86-6.89 (m, 1H), 5.47 (d, 1H), 5.24 (s, 2H), 4.66 (br. s, 2H). [ES + MS] m/z 242 (MH$^+$). |
| 42 | pyrazol-NH2, N-CH2-(2-fluoro-3-chlorophenyl) | 11 | $^1$H NMR (300 MHz, DMSO-d$_6$) δ ppm: 7.49-7.54 (m, 1H), 7.45 (d, 1H), 7.16-7.21 (m, 1H), 7.06-7.11 (m, 1H), 5.41 (d, 1H), 5.12 (br. s, 2H), 4.62 (br. s, 2H). [ES MS] m/z 226 (MH$^+$). |

TABLE B-continued

| Int. | Structure | Acetyl intermediate to replace Int. 6 | Physical data |
|---|---|---|---|
| 43 | pyrazole-N-CH2-[2,5-bis(trifluoromethyl)phenyl] with 3-NH2 | 12 | ¹H NMR (300 MHz, DMSO-d₆) δ ppm: 7.87-8.02 (m, 2H), 7.55 (d, 1H), 7.11 (br, s, 1H), 5.51 (d, 1H), 5.34 (br. s, 2H), 4.74 (br. s, 2H). [ES + MS] m/z 310 (MH⁺). |
| 44 | pyrazole-N-CH2-[5-fluoro-2-(trifluoromethyl)phenyl] with 3-NH2  See footnote (a) | 13 | ¹H NMR (300 MHz, DMSO-d₆) δ ppm: 7.79-7.84 (m, 1H), 7.52 (d, 1H), 7.32-7.36 (m, 1H), 6.53-6.55 (m, 1H), 5.50 (d, 1H), 5.26 (br. s, 2H), 4.76 (br. s, 2H). [ES + MS] m/z 260 (MH⁺). |
| 45 | pyrazole-N-CH2-(2,3-difluorophenyl) with 3-NH2 | 14 | ¹H NMR (300 MHz, DMSO-d₆) δ ppm: 7.45 (d, 1H), 7.30-7.39 (m, 1H), 7-12-7.20 (m, 1H), 6.92-6.96 (m, 1H), 5.41 (d, 1H), 5.13 (br. s, 2H), 4.61 (br. s, 2H). [ES MS] m/z 210 (MH⁺). |
| 46 | pyrazole-N-CH2-[2-chloro-5-(trifluoromethyl)phenyl] with 3-NH2 | 15 | ¹H NMR (300 MHz, DMSO-d₆) δ ppm: 7.67-7.74 (m, 2H), 7.51 (d, 1H), 7.22 (br. s, 1H), 5.46 (d, 1H), 5.22 (br. s, 2H), 4.69 (br. s, 2H). [ES + MS] m/z 276 (MH⁺). |
| 47 | pyrazole-N-CH2-(2-chloro-6-fluoro-3-methylphenyl) with 3-NH2 | 16 | ¹H NMR (300 MHz, DMSO-d₆) δ ppm: 7.34 (d, 1H), 7.21-7.32 (m, 2H), 5.35 (d, 1H), 5.13 (d, 2H), 4.57 (br. s, 2H), 2.21 (d, 3H). [ES + MS] m/z 240 (MH⁺). |

TABLE B-continued

| Int. | Structure | Acetyl intermediate to replace Int. 6 | Physical data |
|---|---|---|---|
| 48 | (3-aminopyrazole N-benzyl with 2-Cl, 6-F, 3-methyl phenyl) | 17 | $^1$H NMR (300 MHz, DMSO-d$_6$) δ ppm: 7.35-7.41 (m, 2H), 7.13-7.19 (m, 1H), 5.35 (d, 1H), 5.15 (d, 2H), 4.56 (br. s, 2H), 2.30 (s, 3H). [ES MS] m/z 240 (MH$^+$). |
| 49 | (3-aminopyrazole N-benzyl with 2-F, 3-methyl phenyl) | 18 | $^1$H NMR (300 MHz, DMSO-d$_6$) δ ppm: 7.40 (d, 1H), 7.17-7.22 (m, 1H), 7.00-7.05 (m, 1H), 6.90-6.95 (m, 1H), 5.40 (d, 1H), 5.05 (br. s, 2H), 4.57 (br. s, 2H), 2.22 (d, 3H). [ES + MS] m/z 206 (MH$^+$). |
| 50 | (3-aminopyrazole N-benzyl with 4-Cl phenyl) | 19 | $^1$H NMR (300 MHz, CDCl$_3$) δ ppm: 7.26-7.32 (m, 2H), 7.15 (d, 1H), 7.12 (m, 2H), 5.63 (d, 1H), 5.07 (s, 2H), 3.65 (br s, 2H); [ES + MS] m/z: 208. |
| 52 | (3-aminopyrazole N-benzyl with 2-F phenyl) | 26 | $^1$H NMR (300 MHz, DMSO-d$_6$) δ ppm: 7.41 (d, 1H), 7.29-7.37 (m, 1H), 7.08-7.21 (m, 3H), 5.40 (d, 1H), 5.08 (s, 2H), 4.58 (br. s, 2H). |
| 53 | (3-aminopyrazole N-benzyl with 2-Cl, 4-F phenyl) | 24 | $^1$H NMR (300 MHz, DMSO-d$_6$) δ ppm: 7.43-7.47 (m, 2H), 7.14-7.22 (m, 1H), 6.99-7.18 (m1H), 5.13 (d, 1H), 5.1 (s, 2H), 4.63 (br. S, 2H),. [ES + MS] m/z 226 (MH$^+$) |

TABLE B-continued

| Int. | Structure | Acetyl intermediate to replace Int. 6 | Physical data |
|---|---|---|---|
| 54 | 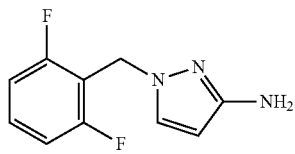 [SMILES: Nc1ccn(Cc2c(F)cccc2F)n1] | 25 | $^1$H NMR (300 MHz, CDCl$_3$-d$_6$) δ ppm: 7.58 (d, 2H), 7.28 (m, 1H), 7.20 (d, 1H), 5.66 (d, 1H), 5.16 (s, 2H), 3.67 (br. s, 2H). [ES + MS] m/z 242 (MH$^+$). |

(a) Purified by HPLC preparative using SunFire Chromatography Column, Method (40_00) ACN/H2O, in neutral conditions

Intermediate 51

1-[(2,6-difluorophenyl)methyl]-1H-pyrazol-3-amine

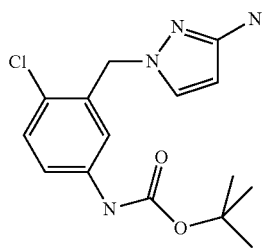 [SMILES: CC(C)(C)OC(=O)Nc1ccc(Cl)c(Cn2ccc(N)n2)c1]

Intermediate 20 (370 mg, 1.473 mmol) was dissolved in EtOH (10 mL) and NaOH (aq 25%, 62.5 mmol) (10 mL) was added. The mixture was heated to 75° C. for 16 hours. Then, ethanol was evaporated under vacuum, and aqueous fraction was partitioned between distilled water and EtOAc. Aqueous layer was extracted with EtOAc (×3) and DCM (×1); organic layers were combined and dried over MgSO$_4$ and concentrated to dryness to give a yellowish solid. It was purified by chromatography on silica gel using a DCM/MeOH gradient (0%-10%). Appropriate fractions were combined and evaporated to yield title compound as an orange solid (174 mg; 57%). $^1$H NMR (300 MHz, DMSO-d$_6$) δ ppm: 7.35-7.46 (m, 2H), 7.05-7.14 (m, 2H), 5.36 (d, 1H), 5.07 (s, 2H), 4.67 (br s, 2H). [ES+MS] m/z 210 (MH$^+$).

Intermediate 55

1,1-dimethylethyl {3-[(3-amino-1H-pyrazol-1-yl)methyl]-4-chlorophenyl}carbamate

A solution of Intermediate 22 (129 mg, 0.354 mmol) in EtOH (10 mL) and NaOH (aq, 12%) (10 mL) was heated to 50° C. during 4 hours. At that time reaction was not totally completed but it was stopped. Amine group was starting to lose its protecting group Boc. EtOH was evaporated under vacuum, aqueous fraction was partitioned between saturated brine and EtOAc. Aqueous layer was extracted with EtOAc. Combined organic layers were dried over MgSO$_4$ anhydrous, and concentrated to dryness to yield the title compound (83 mg, 72.7%) $^1$H NMR (300 MHz, DMSO-d$_6$) δ ppm: 9.49 (br.s, 1H), 7.25-7.39 (m, 4H), 5.42 (d, 1H), 5.04 (d, 1H), 4.58 (s, 2H), 1.44 (s, 9H). [ES+MS] m/z 323 [MH$^+$].

Intermediate 56

1,1-dimethylethyl {3-[(3-amino-1H-pyrazol-1-yl)methyl]-2-methylphenyl}carbamate

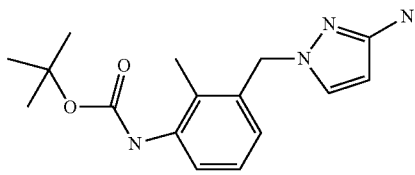 [SMILES: Cc1c(Cn2ccc(N)n2)cccc1NC(=O)OC(C)(C)C]

A solution of Intermediate 23 (185 mg, 0.537 mmol) in EtOH (5 mL) and NaOH (aq, 12%) (5 mL) was heated to 75° C. during 2 h. During 3 h reaction was heated to 50° C. 5 ml of NaOH (12%,aq) were added and reaction was heated at 100° C. during 3 h. Reaction mixture was kept in the fridge overnight. Next morning it was heated again during 1 h at 75° C., after being stirred 2 h. at room temperature. At that time reaction was not completed but protecting group Boc was disappearing so reaction was stopped. EtOH was evaporated under vacuum; aqueous solution was extracted with EtOAc (×3). Organic layers were dried over MgSO$_4$ anhydrous, and concentrated to dryness giving a yellow solid. Solid was purified by chromatography column Si(II) 10 g, using a mixture of DCM/MeOH as eluent. 1,1-dimethylethyl {3-[(3-amino-1H-pyrazol-1-yl)methyl]-2-methylphenyl}carbamate (64 mg, 0.201 mmol, 37%) was obtained as a white solid. $^1$H NMR (300 MHz, DMSO-d$_6$) δ ppm: 8.58 (br.s, 1H), 7.30 (d, 1H), 7.15-7.17 (m, 1H), 7.04-7.09 (m, 1H), 6.71-6.74 (m, 1H), 5.40 (d, 1H), 5.03 (br.s, 2H), 4.54 (s, 2H), 2.10 (s, 3H), 1.44 (s, 9H). [ES+MS] m/z 303 (MH⁺).

Intermediate 57

1-[(2-chloro-6-fluorophenyl)methyl]-3-isothiocyanato-1H-pyrazole

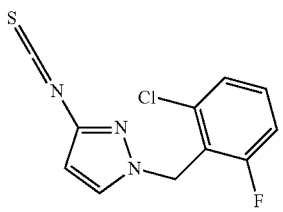 [SMILES: Fc1cccc(Cl)c1Cn1ccc(N=CC=S)n1]

To a solution of Intermediate 37 (1 g, 4.4 mmol.) in chloroform (60 mL), saturated aqueous NaHCO₃ (60 mL) was added followed by thiophosgene (0.76 g, 6.6 mmol.). The mixture was stirred vigorously overnight and the organic layer was separated off by means of a hydrophobic frit. The organic fraction was concentrated to dryness to give 1-[(2-chloro-6-fluorophenyl)methyl]-3-isothiocyanato-1H-pyrazole (1.1 g, 4.1 mmol, 93%) as a yellow solid. ¹H NMR (300 MHz, CDCl₃) δ ppm:: 7.24-7.36 (m, 3H), 7.07 (t, 1H), 6.16 (d, 1H), 5.39 (d, 2H); 210 (s, 3H) EM⁺(M/Z): 268.

Intermediates 58-76 were prepared by method analogous to that described for Intermediate 57 but replacing the Intermediate 37 with that indicated in Table C. The solvent used in the synthesis of these intermediates was DCM instead of chloroform.

TABLE C

| Int | Structure | Starting intermediate to replace Int. 37 | Physical data |
|---|---|---|---|
| 58 | 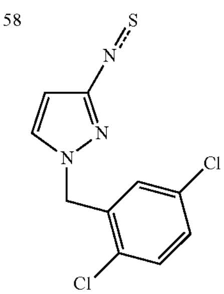 | 38 | ¹H NMR (300 MHz, DMSO-d₆) δ ppm: 7.96 (d, 1H), 7.53-7.56 (m, 1H), 7.45-7.48 (m, 1H), 7.21 (d, 1H), 6.49 (d, 1H), 5.40 (s, 2H). [MS] m/z 285 (MH⁺) |
| 59 | 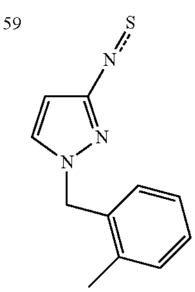 | 39 | ¹H NMR (300 MHz, DMSO-d₆) δ ppm: 7.86 (d, 1H), 7.17-7.23 (m, 3H), 6.97-6.99 (m, 1H), 6.46 (d, 1H), 5.30 (s, 2H), 2.28 (s, 3H). [ES + MS] m/z 230 [MH⁺] |
| 60 | 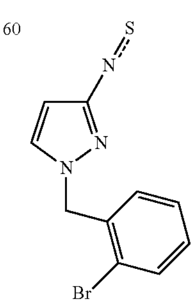 | 40 | ¹H NMR (300 MHz, DMSO-d₆) δ ppm: . 7.93 (d, 1H), 7.65-7.68 (m, 1H), 7.36-7.41 (m, 1H), 7.26-7.32 (m, 1H), 7.02-7.05 (m, 1H), 6.48 (d, 1H), 5.38 (s, 2H). [ES + MS] m/z 295 [MH⁺] |

TABLE C-continued

| Int | Structure | Starting intermediate to replace Int. 37 | Physical data |
|---|---|---|---|
| 61 | (pyrazole-N-CH2-phenyl-2-CF3, with N=S=S at pyrazole 3-position) | 54 | ¹H NMR (300 MHz, DMSO-$d_6$) δ ppm: 5.50 (s, 2H), 6.51 (d, 1H), 7.01-7.04 (m, 1H), 7.52-7.57 (m, 1H), 7.64-7.69 (m, 1H), 7.77-7.80 (m, 1H), 7.96 (d, 1H) [ES + MS] m/z 284 (MH⁺) |
| 62 | (pyrazole-N-CH2-phenyl-2-F-3-Cl) From 33-see notes (a) & (b) | 33 or 42 | ¹H NMR (300 MHz, DMSO-$d_6$) δ, ppm: 5.40 (d, 2H), 6.46 (d, 1H), 7.19-7.27 (m, 2H), 7.55-7.61 (m, 1H), 7.96 (d, 1H) [ES + MS] m/z 268 (MH⁺) |
| 63 | (pyrazole-N-CH2-phenyl-2,5-bis-CF3) | 43 | ¹H NMR (300 MHz, DMSO-$d_6$) δ ppm: 5.60 (s, 2H), 6.53 (d, 1H), 7.46 (br. s, 1H), 7.96-8.01 (m, 3H). |
| 64 | (pyrazole-N-CH2-phenyl-3-F-2-CF3) | 44 | ¹H NMR (300 MHz, DMSO-$d_6$) δ ppm: 7.99 (d, 1H), 7.86-7.90 (m, 1H), 7.39-7.44 (m, 1H), 6.82-6.86 (m, 1H), 6.53 (d, 1H), 5.51 (br. s, 2H). |

TABLE C-continued

| Int | Structure | Starting intermediate to replace Int. 37 | Physical data |
|---|---|---|---|
| 65 | (3-isothiocyanato-pyrazole with 2,3-difluorobenzyl on N1) See footnote (b) | 45 | ¹H NMR (300 MHz, DMSO-d₆) δ ppm: 7.95 (d, 1H), 7.37-7.46 (m, 1H), 7.17-7.23 (m, 1H), 7.03-7.08 (m, 1H), 6.46 (d, 1H), 5.40 (s, 2H). [ES + MS] m/z 252 (MH⁺). |
| 66 | (3-isothiocyanato-pyrazole with 2-chloro-5-trifluoromethylbenzyl on N1) | 46 | ¹H NMR (300 MHz, DMSO-d₆) δ ppm: 7.99 (d, 1H), 7.76 (br. s, 2H), 7.57 (br. s, 1H), 6.49 (d, 1H), 5.50 (s, 2H). |
| 67 | (3-isothiocyanato-pyrazole with 2-chloro-6-fluoro-3-methylbenzyl on N1) | 47 | ¹H NMR (300 MHz, DMSO-d₆) δ ppm: 7.91 (d, 1H), 7.21-7.39 (m, 2H), 6.43 (d, 1H), 5.39 (s, 2H), 2.22 (d, 3H),. [ES + MS] m/z 282 [MH⁺] |
| 68 | (3-isothiocyanato-pyrazole with 2-chloro-6-fluoro-3-methylbenzyl on N1) | 48 | ¹H NMR (300 MHz, DMSO-d₆) δ ppm: 7.91 (d, 1H), 7.42-7.47 (m, 1H), 7.19-7.25 (m, 1H), 6.41 (d, 1H), 5.42 (s, 2H), 2.31 (s, 3H),. [ES + MS] m/z 282 [MH⁺] |

TABLE C-continued

| Int | Structure | Starting intermediate to replace Int. 37 | Physical data |
|---|---|---|---|
| 69 | 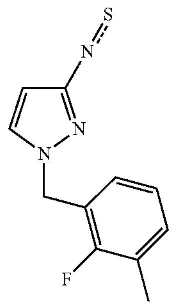 | 34 or 49 | $^1$H NMR (300 MHz, DMSO-d$_6$) δ ppm: 7.90 (d, 1H), 7.22-7.28 (m, 1H), 7.02-7.10 (m, 2H), 6.44 (d, 1H), 5.32 (s, 2H), 2.22 (d, 3H). [ES + MS] m/z 248 (MH$^+$). |
| 71 | 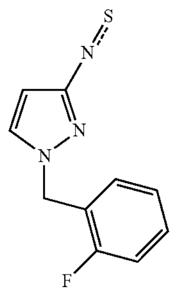 | 52 | $^1$H NMR (300 MHz, DMSO-d$_6$) δ ppm: 7.92 (d, 1H), 7.35-7.43 (m, 1H), 7.17-7.27 (m, 3H), 6.45 (d, 1H), 5.35 (s, 2H). [ES + MS] m/z 234 [MH$^+$] |
| 72 | 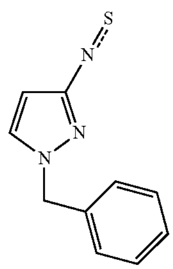 | 35 | $^1$H NMR (300 MHz, CDCl$_3$) δ ppm: 7.21-7.40 (m, 5H), 6.19 (d, 1H), 5.22 (s, 2H). [ES + MS] [MH$^+$] 216 |
| 73 | 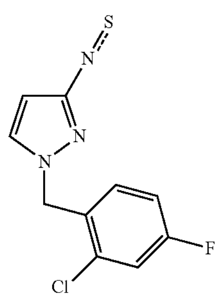 | 53 | $^1$H NMR (300 MHz, DMSO-d$_6$) δ ppm: 5.38 (s, 2H), 6.47 (d, 1H), 7.23-7.26 (m, 2H), 7.49-7.53 (m, 1H), 7.90 (d, 1H). |
| 74 | 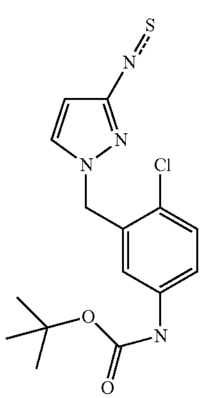 | 55 | $^1$H NMR (300 MHz, DMSO-d$_6$) δ ppm: 9.51 (br. s, 1H), 7.91 (d, 1H), 7.44-7.48 (m, 1H), 7.33-7.37 (m, 1H), 7.17 (m, 1H), 6.48 (d, 1H), 5.33 (s, 2H), 1.45 (s, 9H). [ES + MS] m/z 365 (MH$^+$) |

TABLE C-continued

| Int | Structure | Starting intermediate to replace Int. 37 | Physical data |
|---|---|---|---|
| 75 | 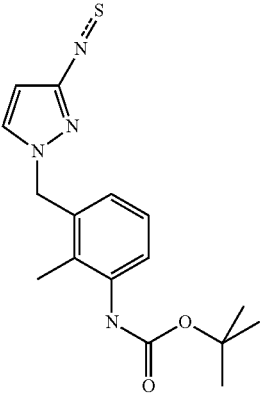 | 56 | $^1$H NMR (300 MHz, DMSO-$d_6$) δ ppm: 8.62 (br. s, 1H), 7.83 (d, 1H), 7.21-7.23 (m, 1H), 7.09-7.14 (m, 1H), 6.81-6.83 (m, 1H), 6.45 (d, 1H), 5.31 (s, 2H), 2.11 (s, 3H), 1.44 (s, 9H). [ES + MS] m/z 345 (MH$^+$) |
| 76 | 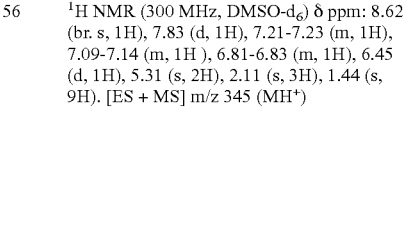 See footnote (a) | 36 | $^1$H NMR (300 MHz, DMSO-$d_6$) δ ppm: 7.25-7.49 (m, 3H), 6.23 (s, 1H), 5.28 (d, 2H), 2.37 (s, 3H). [ES + MS] m/z 282 (MH$^+$). |

(a) Organic phase was washed with water
(b) Crude was purified in silica gel cartridge with gradient Hex/ETOAc (0-10%)

Intermediate 70

1-[(2,6-difluorophenyl)methyl]-3-isothiocyanato-1H-pyrazole

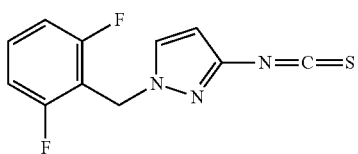 [SMILES: Fc1cccc(F)c1Cn1ccc(N=C=S)n1]

In a 50 mL round-bottom flask Intermediate 51 (162 mg, 0.774 mmol) was dissolved in aqueous sodium bicarbonate (7 mL) and dichloromethane (7 mL). Thiophosgene was added dropwise (0.071 mL, 0.929 mmol). The reaction was stirred at room temperature for 1 hour. Reaction mixture was diluted with DCM and aq. sodium bicarbonate. Phases were separated and organic layer was dried over MgSO$_4$, filtrated and concentrated to dryness under vacuum to give a brown solid (154 mg;). $^1$H NMR (300 MHz, DMSO-$d_6$) δ ppm: 7.91 (d, 1H), 7.43-7.53 (m, 1H), 7.10-7.18 (m, 2H), 6.42 (d, 1H), 5.35 (s, 2H). [ES+MS] m/z 252 (MH$^+$).

Intermediate 77

Ethyl 2-(3,5-dimethyl-1H-pyrazol-1-yl)propanoate

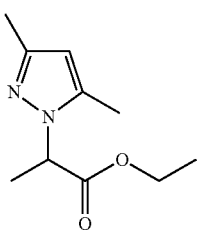

A suspension of 3,5-dimethyl-1H-pyrazole (Aldrich, 8 g, 0.083 mol), anhydrous K$_2$CO$_3$ (11.50 g, 0.083 mol) and ethyl 2-bromopropanoate (Aldrich, 15 g, 0.083 mol) in 50 mL of dry ACN was refluxed with mechanical stirring for 24 h. Reaction was checked by TLC (iodine), and starting material was detected, so 0.2 equivalents of K$_2$CO$_3$ were added to the mixture which was refluxed over weekend. Reaction was checked, starting material was still detected. 0.2 eq. of K$_2$CO$_3$ were added to the mixture, which was refluxed during 24 h.

Reaction was stopped, no advances were observed. Reaction mixture was filtered. Solvent was evaporated under reduced pressure. Residue was diluted with 50 ml of DCM, and washed with water. Organic layer was separated and aqueous fraction was extracted three times with 70 mL of DCM. Combined organic extracts were washed with brine, dried over Na$_2$SO$_4$ (anh), filtered and concentrated under reduce pressure. Residue was purified by chromatographic column 70 g cartridge (ISOLUTE silica) using Hex/EtOAc 100/0 to 20/80 giving (11.6 g 71%) colourless oil. $^1$H NMR (300 MHz, CDCl$_3$) δ ppm: 5.83 (s, 1H), 4.85 (q, 1H), 4.08-4.25 (m, 2H), 2.22-2.23 (m, 6H), 1.79 (d, 3H), 1.23 (t, 3H).

Intermediate 78

2-(3,5-dimethyl-1H-pyrazol-1-yl)propanohydrazide

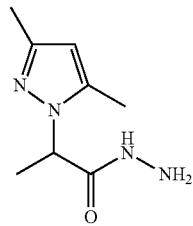

To a stirred solution of hydrazine-hydrate (FLUKA, 0.397 mol, 17.25 mL) in 100 mL of 95% EtOH, were added dropwise ethyl Intermediate 77 (11.6 g, 0.066 mol), previously dissolved in 60 ml of EtOH. Mixture of reaction was heated to 50° C. during 16 h. Reaction was followed by TLC (iodine). Solvent was eliminated in vacuum conditions giving (10.7 g, 98%) white solid characterized as the title compound. $^1$H NMR (300 MHz, CDCl$_3$) δ ppm: 7.90 (br.s, 1H), 5.85 (s, 1H), 4.80 (q, 1H), 3.82 (br.s, 2H), 2.21-2.24 (m, 6H), 1.75 (d, 3H), [ES+MS] m/z 183 (MH$^+$).

Intermediate 79

Ethyl 3-amino-2-methyl-3-thioxopropanoate

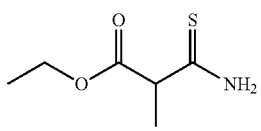

A mixture of diphenylphosphinodithioic acid (Alfa-Aesar) (7.48 g, 29.9 mmol) and 2-cyanopropionic acid ethyl ester (ABCR, 1.980 mL, 14.94 mmol) in isopropanol (80 mL) was heated under reflux for 8 h then stood at rt overnight. Reaction mixture was filtered and filtrate was diluted with EtOAc and washed with 1N NaOH, brine, and dried over Na$_2$SO$_4$. Crude was purified by chromatography on silica gel using a Hex/EtOAc gradient. Appropriate fractions were combined and evaporated to yield title compound as a yellow oily solid. $^1$H NMR (300 MHz, DMSO-d$_6$) δ ppm: 9.60 (s, 1H), 9.40 (s, 1H), 4.05 (q, 2H), 3.74 (q, 1H), 1.29 (d, 3H), 1.15 (t, 3H). [ES+MS] m/z 162 (MH$^+$).

Intermediate 80

Ethyl 2-(4-methyl-1,3-thiazol-2-yl)propanoate

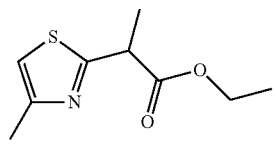

A mixture of Intermediate 79 (500 mg, 3.10 mmol) and chloroacetone (Fluka, 0.300 ml, 3.39 mmol) in DMF (6 ml) was stirred at 80° C. for 5 hours. Reaction mixture was cooled to room temperature, treated with NaHCO$_3$ and extracted with ethyl ether. Phases were separated and organic phase was washed with brine, dried over Na$_2$SO$_4$ and evaporated to give product as a yellow oil. $^1$H NMR (300 MHz, DMSO-d$_6$) δ ppm: 7.19 (s, 1H), 4.23-4.06 (m, 3H), 2.31 (s, 3H), 1.48 (d, 3H), 1.16 (t, 3H). [ES+MS] m/z 200 (MH$^+$). It was subsequently observed that this compound undergoes autooxidation at the stereogenic centre to form ethyl 2-hydroxy-2-(4-methyl-1,3-thiazol-2-yl)propanoate. Once the presence of this compound had been observed, the compound was actively synthesised, hereinbelow described as Intermediate 87.

Intermediate 81

2-(4-methyl-1,3-thiazol-2-yl)propanohydrazide and

Intermediate 82

2-hydroxy-2-(4-methyl-1,3-thiazol-2-yl)propanohydrazide

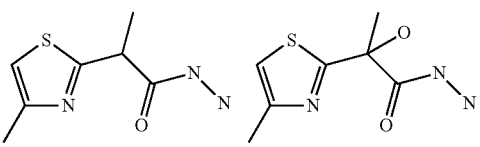

A solution of Intermediate 80 (315 mg, 1.581 mmol), an unknown proportion of which was subsequently discovered to be in the form of the autooxidation product of Intermediate 80 (hereinbelow described as Intermediate 87) and hydrazine monohydrate (0.384 ml, 7.90 mmol) in ethanol (5 ml) was heated under reflux. After 3 hours hydrazine monohydrate (Fluka, 0.384 ml, 7.90 mmol) was added and reaction mixture continued stirring under reflux for 4 hours. Reaction mixture was concentrated and residue was co-concentrated with toluene. Residue was preabsorbed on silica and purified by chromatography on silica gel using a DCM and MeOH gradient, and obtained two products. Intermediate 81: $^1$H NMR (300 MHz, DMSO-d$_6$) δ ppm: 9.36 (s, 1H), 7.12 (s, 1H), 4.27 (s, 2H), 3.92 (q, 1H), 2.30 (s, 3H), 1.40 (d, 3H). [ES+MS] m/z 186 (MH$^+$). Intermediate 82: $^1$H NMR (300 MHz, DMSO-d$_6$) δ ppm: 9.04 (s, 1H), 7.15 (s, 1H), 6.58 (s, 1H), 4.23 (s, 2H), 2.32 (s, 3H), 1.66 (s, 3H). [ES+MS] m/z 202 (MH⁺). An alternative procedure to make Intermediate 82 is described hereinbelow.

Intermediate 83

Ethyl 2-[4-(trifluoromethyl)-1,3-thiazol-2-yl]propanoate

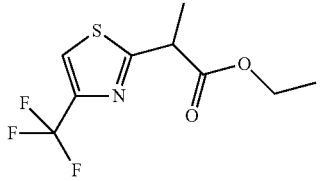 [SMILES: CCOC(=O)C(C)c1nc(C(F)(F)F)cs1]

A mixture of Intermediate 79 (350 mg, 2.171 mmol) and 3-Bromo-1,1,1-trifluoroacetone (Aldrich, 240 ml, 2.196 mmol) in DMF (6 ml) was stirred at 80° C. for 2 hours. Reaction mixture was cooled to room temperature, treated with NaHCO₃ and extracted with ethyl ether. Phases were separated and organic phase was washed with brine, dried over Na₂SO₄ and concentrated. Crude was purified by chromatography on silica gel using a Hex/EtOAc gradient to yield title compound as a clear oil. ¹H NMR (300 MHz, DMSO-d₆) δ ppm: 8.47 (s, 1H), 4.39 (q, 1H), 4.13 (q, 2H), 1.54 (d, 3H), 1.17 (t, 3H). [ES+MS] m/z 254 (MH⁺)

Intermediate 84

2-[4-(trifluoromethyl)-1,3-thiazol-2-yl]propanohydrazide

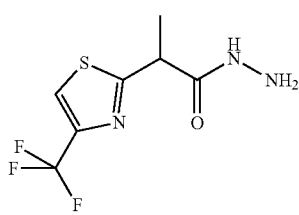

A solution of Intermediate 83 (240 mg, 0.948 mmol) and hydrazine monohydrate (0.230 ml, 4.74 mmol) in EtOH (5 ml) was heated under reflux. After 3 h. hydrazine monohydrate was added (0.230 ml, 4.74 mmol) and reaction mixture continued stirring under reflux for 4 hours. Reaction mixture was concentrated and residue was then co-concentrated with toluene to yield title compound as an oily solid. ¹H NMR (300 MHz, DMSO-d₆) δ ppm: 9.49 (s, 1H), 8.40 (s, 1H), 4.35 (s, 2H), 4.05 (q, 1H), 1.46 (d, 3H). [ES+MS] m/z 240 (MH⁺).

Intermediate 85

2-chloro-5-[(3,5-dimethyl-1H-pyrazol-1-yl)methyl]-1,3-thiazole

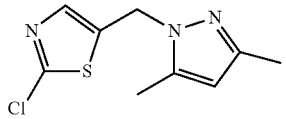

A solution of 3,5-dimethyl-1H-pyrazole (Aldrich, 114 mg, 1.190 mmol) in DMF (5 ml) was added over NaH (Aldrich, 34.3 mg, 1.42 mmol) at 0° C. under N₂ atmosphere. The mixture was stirred during 5 min and 2-chloro-5-(chloromethyl)-1,3-thiazole (AK scientific, 200 mg, 1.19 mmol) in DMF (2 ml) was added. The mixture was allowed to stir overnight. Finally, it was heated to 50° C. for 1 h. DMF was eliminated by washing with 14 ml of a mixture EtOAc/NH₄Cl 1N (1:1). The organic layer was dried over Na₂SO₄ and the solution concentrated to dryness under vacuum, to afford a crude product which was chromatographed (silica gel cartridge, Hex/EtOAc) yielding the title compound. ¹H NMR (300 MHz, CDCl₃) δ ppm: 7.37 (s, 1H); 5.82 (s, 1H), 5.26 (s, 2H); 2.24 (s, 3H); 2.22 (s, 3H). [ES+MS] m/z: 228.1 (MH+).

Intermediate 86 ethyl 2-bromo-2-(4-methyl-1,3-thiazol-2-yl)propanoate

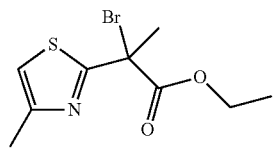

To a solution of ethyl 2-(4-methyl-1,3-thiazol-2-yl)propanoate (3.91 g, 19.62 mmol) in toluene (95 mL) was added hydrochloric acid (1.77 mL, 21.58 mmol). The mixture was stirred at room temperature for 10 minutes. The mixture was cooled to 0° C. and then potassium bromide (MERCK, 2.57 g, 21.58 mmol) and hydrogen peroxide (2.37 mL, 25.5 mmol) were added. Reaction mixture was stirred at 0° C. for 5 hours, at which point TLC (1:1 EtOAc-Hex) showed reaction had gone to completion. Reaction mixture was quenched with 1N Na₂S₂O₃ (60 mL) and saturated NaHCO₃ (60 mL). Organic phase was separated and the aqueous phase was extracted with ethyl acetate (2×60 mL). Combined organics were washed with brine, dried over sodium sulfate and concentrated to give the title compound (5.02 g, 18.05 mmol, 92% yield) as a red oil. ¹H-NMR (300 MHz, DMSO-d₆) δ ppm:

7.41 (s, 1H), 4.23 (q, 3H), 2.33 (s, 3H), 2.28 (s, 3H), 1.20 (t, 3H). [ES+MS] m/z 278 (MH⁺).

Intermediate 87 ethyl 2-hydroxy-2-(4-methyl-1,3-thiazol-2-yl)propanoate

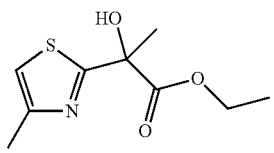

A mixture of Intermediate 86 (5.02 g, 18.05 mmol) and silver oxide (2.09 g, 9.02 mmol) in acetonitrile (56 mL) and water (14 mL) was stirred at room temperature overnight. Reaction mixture was filtered through a pad of Celite to remove solids, and the pad was washed with a 95:5 DCM-MeOH mixture (200 mL). The filtrate was concentrated to give 3.55 g of a brown residue. Crude was purified using a 100 g silica gel cartridge with mixtures hexane-ethyl acetate (gradient 0-30%) to give 2.08 g (9.66 mmol, 54%) of the title compound as yellow oil. $^1$H-NMR (300 MHz, DMSO-$d_6$) δ ppm: 7.19 (s, 1H), 6.71 (s, 1H), 4.08 (q, 2H), 2.31 (s, 3H), 1.68 (s, 3H), 1.13 (t, 3H). [ES+MS] m/z 216 (MH⁺).

Intermediate 82 (alternative procedure): 2-hydroxy-2-(4-methyl-1,3-thiazol-2-yl)propanohydrazide

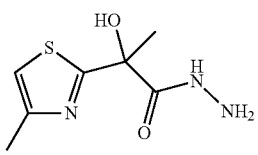

A solution of Intermediate 87 (2.08 g, 9.66 mmol) in ethanol (33 mL) was treated with hydrazine monohydrate (4.70 mL, 97 mmol) and the resulting mixture was heated under reflux for 3 h. Reaction mixture was concentrated and dried under vacuum overnight to give the title compound as white solid (1.94 g, 9.64 mmol, 100% yield). $^1$H-NMR (300 MHz, DMSO-$d_6$) δ ppm: 9.04 (s, 1H), 7.15 (s, 1H), 6.58 (s, 1H), 4.23 (s, 2H), 2.32 (s, 3H), 1.66 (s, 3H). ES+MS] m/z 202 (MH⁺).

Intermediate 88 ethyl 2-(methyloxy)-2-(4-methyl-1,3-thiazol-2-yl)propanoate

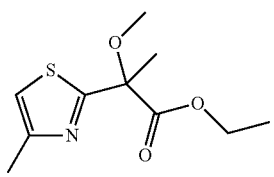

To a 60% dispersion sodium hydride (ALFAAESAR, 21 mg, 0.533 mmol) in mineral oil was added a solution of Intermediate 87 (85 mg, 0.355 mmol) in DMF (4 mL) at 0° C. under nitrogen. The resulting orange suspension was stirred for 10 minutes and then iodomethane (ALDRICH, 0.033 mL, 0.533 mmol) was added. The reaction was stirred at room temperature for 1 h. Then, mixture was diluted with EtOAc (25 mL), washed with 1N NH₄Cl (3×15 mL), brine, dried over sodium sulfate and concentrated to give 78 mg of crude. It was purified on a 2 g silica cartridge and eluted manually with a step gradient, 0-30% hexane-ethyl acetate to yield the title compound (51 mg, 0.220 mmol, 62.0% yield). $^1$H NMR (300 MHz, DMSO-$d_6$) δ ppm: 7.27 (s, 1H), 4.05-4.20 (m, 2H), 3.26 (s, 3H), 2.32 (s, 3H), 1.73 (s, 3H), 1.14 (t, 3H). [ES+MS] m/z 230 (MH⁺).

Intermediate 89 ethyl diazo(4-methyl-1,3-thiazol-2-yl)acetate

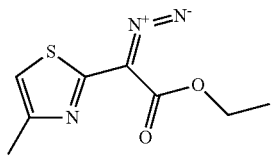

A solution of ethyl (4-methyl-1,3-thiazol-2-yl)acetate (ENAMINE, 300 mg, 1.619 mmol) in acetonitrile (ACN) (12 mL) was treated with triethylamine (FLUKA, 0.339 mL, 2.429 mmol) at 0° C. After 20 minutes 4-acetamidobenzenesulfonyl azide (ALDRICH, 389 mg, 1.619 mmol) was added and the mixture was allowed to reach room temperature overnight. Then, 4-acetamidobenzenesulfonyl azide (ALDRICH, 94 mg, 0.391 mmol) was added and continued stirring at room temperature for 2 h. Reaction mixture was concentrated and residue was triturated with a mixture 1:1 Et₂O-hexane and filtered. Solid was washed several times with the same mixture. The filtrate was concentrated to give 310 mg of crude. It was purified on a 10 g silica cartridge and eluted manually with linear gradient 0-50% hexane-ethyl acetate to yield the title compound (200 mg, 0.947 mmol, 58.5% yield). $^1$H NMR (300 MHz, DMSO-$d_6$) δ ppm: 7.49 (d, 1H), 4.34 (q, 2H), 2.60 (s, 3H), 1.32 (t, 3H). [ES+MS] m/z 212 (MH⁺).

Intermediate 90 ethyl (methyloxy)(4-methyl-1,3-thiazol-2-yl)acetate

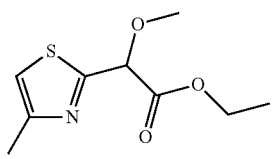

A solution of Intermediate 89 (400 mg, 1.894 mmol) in DCM (16 mL) was treated with rhodium (II) acetate dimer (ALDRICH, 17 mg, 0.038 mmol) and MeOH (0.230 mL, 5.68 mmol). Reaction mixture was stirred at room temperature for 4 hours and heated at 40° C. for 4 h more. MeOH (0.230 mL, 5.68 mmol) was added and continued stirring at room temperature overnight. An spatula tip of catalyst was added and heated at 40° C. for 4 h. 75% of the solvent was evaporated, the residue was loaded directly on a 10 g silica cartridge and eluted with a linear gradient 0-50% hexane-ethyl acetate to yield the title compound as an oily liquid (350 mg, 1.626 mmol, 85.8% yield). $^1$H NMR (300 MHz, DMSO-$d_6$) δ ppm: 7.32 (d, 1H), 5.22 (d, 1H), 4.16 (q, 2H), 3.38 (s, 3H), 2.33 (s, 3H), 1.17 (t, 3H). [ES+MS] m/z 216 (MH$^+$).

Intermediate 91 ethyl 3-amino-2,2-dimethyl-3-thioxopropanoate

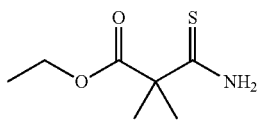

A mixture of diphenyldithiophosphonic acid (ALFAAE-SAR, 1.42 g, 5.67 mmol) and 2-cyano-2-methylpropionic acid ethyl ester (ABCR, 0.412 mL, 2.83 mmol) in isopropanol (30 mL) was heated under reflux for 4 h. Reaction mixture was cooled to room temperature and a precipitate was formed. Reaction flask was placed in the freezer for 1 h. Reaction mixture was filtered and filtrate was concentrated. Residue was taken up in DCM (100 mL) and washed with water (20 mL), 1N NaOH (20 mL), saturated NaHCO$_3$ (20 mL) and dried over sodium sulfate and concentrated. The resulting oil was loaded on a 25 g silica cartridge and eluted with linear gradient 0-50% hexane-ethyl acetate to yield the title compound (110 mg, 0.628 mmol, 22.2% yield). Another impure batch was loaded on a 10 g silica cartridge and eluted with linear gradient 0-50% hexane-ethyl acetate to recover the title compound (120 mg, 0.685 mmol, 24.17% yield). Total yield: (230 mg, 1.313 mmol, 46.32%). $^1$H NMR (300 MHz, DMSO-$d_6$) δ ppm: 9.70 (br s, 1H), 8.86 (br s, 1H), 4.05 (q, 2H), 1.39 (s, 6H), 1.15 (t, 3H). [ES+MS] m/z 176 (MH$^+$).

Intermediate 92 ethyl 2-methyl-2-(4-methyl-1,3-thiazol-2-yl)propanoate

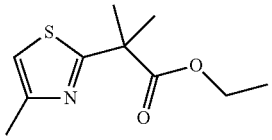

A mixture of Intermediate 91 (220 mg, 1.255 mmol) and chloroacetone (FLUKA, 0.111 mL, 1.255 mmol) in DMF (4 mL) was stirred at 80° C. for 5 h and continued heating at 50° C. overnight. Chloroacetone (FLUKA, 0.060 mL, 0.678 mmol) was added and continued stirring at 80° C. for 2 hours. Reaction mixture was cooled to room temperature, diluted with diethyl ether (50 mL), washed with 1N NH$_4$Cl (2×20 mL), saturated NaHCO$_3$ (20 mL), brine (20 mL), dried over Na$_2$SO$_4$ and concentrated to give the title compound (240 mg, 1.125 mmol, 90% yield). $^1$H NMR (300 MHz, DMSO-$d_6$) δ ppm: 7.17-7.20 (m, 1H), 4.07 (q, 2H), 2.31 (d, 3H), 1.58 (s, 6H), 1.12 (t, 3H). [ES+MS] m/z 214 (MH$^+$).

Intermediates 93-95 were prepared by a method analogous to that described for Intermediate 84 but replacing Intermediate 83 (the ester) with that indicated in Table D.

Modifications in the purification step are also indicated.

TABLE D

| Int. | Structure | Ester to replace Int. 83 | Physical data |
|---|---|---|---|
| 93 | (thiazole hydrazide with OMe) | Intermediate 88 | $^1$H NMR (300 MHz, DMSO-$d_6$) δ ppm: 9.24 (br s, 1H), 7.24 (s, 1H), 4.10-4.50 (m, 2H), 3.16 (s, 3H), 2.32 (s, 3H), 1.70 (s, 3H). [ES + MS] m/z 216 (MH+). |
| 94 | (thiazole hydrazide with OMe, no methyl) | Intermediate 90 | $^1$H NMR (300 MHz, DMSO-$d_6$) δ ppm: 9.57 (br s, 1H), 7.26 (d, 1H), 4.94 (s, 3H), 4.38 (br s, 2H), 2.32 (s, 3H). |
| 95 | (thiazole hydrazide gem-dimethyl) a) | Intermediate 92 | $^1$H NMR (300 MHz, DMSO-$d_6$) δ ppm: 8.95 (br s, 1H), 7.13 (s, 1H), 4.24 (br s, 2H), 2.31 (s, 3H), 1.54 (s, 6H). [ES + MS] m/z 200 (MH+). | a) Residue was pre-absorbed on silica and loaded on a 10 g silica gel cartridge, eluted with a linear gradient, 0-20% MeOH-DCM.

Intermediate 96

(2,6-difluoro-3-nitrophenyl)methanol

The title compound was prepared following the procedure described for the compound 18 in the reference Bioorganic and Medicinal Chemistry, 1999, 7(11), page 2660 using 2,6-difluoro-3-nitrobenzoic acid (APOLLO, 500 mg, 2.462 mmol) as starting material. Crude was purified using a 20 g silica gel cartridge with linear gradient 0-5% DCM/MeOH to yield the title compound (340 mg, 1.798 mmol, 73% yield) as white solid. $^1$H NMR (300 MHz, DMSO-$d_6$) δ ppm: 8.15-8.30 (m, 1H), 7.30-7.45 (m, 1H), 5.50 (t, 1H), 4.55 (d, 2H).

Intermediate 97

(3-amino-2,6-difluorophenyl)methanol

Intermediate 96 (60 mg, 0.317 mmol) was dissolved in 10 mL of ethyl acetate. Solution was passed through H-cube system using a Pd(C) cartridge to obtain the title compound after solvent elimination (47 mg, 0.295 mmol, 93% yield) as white solid. An additional batch of title compound was obtained starting from 282 mg (1.49 mmol) of Intermediate 96 under the same conditions and the two batches were combined to give the title compound 230 mg (1.45 mmol, 97% yield) as white solid. $^1$H NMR (300 MHz, DMSO-$d_6$) δ ppm: 6.60-6.80 (m, 2H), 5.08 (t, 1H), 4.91 (br s, 2H), 4.42 (d, 2H).

Intermediate 98

[3-(acetylamino)-2,6-difluorophenyl]methyl acetate

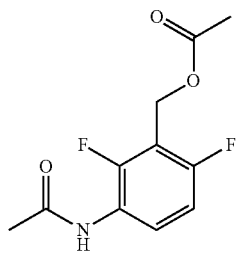 [SMILES: CC(=O)Nc1ccc(F)c(COC(C)=O)c1F]

The title compound was prepared from Intermediate 97 (278 mg, 1.747 mmol) following the procedure described for the compound 20 (page 2660) in reference: Bioorganic and Medicinal Chemistry, 1999, 7(11), pg. 2647-2666. In this procedure the use of pyrrolidine was omitted. Crude of reaction was purified on a 10 g silica cartridge and eluted with linear gradient 0-50% hexane-ethyl acetate to yield the title compound (345 mg, 1.419 mmol, 81% yield) as white solid. $^1$H NMR (300 MHz, DMSO-$d_6$) δ ppm: 9.77 (br s, 1H), 7.77-7.88 (m, 1H), 7.05-7.15 (m, 1H), 5.12 (s, 2H), 2.06 (s, 3H), 2.02 (s, 3H). [ES+MS] m/z 244 (MH+).

Intermediate 99

N-[2,4-difluoro-3-(hydroxymethyl)phenyl]acetamide

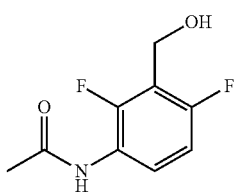

The title compound was prepared from Intermediate 98 (340 mg, 1.398 mmol) following the procedure described for the compound 21(page 2660) in the reference: Bioorganic and Medicinal Chemistry, 1999, 7(11), pg. 2647-2666 to obtain the desired compound (236 mg, 1.114 mmol, 80% yield). $^1$H NMR (300 MHz, DMSO-$d_6$) δ ppm: 9.69 (br s, 1H), 7.67-7.77 (m, 1H), 6.95-7.06 (m, 1H), 5.26 (t, 1H), 4.49 (d, 2H), 2.06 (s, 3H). [ES+MS] m/z 202 (MH+).

Intermediate 100

[3-(acetylamino)-2,6-difluorophenyl]methyl methanesulfonate

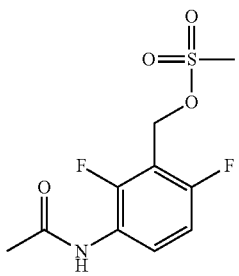 [SMILES: CC(=O)Nc1ccc(F)c(COS(C)(=O)=O)c1F]

The compound was prepared from Intermediate 99 (236 mg, 1.173 mmol) following the procedure described for the compound 22 (page 2660) in the reference: Bioorganic and Medicinal Chemistry, 1999, 7(11), pg. 2647-2666 to give the title compound (216 mg, 0.696 mmol, 59.3% yield). $^1$H NMR (300 MHz, DMSO-$d_6$) δ ppm: 9.82 (br s, 1H), 7.84-7.95 (m, 1H), 7.12-7.20 (m, 1H), 5.32 (s, 2H), 3.25 (s, 3H), 2.07 (s, 3H). [ES+MS] m/z 280 (MH+).

Intermediate 101

(3-amino-2-fluorophenyl)methanol

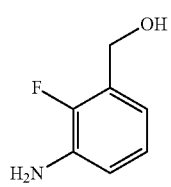

3-amino-2-fluorobenzoic acid (APIN, 250 mg, 1.612 mmol) was dissolved in 10 mL of anhydrous THF under $N_2$ atmosphere. Solution was cooled at 0° C. in an ice-water bath. $LiAlH_4$ (FLUKA, 183 mg, 4.83 mmol) was added. Reaction was stirred under nitrogen at room temperature. After 2 h one equivalent of $LiAlH_4$ (FLUKA, 61 mg, 1.62 mmol) was added to the mixture and reaction was stirred at room temperature overnight. Another equivalent of $LiAlH_4$ (FLUKA, 61 mg, 1.62 mmol) was added. After 5 h The reaction mixture was quenched by adding MeOH. Solvent was evaporated to obtain an orange syrup that was dissolved in EtOAc and partitioned with saturated $NaHCO_3$ (aqueous) (10 mL of saturated solution+15 mL of distilled water). Aqueous phase was extracted with EtOAc, organic layers were combined and dried with $MgSO_4$ (anh), filtered off and concentrated. Crude was purified using silica gel cartridge with linear gradient 0-85% DCM/MeOH to yield the title compound (114 mg, 0.808 mmol, 50.1% yield) as yellow syrup. $^1$H NMR (300 MHz, DMSO-$d_6$) δ ppm: 6.50-6.85 (m, 3H), 4.95-5.08 (m, 3H), 4.44 (d, 2H).

Intermediate 102 ethyl [2-fluoro-3-(hydroxymethyl)phenyl]carbamate

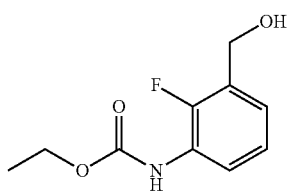

A stirred suspension of sodium carbonate (78 mg, 1.573 mmol) and Intermediate 101 (222 mg, 1.573 mmol) in 10 mL of water was cooled at 0° C. under nitrogen atmosphere. Ethyl chlorocarbonate (ALDRICH, 171 mg, 1.573 mmol) was added dropwise. Reaction was stirred for 1 h 30 min at 0° C. and then allowed to reach room temperature. Crude of reaction was partitioned with $Et_2O$. Organic layers were dried with $MgSO_4$ (anh), filtered and concentrated to obtain the title compound (359 mg, 1.600 mmol, quantitative yield). $^1$H NMR (300 MHz, DMSO-$d_6$) δ ppm: 9.21 (br s, 1H), 7.45-7.55 (m, 1H), 7.05-7.22 (m, 2H), 5.24 (br s, 1H), 4.51 (s, 2H), 4.10 (q, 2H), 1.22 (t, 3H). [ES+MS] m/z 214 (MH+).

Intermediate 103 ethyl [3-(bromomethyl)-2-fluoroohenyl]carbamate

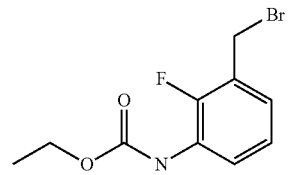

Intermediate 102 (250 mg, 1.173 mmol) was dissolved under nitrogen atmosphere in 15 mL of DCM at 0° C. Carbon tetrabromide (ALDRICH, 583 mg, 1.759 mmol) and triphenyl phosphine (ALDRICH, 461 mg, 1.1759 mmol) were added to the solution. Reaction was stirred at room temperature overnight and solvent was evaporated. Crude of reaction was purified on a 20 g silica cartridge and eluted with linear gradient 0-20% hexane-ethyl acetate to yield the title compound (255 mg, 0.877 mmol, 74.8% yield). $^1$H NMR (300 MHz, DMSO-$d_6$) δ ppm: 9.37 (br s, 1H), 7.56-7.66 (m, 1H), 7.18-7.29 (m, 1H), 7.08-7.17 (m, 1H), 4.68 (s, 2H), 4.12 (q, 2H), 1.23 (t, 3H). [ES+MS] m/z 276 (MH$^+$).

Intermediate 104 ethyl (3-{[3-(1,3-dioxo-1,3-dihydro-2H-isoindol-2-yl)-1H-pyrazol-1-yl]methyl}-2-fluorophenyl)carbamate

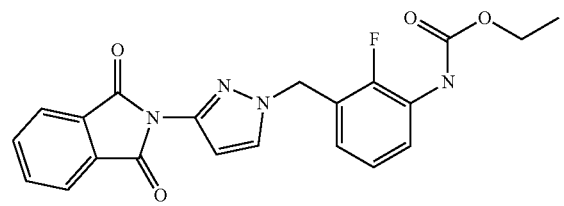 [SMILES: CCOC(=O)Nc1cccc(Cn2ccc(N3C(=O)c4ccccc4C3=O)n2)c1F]

Intermediate 27 (236 mg, 1.108 mmol) was dissolved in 15 mL of acetonitrile under nitrogen atmosphere. Potassium carbonate (ALDRICH, 153 mg, 1.108 mmol) was added in one portion and reaction mixture was stirred during 20 minutes at room temperature. Intermediate 103 (255 mg, 0.924 mmol) was added and reaction was heated to 70° C. during 2 h and then stirred at room temperature overnight. Solvent was evaporated and crude of reaction was partitioned between DCM and distilled water. Organic layer was dried over $MgSO_4$ (anh), filtered and concentrated. The solid was purified on a silica cartridge. Two regioisomers were observed, so a new purification was carried out to separate the non-desired isomer ethyl (3-{[5-(1,3-dioxo-1,3-dihydro-2H-isoindol-2-yl)-1H-pyrazol-1-yl]methyl}-2-fluorophenyl)carbamate. A preparative HPLC purification was performed with SUN-FIRE (30×150 mm) column and gradient 40%-80% ACN: $NH_4CO_3$ (aqueous, 10 mM) to give the title compound (90 mg, 0.220 mmol, 23.9% yield). $^1$H NMR (300 MHz, DMSO-$d_6$) δ ppm: 9.36 (br s, 1H), 7.86-7.99 (m, 5H), 7.57-7.66 (m, 1H), 7.08-7.16 (m, 1H), 6.94-7.02 (m, 1H), 6.39 (d, 1H), 5.42 (s, 2H), 4.11 (q, 2H), 1.22 (t, 3H).

Intermediate 105

N-(3-{[3-(1,3-dioxo-1,3-dihydro-2H-isoindol-2-yl)-1H-pyrazol-1-yl]methyl}-2,4-difluorophenyl)acetamide

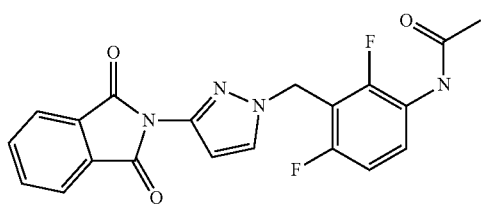 [SMILES: CC(=O)Nc1ccc(F)c(Cn2ccc(N3C(=O)c4ccccc4C3=O)n2)c1F]

Intermediate 27 (210 mg, 0.901 mmol) was dissolved in 10 mL of acetonitrile under nitrogen atmosphere. Potassium carbonate (ALDRICH, 124 mg, 0.752 mmol) was added in one portion, mixture of reaction was left under stirring during 20 min. After that time, Intermediate 99 (210 mg, 0.752 mmol) was added, mixture of reaction was heated to 70° C. during 1 h and then overnight at 50° C. Solvent was eliminated, and crude of reaction was partitioned between DCM and distilled water. Organic layer was dried, concentrated and purified using a silica 10 g Merck cartridge using DCM:MeOH as solvents. A second purification was carried out, using a silica 10G Merck cartridge using DCM:MeOH as solvents (a lower polarity of the eluents mixture was used) to obtain the title compound (70 mg, 0.177 mmol, 23.5% yield). $^1$H NMR (300 MHz, DMSO-$d_6$) δ ppm: 9.78 (br s, 1H), 7.79-7.98 (m, 6H), 7.06-7.15 (m, 1H), 6.34-6.38 (m, 1H), 5.43 (s, 2H), 2.05 (s, 3H). [ES+MS] m/z 397 (MH+).

Intermediates 106-108 were prepared by a method analogous to that described for Intermediate 6 but replacing the benzyl bromide (2-(bromomethyl)-1-chloro-3-fluorobenzene) with that indicated in Table E. The benzyl bromide was dissolved in anhydrous DMF and added dropwise. Modifications in the purification step are also indicated.

TABLE E

| Int. | Structure | Benzyl bromide | Physical data |
|---|---|---|---|
| 106 | (structure with pyrazole-N-acetamide and 4-fluorobenzyl group)<br>a) | Br-CH2-C6H4-F<br>ALDRICH | $^1$H NMR (300 MHz, DMSO-$d_6$) δ ppm: 10.37 (br s, 1H), 7.70 (d, 1H), 7.11-7.29 (m, 4H), 6.45 (d, 1H), 5.17 (s, 2H), 1.94 (s, 3H). [ES + MS] m/z 234 (MH+). |
| 107 | (structure with 2,6-difluorobenzyl group)<br>b) | Br-CH2-C6H2F3<br>ALDRICH | $^1$H NMR (300 MHz, DMSO-$d_6$) δ ppm: 10.39 (br s, 1H), 7.70 (d, 1H), 7.45-7.58 (m, 1H), 7.12-7.22 (m, 1H), 6.44 (d, 1H), 5.30 (s, 2H), 1.92 (s, 3H), [ES + MS] m/z 270 (MH+). |
| 108 | (structure with 2-fluoro-3-methylbenzyl group) | Br-CH2-C6H2F2-CH3<br>APOLLO | $^1$H NMR (300 MHz, DMSO-$d_6$) δ ppm: 10.39 (br s, 1H), 7.65 (d, 1H), 7.24-7.35 (m, 1H), 6.96-7.05 (m, 1H), 6.42 (d, 1H), 5.24 (s, 2H), 2.18 (s, 3H), 1.91 (s, 3H). [ES + MS] m/z 266 (MH+). | a) Reaction was partitioned between saturated NH$_4$Cl and DCM, and purified by FlashMaster using a 10 g silica gel cartridge with gradient Hexane/AcOEt (0-70%).
b) Reaction was partitioned between saturated NH$_4$Cl and DCM, and purified by FlashMaster using a 25 g silica gel cartridge with gradient Hexane/AcOEt (0-50%).

Intermediates 109-112 were prepared by a method analogous to that described for intermediate 37 but replacing intermediate 6 (acetyl intermediate) with the intermediate indicated in Table F. Modifications in the purification step are also indicated.

TABLE F

| Int. | Structure | Intermediate (to replace Int. 6) | Physical data |
|---|---|---|---|
| 109 | a) | 106 | $^1$H NMR (300 MHz, DMSO-$d_6$) δ ppm: 7.42 (d, 1H), 7.08-7.25 (m, 4H), 5.39 (d, 1H), 4.99 (s, 2H), 4.55 (br s, 2H). [ES + MS] m/z 192 (MH$^+$). |
| 110 | a), b) | 107 | $^1$H NMR (300 MHz, DMSO-$d_6$) δ ppm: 7.42-7.55 (m, 1H), 7.40 (d, 1H), 7.09-7.19 (m, 1H), 5.36 (d, 1H), 5.11 (s, 2H), 4.60 (br s, 2H). [ES + MS] m/z 228 (MH$^+$). |
| 111 | a) | 108 | $^1$H NMR (300 MHz, DMSO-$d_6$) δ ppm: 7.34 (d, 1H), 7.22-7.32 (m, 1H), 6.94-7.02 (m, 1H), 5.35 (d, 1H), 5.05 (s, 2H), 4.57 (br s, 2H), 2.18 (s, 3H). [ES + MS] m/z 224 (MH$^+$). |
| 112 | a), b) | 107 | $^1$H NMR (300 MHz, DMSO-$d_6$) δ ppm: 7.22-7.33 (m, 2H), 6.91-7.01 (m, 1H), 5.35 (d, 1H), 5.02 (s, 2H), 4.52 (br s, 2H), 4.05 (qd, 2H), 1.29 (t, 3H). [ES + MS] m/z 254 (MH$^+$). | a) Remaining aqueous fraction was diluted with distilled water and EtOAc. Aqueous layer was extracted with EtOAc (x3); organic layers were combined and dried over MgSO$_4$ anh, and concentrated.
b) Purified by preparative HPLC using XTERRA Chromatography Column (30 × 150 mm), Method (0_80) ACN (0.1% TFA)/H$_2$O (0.1% TFA).

Intermediate 113 ethyl {3-[(3-amino-1H-pyrazol-1-yl)methyl]-2-fluorophenyl}carbamate

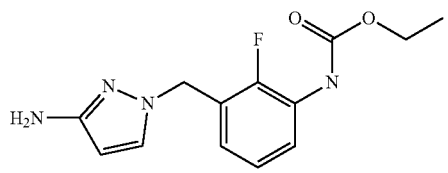 [SMILES: CCOC(=O)Nc1cccc(Cn2ccc(N)n2)c1F]

Intermediate 103 (86 mg, 0.211 mmol) was dissolved in EtOH (10 mL) and hydrazine monohydrate (FLUKA, 31 μL, 0.632 mmol) was added. Reaction was left under stirring overnight. Crude of reaction was filtered to eliminate a white precipitate. Filtrate was concentrated, and dissolved in DCM, a white solid precipitated, and solution was filtered again. Filtrate was concentrated to give the title compound (56 mg, 0.191 mmol, 91% yield). $^1$H NMR (300 MHz, DMSO-$d_6$) δ ppm: 9.28 (br s, 1H), 7.48-7.58 (m, 1H), 7.41 (d, 1H), 7.01-7.10 (m, 1H), 6.78-6.85 (m, 1H), 5.40 (d, 1H), 5.05 (s, 2H), 4.57 (br s, 2H), 4.11 (q, 2H), 1.22 (t, 3H). [ES+MS] m/z 279 (MH$^+$).

Intermediate 114

N-{3-[(3-amino-1H-pyrazol-1-yl)methyl]-2,4-difluorophenyl}acetamide

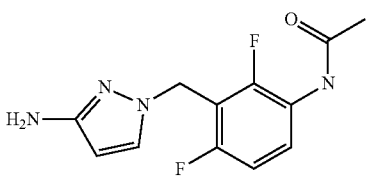 [SMILES: CC(=O)Nc1ccc(F)c(Cn2ccc(N)n2)c1F]

Intermediate 104 (95 mg, 0.240 mmol) was dissolved in EtOH (5 mL) and hydrazine monohydrate (FLUKA, 15 μL, 0.312 mmol) was added. Reaction was left under stirring conditions overnight. Crude of reaction was filtered to eliminate a white precipitate. Filtrate was concentrated to give the title compound (77 mg, 0.289 mmol, quantitative yield). $^1$H NMR (300 MHz, DMSO-$d_6$) δ ppm: 9.72 (br s, 1H), 8.01-8.08 (m, 1H), 7.78-7.87 (m, 1H), 7.36 (s, 1H), 5.35 (s, 1H), 5.07 (s, 2H), 4.55 (br s, 2H), 2.04 (s, 3H).

Intermediates 115-120 were prepared by a method analogous to that described for Intermediate 57 but replacing the Intermediate 37 with that indicated in Table G. The solvent used in the synthesis of these intermediates was DCM instead of chloroform. Reaction time: from 30 minutes to 8 h. Modifications in the purification step are also indicated.

TABLE G

| Int. | Structure | Starting intermediate (to replace Int. 37) | Physical data |
|---|---|---|---|
| 115 | a) | 109 | $^1$H NMR (300 MHz, DMSO-d$_6$) δ ppm: 7.93 (d, 1H), 7.27-7.35 (m, 2H), 7.13-7.23 (m, 2H), 6.44 (d, 1H), 5.26 (s, 2H). [MS] m/z 234 (MH$^+$). |
| 116 | a) | 110 | $^1$H NMR (300 MHz, DMSO-d$_6$) δ ppm: 7.95 (s, 1H), 7.46-7.62 (m, 1H), 7.12-7.25 (m, 1H), 6.38-6.46 (m, 1H), 5.39 (s, 2H). [ES + MS] m/z 270 (MH$^+$). |
| 117 | a) | 111 | $^1$H NMR (300 MHz, DMSO-d$_6$) δ ppm: 7.90 (d, 1H), 7.28-7.39 (m, 1H), 6.99-7.09 (m, 1H), 6.41 (dd, 1H), 5.33 (s, 2H), 2.19 (s, 3H). [ES + MS] m/z 266 (MH$^+$). |
| 118 | a) | 112 | $^1$H NMR (300 MHz, DMSO-d$_6$) δ ppm: 7.86 (d, 1H), 7.29-7.40 (m, 1H), 6.97-7.06 (m, 1H), 6.41 (dd, 1H), 5.28 (s, 2H), 4.08 (q, 2H), 1.28 (t, 3H). [ES + MS] m/z 296 (MH$^+$). |

TABLE G-continued

| Int. | Structure | Starting intermediate (to replace Int. 37) | Physical data |
|---|---|---|---|
| 119 | (structure) b) | 113 | $^1$H NMR (300 MHz, DMSO-$d_6$) δ ppm: 9.33 (br s, 1H), 7.92 (d, 1H), 7.55-7.64 (m, 1H), 7.07-7.15 (m, 1H), 6.91-6.99 (m, 1H), 6.44 (d, 1H), 5.33 (s, 2H), 4.11 (q, 2H), 1.22 (t, 3H). [ES + MS] m/z 321 (MH$^+$). |
| 120 | (structure) b) | 114 | $^1$H NMR (300 MHz, DMSO-$d_6$) δ ppm: 9.77 (br s, 1H), 7.92 (d, 1H), 7.77-7.90 (m, 1H), 7.05-7.15 (m, 1H), 6.42 (d, 1H), 5.36 (s, 2H), 2.05 (s, 3H). | a) Reaction was diluted with DCM and aqueous sodium bicarbonate. Phases were separated and organic phase was dried over MgSO$_4$ (anh), filtrated and concentrated.
b) Reaction was diluted with DCM and distilled water. Phases were separated and organic phase was dried over Na$_2$SO$_4$ (anh), filtrated and concentrated.

Intermediate 121

Ethyl (2-fluoro-3-{[3-({5-[1-hydroxy-1-(4-methyl-1,3-thiazol-2-yl)ethyl]-1,3,4-thiadiazol-2-yl}amino)-1H-pyrazol-1-yl]methyl}phenyl)carbamate

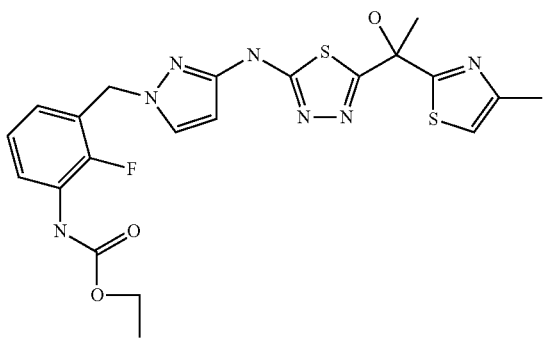 [SMILES: CCOC(=O)Nc1cccc(Cn2ccc(Nc3nnc(C(C)(O)c4nc(C)cs4)s3)n2)c1F]

A solution of Intermediate 118 (Ethyl {2-fluoro-3-[(3-isothiocyanato-1H-pyrazol-1-yl)methyl]phenyl}carbamate (105 mg, 0.328 mmol)) in 10 ml of DCM and Intermediate 82 (2-hydroxy-2-(4-methyl-1,3-thiazol-2-yl)propanohydrazide (73 mg, 0.361 mmol)) was stirred at room temperature 1 hour. Solvent was evaporated to give an orange solid characterized as Ethyl [2-fluoro-3-({3-[({2-[2-hydroxy-2-(4-methyl-3H-1l4,3-thiazol-2-yl)propanoyl]hyd razino}carbonothioyl)amino]-1H-pyrazol-1-yl}methyl)phenyl]carbamate (138 mg, 0.264 mmol). This solid was dissolved in 2 mL of H2SO4 (conc) and reaction mixture was maintained under stirring at room temperature during 1 h 30 min. Then reaction was neutralized by adding NH3 (aq, 32%) and partitioned with AcOEt (15 mL×3). Organic layer was dried over MgSO4, filtered and concentrated to obtain 103 mg of an orange solid that was purified by HPLC using XTERRA Chromatography Column (19 mm×150 mm), Method (25_100) ACN/H$_2$O (0.1% NH$_4$CO$_3$ 10 mM). After combining appropriated fractions 23 mg of a light orange solid were obtained and characterized as the title compound. $^1$H NMR (300 MHz, DMSO-$d_6$) δ ppm: 10.86 (br s, 1H), 9.30 (br s, 1H), 7.71 (d, 1H), 7.53-7.61 (m, 1H), 7.28 (s, 1H), 7.19 (s, 1H), 7.03-7.11 (m, 1H), 6.84-6.91 (m, 1H), 5.98 (d, 1H), 5.26 (s, 2H), 4.11 (q, 2H), 2.29 (s, 3H), 1.97 (s, 3H), 1.22 (t, 3H). [ES+MS] m/z 504 (MH⁺)

EXAMPLES

Method A

Example 1

5-[1-(3,5-dimethyl-1H-pyrazol-1-yl)ethyl]-N-(1-{[2-(trifluoromethyl)phenyl]methyl}-1H-pyrazol-3-yl)-1,3,4-thiadiazol-2-amine

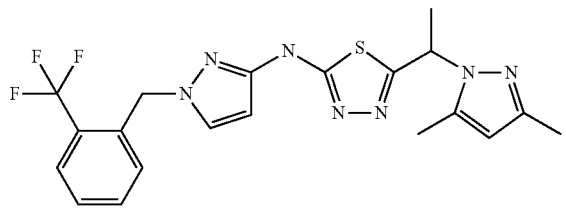 [SMILES: Cc1cc(C)n(C(C)c2nnc(Nc3ccn(Cc4ccccc4C(F)(F)F)n3)s2)n1]

A solution of Intermediate 61 (3-isothiocyanato-1-{[2-(trifluoromethyl)phenyl]methyl}-1H-pyrazole, 300 mg, 1.059 mmol) and Intermediate 78 (2-(3,5-dimethyl-1H-pyrazol-1-yl)propanohydrazide, 193 mg, 0.231 mmol) in 5 ml of DCM (anh) was stirred at room temperature during 2 hours. Reaction mixture was concentrated under vacuum to give 2-[2-(3,5-dimethyl-1H-pyrazol-1-yl)propanoyl]-N-(1-{[2-(trifluoromethyl)phenyl]methyl}-1H-pyrazol-3-yl)hydrazinecarbothioamide (460 mg, 93%) as a yellow solid [ES+MS] m/z 466 (MH⁺)]. Solid was dissolved in $H_2SO_4$ (conc) 4 mL and stirred at room temperature during 3 h. Resulting mixture was neutralized with 32% $NH_3$ (aq) under ice-bath until basic precipitate was achieved giving a pale yellow precipitate that was filtered-off, washed with cold-water and dried under vacuum to give a pale yellow solid that was dissolved in EtOAc and washed with water. Organic layer, was dried with $MgSO_4$ (anh) filtered, and dried under vacuum giving the title compound (56 mg, 81%) as a white solid. $^1$H NMR (300 MHz, DMSO-$d_6$) δ ppm: 10.91 (s, 1H), 7.75-7.80 (m, 2H), 7.59-7.64 (m, 1H), 7.50-7.55 (m, 1H), 7.06-7.09 (m, 1H), 6.01 (d, 1H), 5.83 (s, 1H), 5.76 (q, 1H), 5.40 (s, 2H), 2.23 (s, 3H), 2.07 (s, 3H), 1.78 (d, 3H). [ES+MS] m/z 448 (MH⁺).

Examples 2-17 were prepared by methods analogous to that described for Example 1 replacing isothiocyanate and hydrazide Intermediates 61 and 78 with the indicated in Table 1. Modifications in the purification step are also indicated.

TABLE 1

| Ex. | Structure | Isothiocyanate intermediate | Hydrazide intermediate | Physical data |
|---|---|---|---|---|
| 2 | N-{1-[(2,5-dichlorophenyl)methyl]-1H-pyrazol-3-yl}-5-[1-(3,5-dimethyl-1H-pyrazol-1-yl)ethyl]-1,3,4-thiadiazol-2-amine<br>See footnote (a) | 58<br>0.231 mmol | 78<br>0.231 mmol | $^1$H NMR (300 MHz, DMSO-$d_6$) δ ppm: 7.79 (d, 1H), 7.51-7.54 (m, 1H), 7.41-7.45 (m, 1H), 7.15 (d, 1H), 6.01 (d, 1H), 5.83 (s, 1H), 5.77 (q, 1H), 5.32 (s, 2H), 2.25 (s, 3H), 2.08 (s, 3H), 1.79 (d, 3H). [ES + MS] m/z 448 (MH⁺). |
| 3 | N-{1-[(2-bromophenyl)methyl]-1H-pyrazol-3-yl}-5-[1-(3,5-dimethyl-1H-pyrazol-1-yl)ethyl]-1,3,4-thiadiazol-2-amine<br>See footnote (a) | 60<br>0.255 mmol | 78<br>0.255 mmol | $^1$H NMR (300 MHz, DMSO-$d_6$) δ ppm: 7.76 (d, 1H), 7.63-7.66 (m, 1H), 7.23-7.37 (m, 2H), 7.02-7.05 (m, 1H), 5.99 (d, 1H), 5.84 (br s, 1H), 5.76 (q, 1H), 5.29 (s, 2H), 2.24 (s, 3H), 2.09 (s, 3H), 1.79 (d, 3H). [ES + MS] m/z 458 (MH⁺). |

TABLE 1-continued

| Ex. | Structure | Isothiocyanate intermediate | Hydrazide intermediate | Physical data |
|---|---|---|---|---|
| 4 | 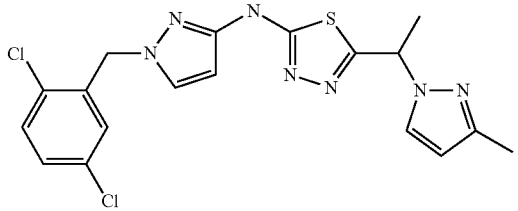<br>N-{1-[(2,5-dichlorophenyl)methyl]-1H-pyrazol-3-yl}-5-[1-(3-methyl-1H-pyrazol-1-yl)ethyl]-1,3,4-thiadiazol-2-amine | 58<br>0.197 mmol | 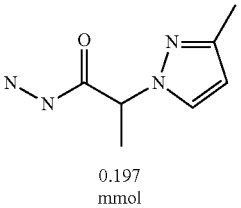<br>0.197 mmol<br>ARTCHEM | $^1$H NMR (300 MHz, DMSO-$d_6$) δ ppm: 10.93 (br s, 1H), 7.79 (d, 1H), 7.73 (d, 1H), 7.51-7.54 (m, 1H), 7.41-7.45 (m, 1H), 7.13 (d, 1H), 6.01-6.06 (m, 2H), 5.83 (q, 1H), 5.32 (s, 2H), 2.15 (s, 3H), 1.82 (d, 3H). [ES + MS] m/z 434 (MH$^+$). |
| 5 | 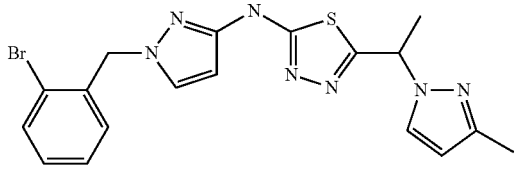<br>N-{1-[(2-bromophenyl)methyl]-1H-pyrazol-3-yl}-5-[1-(3-methyl-1H-pyrazol-1-yl)ethyl]-1,3,4-thiadiazol-2-amine | 60<br>0.258 mmol | 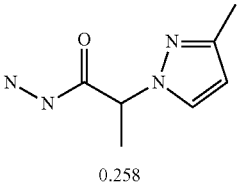<br>0.258 mmol<br>ARTCHEM | $^1$H NMR (300 MHz, DMSO-$d_6$) δ ppm: 10.91 (br s, 1H), 7.75-7.76 (m, 2H), 7.63-7.66 (m, 1H), 7.23-7.37 (m, 2H), 6.99-7.02 (m, 1H), 6.06 (d, 1H), 5.99 (d, 1H), 5.83 (q, 1H), 5.29 (br s, 2H), 2.23 (s, 3H), 2.15 (s, 3H), 1.82 (d, 3H). [ES + MS] m/z 445 (MH$^+$). |
| 6 | 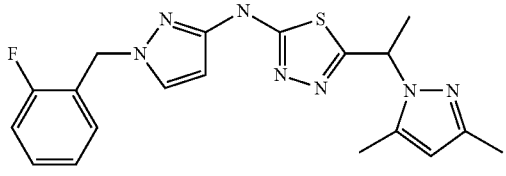<br>5-[1-(3,5-dimethyl-1H-pyrazol-1-yl)ethyl]-N-{1-[(2-fluorophenyl)methyl]-1H-pyrazol-3-yl}-1,3,4-thiadiazol-2-amine<br>See footnote (a) | 71<br>0.343 mmol | 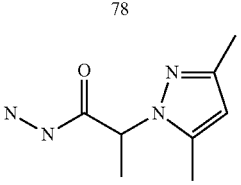<br>0.343 mmol | $^1$H NMR (300 MHz, DMSO-$d_6$) δ ppm: 10.87 (br s, 1H), 7.73 (d, 1H), 7.13-7.25 (m, 3H), 5.97 (d, 1H), 5.85 (s, 1H), 5.77 (q, 1H), 5.26 (br s, 2H), 2.25 (s, 3H), 2.10 (s, 3H), 1.79 (d, 3H). [ES + MS] m/z 448 (MH$^+$). |
| 7 | 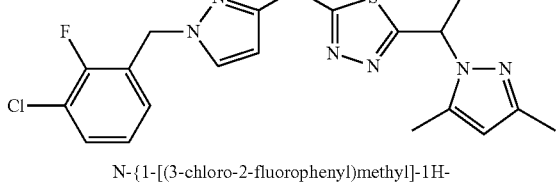<br>N-{1-[(3-chloro-2-fluorophenyl)methyl]-1H-pyrazol-3-yl}-5-[1-(3,5-dimethyl-1H-pyrazol-1-yl)ethyl]-1,3,4-thiadiazol-2-amine | 62<br>0.530 mmol | 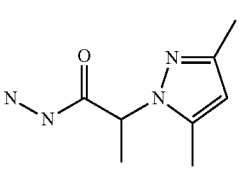<br>0.530 mmol | $^1$H NMR (300 MHz, DMSO-$d_6$) δ ppm: 10.89 (br s, 1H), 7.77 (d, 1H), 7.52-7.58 (m, 1H), 7.17-7.23 (m, 2H), 5.99 (d, 1H), 5.84 (s, 1H), 5.77 (q, 1H), 5.32 (s, 2H), 2.25 (s, 3H), 2.10 (s, 3H), 1.79 (d, 3H). [ES + MS] m/z 432 MH$^+$]. |
| 8 | 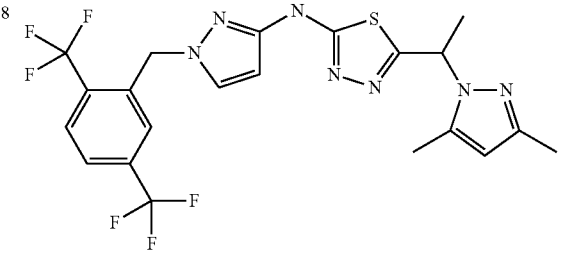<br>N-(1-{[2,5-bis(trifluoromethyl)phenyl]methyl}-1H-pyrazol-3-yl)-5-[1-(3,5-dimethyl-1H-pyrazol-1-yl)ethyl]-1,3,4-thiadiazol-2-amine<br>See footnote (b) | 63<br>0.683 mmol | 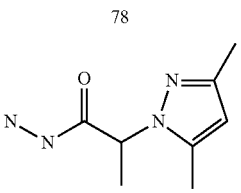<br>0.683 mmol | $^1$H NMR (300 MHz, DMSO-$d_6$) δ ppm: 10.94 (br s, 1H), 7.92-8.05 (m, 2H), 7.86 (d, 1H), 7.45 (s, 1H), 6.04 (d, 1H), 5.72-5.80 (m, 2H), 5.51 (br s, 2H), 2.22 (s, 3H), 2.04 (s, 3H), 1.77 (d, 3H). [ES + MS] m/z 516 (MH$^+$). |

TABLE 1-continued

| Ex. | Structure | Isothiocyanate intermediate | Hydrazide intermediate | Physical data |
|---|---|---|---|---|
| 9 | 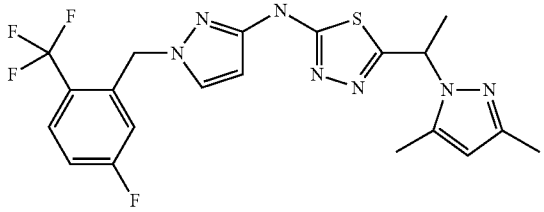<br>5-[1-(3,5-dimethyl-1H-pyrazol-1-yl)ethyl]-N-(1-{[5-fluro-2-(trifluoromethyl)phenyl]methyl}-1H-pyrazol-3-yl)-1,3,4-thiadiazol-2-amine | 64<br>0.531 mmol | 78<br><br>0.531 mmol | $^1$H NMR (300 MHz, DMSO-$d_6$) δ ppm: 10.94 (br s, 1H), 7.82-7.88 (m, 2H), 7.36-7.42 (m, 1H), 6.82-6.84 (m, 1H), 6.03 (d, 1H), 5.75-5.81 (m, 2H), 5.42 (br s, 2H), 2.23 (s, 3H), 2.06 (s, 3H), 1.78 (d, 3H). [ES + MS] m/z 516 (MH$^+$). |
| 10 | 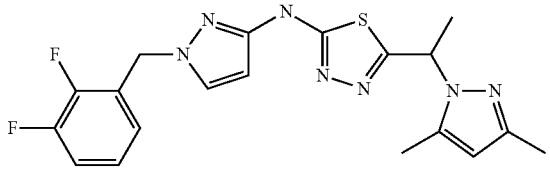<br>N-{1-[(2,3-dichlorophenyl)methyl]-1H-pyrazol-3-yl}-5-[1-(3,5-dimethyl-1H-pyrazol-1-yl)ethyl]-1,3,4-thiadiazol-2-amine<br>See footnote (a) | 65<br>0.8 mmol | 78<br><br>0.8 mmol | $^1$H NMR (300 MHz, DMSO-$d_6$) δ ppm: 10.90 (br s, 1H), 7.77 (d, 1H), 7.01-7.44 (m, 3H), 5.98 (d, 1H), 5.84 (s, 1H), 5.77 (q, 1H), 5.32 (br s, 2H), 2.24 (s, 3H), 2.09 (s, 3H), 1.79 (d, 3H). [ES + MS] m/z 416 (MH$^+$). |
| 11 | 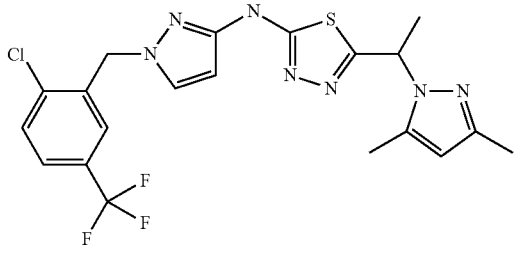<br>N-(1-{[2-chloro-5-(trifluoromethyl)phenyl]methyl}-1H-pyrazol-3-yl)-5-[1-(3,5-dimethyl-1H-pyrazol-1-yl)ethyl]-1,3,4-thiadiazol-2-amine<br>See footnote (a) | 66<br>0.604 mmol | 78<br><br>0.604 mmol | $^1$H NMR (300 MHz, DMSO-$d_6$) δ ppm: 10.92 (br s, 1H), 7.83 (d, 1H), 7.74 (br s, 2H), 7.45 (br s, 1H), 6.01 (d, 1H), 5.75-5.82 (m, 2H), 5.41 (br s, 2H), 2.24 (s, 3H), 2.06 (s, 3H), 1.77 (d, 3H). [ES + MS] m/z 482 (MH$^+$). |
| 12 | 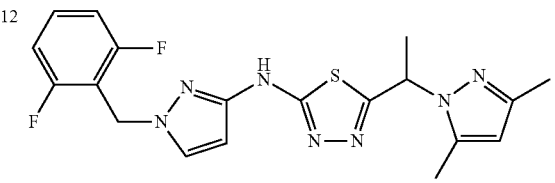<br>N-{1-[(2,6-difluorophenyl)methyl]-1H-pyrazol-3-yl}-5-[1-(3,5-dimethyl-1H-pyrazol-1-yl)ethyl]-1,3,4-thiadiazol-2-amine<br>See footnotes (b) and (d) | 70<br>0.299 mmol | 78<br><br>0.358 mmol | $^1$H NMR (300 MHz, DMSO-$d_6$) δ ppm: 10.84 (br s, 1H), 7.71 (d, 1H), 7.39-7.50 (m, 1H), 7.07-7.12 (m, 2H), 5.92 (d, 1H), 5.86 (s, 1H), 5.75 (q, 1H), 5.24 (s, 2H), 2.24 (s, 3H), 2.11 (s, 3H), 1.78 (d, 3H). [ES + MS] m/z 416 (MH$^+$). |

TABLE 1-continued

| Ex. | Structure | Isothiocyanate intermediate | Hydrazide intermediate | Physical data |
|---|---|---|---|---|
| 13 | N-{1-[(2-fluoro-3-methylphenyl)methyl]-1H-pyrazol-3-yl}-5-[1-(3-methyl-1H-pyrazol-1-yl)ethyl]-1,3,4-thiadiazol-2-amine<br>See footnote (a) | 69<br>0.309 mmol | 0.309 mmol<br>ARTCHEM | $^1$H NMR (300 MHz, DMSO-$d_6$) δ ppm: 10.87 (br s, 1H), 7.74 (d, 1H), 7.71 (d, 1H), 7.19-7.25 (m, 1H), 6.97-7.06 (m, 2H), 6.06 (d, 1H), 5.96 (d, 1H), 5.83 (q, 1H), 5.23 (s, 2H), 2.23 (d, 3H), 2.15 (s, 3H), 1.81 (d, 3H). [ES + MS] m/z 398 (MH$^+$). |
| 14 | N-{1-[(3-chloro-2-fluorophenyl)methyl]-1H-pyrazol-3-yl}-5-[1-(3-methyl-1H-pyrazol-1-yl)ethyl]-1,3,4-thiadiazol-2-amine<br>See footnote (a) | 62<br>0.297 mmol | 0.297 mmol<br>ARTCHEM | $^1$H NMR (300 MHz, DMSO-$d_6$) δ ppm: 10.88 (br s, 1H), 7.77 (d, 1H), 7.74 (d, 1H), 7.51-7.57 (m, 1H), 7.13-7.21 (m, 2H), 6.06 (d, 1H), 5.99 (d, 1H), 5.82 (q, 1H), 5.31 (s, 2H), 2.15 (s, 3H), 1.81 (d, 3H). [ES + MS] m/z 418 (MH$^+$). |
| 15 | N-{1-[(2,3-difluorophenyl)methyl]-1H-pyrazol-3-yl}-5-[1-(3-methyl-1H-pyrazol-1-yl)ethyl]-1,3,4-thiadiazol-2-amine<br>See footnote (a) | 65<br>0.191 mmol | 0.191 mmol<br>ARTCHEM | $^1$H NMR (300 MHz, DMSO-$d_6$) δ ppm: 10.88 (br s, 1H), 7.77 (d, 1H), 7.74 (d, 1H), 7.33-7.43 (m, 1H), 7.12-7.20 (m, 1H), 6.99-7.03 (m, 1H), 6.06 (d, 1H), 5.98 (d, 1H), 5.83 (q, 1H), 5.31 (s, 2H), 2.15 (s, 3H), 1.81 (d, 3H). [ES + MS] m/z 402 (MH$^+$). |
| 16 | N-{1-[(2,3-difluorophenyl)methyl]-1H-pyrazol-3-yl}-5-[1-(4-methyl-1,3-thiazol-2-yl)ethyl]-1,3,4-thiadiazol-2-amine<br>See footnotes (c) and (b) | 65<br>0.178 mmol | 81<br>0.178 mmol | $^1$H NMR (300 MHz, DMSO-$d_6$) δ ppm: 10.89 (br s, 1H), 7.77 (d, 1H), 7.33-7.42 (m, 1H), 7.12-7.21 (m, 2H), 6.99-7.04 (m, 1H), 5.99 (d, 1H), 5.32 (s, 2H), 4.89 (q, 1H) 2.33 (s, 3H), 1.72 (d, 3H). [ES + MS] m/z 419 (MH$^+$). |
| 17 | N-{1-[(2-chloro-4-fluorophenyl)methyl]-1H-pyrazol-3-yl}-5-[1-(3,5-dimethyl-1H-pyrazol-1-yl)ethyl]-1,3,4-thiadiazol-2-amine<br>See footnote (a) | 73<br>0.347 mmol | 78<br>0.347 mmol | $^1$H NMR (300 MHz, DMSO-$d_6$) δ ppm: 7.75 (d, 1H); 7.46-7.49 (m, 1H), 7.18-7.21 (m, 2H), 5.97 (d, 1H), 5.85 (s, 1H), 5.76 (q, 1H), 5.29 (br. s, 2H), 2.25 (s, 3H), 2.09 (s, 3H), 1.79 (d, 3H). [ES + MS] m/z 432 (MH$^+$). |

TABLE 1-continued

| Ex. | Structure | Isothiocyanate intermediate | Hydrazide intermediate | Physical data |
|---|---|---|---|---|
| 18 | 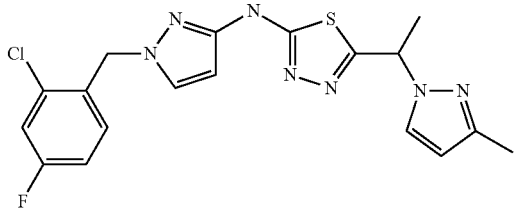<br>N-{1-[(2-chloro-4-fluorophenyl)methyl]-1H-pyrazol-3-yl}-5-[1-(3-methyl-1H-pyrazol-1-yl)ethyl]-1,3,4-thiadiazol-2-amine | 73<br>0.273 mmol | 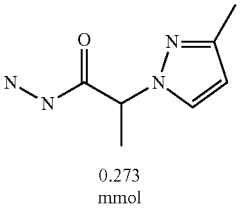<br>0.273 mmol<br>ARTCHEM | $^1$H NMR (300 MHz, DMSO-$d_6$) δ ppm: 10.92 (br. s, 1H), 7.75-7.76 (m, 2H), 7.46-7.50 (m, 1H), 7.17-7.21 (m, 2H), 6.06 (m, 1H), 5.98 (d, 1H), 5.83 (q, 1H), 5.29 (br. s, 2H), 2.16 (s, 3H), 1.82 (d, 3H). [ES + MS] m/z 418 (MH$^+$). |

(a) The initial precipitate did not need EtOAc/water treatment
(b) Precipitate was purified by HPLC preparative using SunFire Chromatography Column (30 mm x 150 mm), Method (40 100) ACN/H2O, in neutral conditions.
(c) Initial precipitate was partitioned between DCM/water.
(d) Product was dissolved in DCM (HPLC grade) and precipitated with Hexane (HPLC grade).

Example 19

N-{1-[(2-chloro-6-fluorophenyl)methyl]-5-methyl-1H-pyrazol-3-yl}-5-[1-(3,5-dimethyl-1H-pyrazol-1-yl)ethyl]-1,3,4-thiadiazol-2-amine

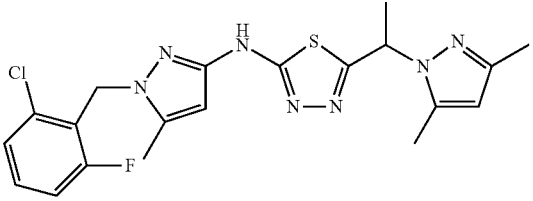 [SMILES: Cc1cc(C)n(C(C)c2nnc(Nc3cc(C)n(Cc4c(F)cccc4Cl)n3)s2)n1]

165 mg of Intermediate 76 (1-[(2-chloro-6-fluorophenyl)methyl]-3-isothiocyanato-5-methyl-1H-pyrazole, 0.586 mmol) were dissolved in 15 mL of anhydrous DCM and 107 mg (0.586 mmol) of Intermediate 78 (2-(3,5-dimethyl-1H-pyrazol-1-yl) propanohydrazide) were added. Mixture was stirred at room temperature for 20 hours and solvent was evaporated to give 267 mg (yield 98%) of N-{1-[(2-chloro-6-fluorophenyl)methyl]-5-methyl-1H-pyrazol-3-yl}-2-[2-(3,5-dimethyl-1H-pyrazol-1-yl) propanoyl]hydrazinecarbothioamide as an orange solid ([ES+MS] m/z 464 (MH$^+$)). The solid was dissolved in 3 mL of H$_2$SO$_4$ (conc) and resultant solution was stirred at room temperature for 2 hours. Reaction was carefully neutralized with aqueous ammonia (32%) until basic precipitate appeared. Precipitate was filtered to give 231 mg of a crude that was purified by silica gel chromatography with gradient DCM/MeOH (1%-10%-20%). 73 mg (yield: 28%) of the title compound as white solid were obtained. A second fraction (163 mg) was purified twice by silica gel chromatography with gradient DCM/MeOH (1%-10%-20%) and after that via preparative HPLC with the following conditions: SUNFIRE C18, 3.5 gm, gradient: water-ACN 60:40 to 0:100 in 20 min, 254 nm. Appropriate fractions were collected to give 30 mg (yield: 12%) of title compound as white solid (total yield: 40%). $^1$H NMR (300 MHz, DMSO-$d_6$) δ ppm: 10.45 (br s, 1H), 7.15-7.44 (m, 3H), 5.85 (s, 1H), 5.76 (s, 1H), 5.69 (q, 1H), 5.20 (d, 2H), 2.35 (s, 3H), 2.24 (s, 3H), 2.13 (s, 3H), 1.79 (d, 3H). [ES+MS] m/z 446 (MH$^+$).

Method B

Example 20

5-[1-(3,5-dimethyl-1H-pyrazol-1-yl)ethyl]-N-{1-[(2-methylphenyl)methyl]-1H-pyrazol-3-yl}-1,3,4-thiadiazol-2-amine

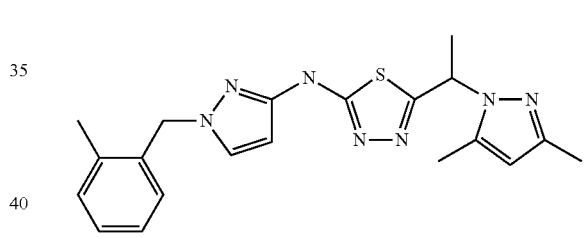

A solution of Intermediate 59 (3-isothiocyanato-1-[(2-methylphenyl)methyl]-1H-pyrazole, 127 mg, 0.554 mmol) and Intermediate 78 2-(3,5-dimethyl-1H-pyrazol-1-yl)propanohydrazide (101 mg, 0.554 mmol) in 5 ml of DCM (anh) was stirred at room temperature during 2 h. Reaction mixture was concentrated under vacuum giving 2-[2-(3,5-dimethyl-1H-pyrazol-1-yl)propanoyl]-N-{1-[(2-methylphenyl)methyl]-1H-pyrazol-3-yl}hydrazinecarbothioamide (223 mg, 0.542 mmol, 98%) as a yellow solid [ES+MS] m/z 412 (MH$^+$). Solid was dissolved in POCl$_3$ (3 mL) and stirred at reflux during 2 h 30 min. Solvent was eliminated under vacuum, and residue was partitioned between DCM and distilled H$_2$O, organic layer was dried over MgSO$_4$ (anh), filtered and concentrated to give a solid that was purified by HPLC preparative using SunFire Chromatography Column (30 mm×150 mm), Method (50_100) ACN/H$_2$O, in neutral conditions to yield the title compound as a white solid (96 mg, 46%). $^1$H NMR (300 MHz, DMSO-$d_6$) 5 ppm: 10.87 (br.s. 1H), 7.68 (d, 1H), 7.10-7.18 (m, 3H), 7.01-7.04 (m, 1H), 5.93 (d, 1H), 5.85 (br.s, 1H), 5.77 (q, 1H), 5.20 (br.s, 2H), 2.35 (s, 3H), 2.25 (s, 3H), 2.11 (s, 3H), 1.79 (d, 3H). [ES+MS] m/z 394 (MH$^+$).

Examples 21-27 were prepared by methods analogous to that described for Example 20 replacing isothiocyanate and hydrazide intermediates with the indicated in Table 2. When the method used for purification was different from that used for Example 20, it is indicated.

TABLE 2

| Ex. | Structure | Isothiocyanate intermediate | Hydrazide intermediate | Physical data |
|---|---|---|---|---|
| 21 | 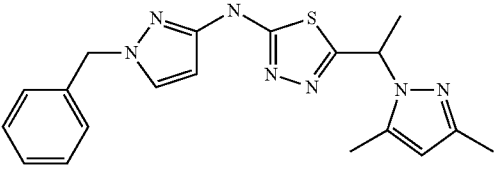 5-[1-(3,5-dimethyl-1H-pyrazol-1-yl)ethyl]-N-[1-(phenylmethyl)-1H-pyrazol-3-yl]-1,3,4-thiadiazol-2-amine See footnote (a) | 72 0.813 mmol | 78 0.813 mmol | $^1$H NMR (300 MHz, DMSO-$d_6$) δ ppm: 10.85 (br s. 1H), 7.74 (d, 1H), 7.24-7.33 (m, 2H) 5.96 (d, 1H), 5.85 (br s, 1H), 5.78 (q, 1H), 5.20 (br s, 2H), 2.25 (s, 3H), 2.10 (s, 3H), 1.80 (d, 3H). [ES + MS] m/z 380 (MH+). |
| 22 | 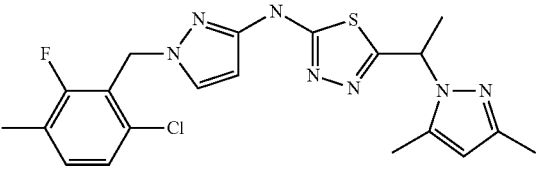 N-{1-[(6-chloro-2-fluoro-3-methylphenyl)methyl]-1H-pyrazol-3-yl}-5-[1-(3,5-dimethyl-1H-pyrazol-1-yl)ethyl]-1,3,4-thiadiazol-2-amine | 67 0.838 mmol | 78 0.838 mmol | $^1$H NMR (300 MHz, DMSO-$d_6$) δ ppm: 10.87 (br s. 1H), 7.71 (d 1H) 7.22-7.34 (m, 2H), 5.90 (d, 1H), 5.85 (br s, 1H), 5.76 (q, 1H), 5.31 (d, 2H), 2.24-2.26 (m, 3H), 2.07-2.11 (m, 3H), 1.80 (d, 3H). [ES + MS] m/z 446 (MH+). |
| 23 | 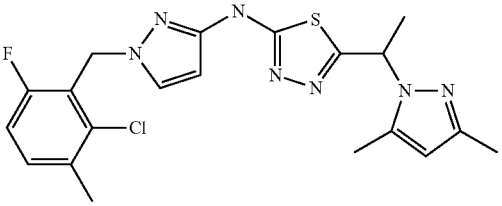 N-{1-[(2-chloro-6-fluoro-3-methylphenyl)methyl]-1H-pyrazol-3-yl}-5-[1-(3,5-dimethyl-1H-pyrazol-1-yl)ethyl]-1,3,4-thiadiazol-2-amine | 68 0.609 mmol | 78 0.609 mmol | 1 H NMR (300 MHz, DMSO-$d_6$) δ ppm: 10.85 (br s, 1H), 7.71 (d, 1H), 7.38-7.43 (m, 1H), 7.13-7.19 (m, 1H), 5.90 (d, 1H), 5.87 (br s, 1H), 5.75 (q, 1H), 5.33 (d, 2H), 2.32 (br s, 3H), 2.26 (br s, 3H), 2.12 (br s, 3H), 1.80 (d, 3H). [ES + MS] m/z 446 (MH+). |
| 24 | 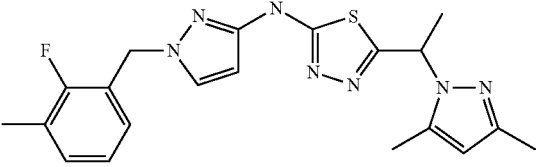 5-[1-(3,5-dimethyl-1H-pyrazol-1-yl)ethyl]-N-{1-[(2-fluoro-3-methylphenyl)methyl]-1H-pyrazol-3-yl}-1,3,4-thiadiazol-2-amine See footnote (a) | 69 0.505 mmol | 78 0.505 mmol | 1 H NMR (300 MHz, DMSO-$d_6$) δ ppm: 10.86 (br s, 1H), 7.72 (d, 1H), 7.20-7.26 (m, 1H), 7.02-7.07 (m, 2H), 5.96 (d, 1H), 5.84 (br s, 1H), 5.77 (q, 1H), 5.24 (d, 2H), 2.25 (br s, 3H), 2.10 (br s, 3H), 1.79 (d, 3H). [ES + MS] m/z 412 (MH+). |
| 25 | 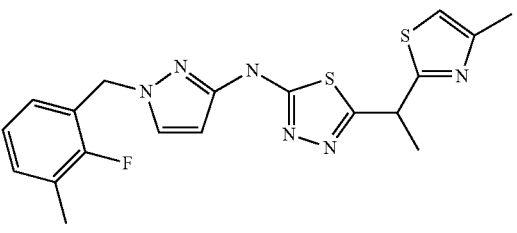 N-{1-[(2-fluoro-3-methylphenyl)methyl]-1H-pyrazol-3-yl}-5-[1-(4-methyl-1,3-thiazol-2-yl)ethyl]-1,3,4-thiadiazol-2-amine See footnote (a) | 69 0.238 mmol | 81 0.238 mmol | $^1$H-NMR (δ, ppm, CDCl$_3$): 7.37 (d, 1H), 7.18-7.13 (m, 1H), 7.04-7.00 (m, 2H), 6.85 (m, 1H), 6.15 (d, 1H), 5.25 (s, 2H), 4.81 (q, 1H), 2.46 (s, 3H), 2.28 (d, 3H), 1.89 (d, 3H). [ES + MS] m/z 421 (MH$^+$) |

TABLE 2-continued

| Ex. | Structure | Isothiocyanate intermediate | Hydrazide intermediate | Physical data |
|---|---|---|---|---|
| 26 | N-{1-[(5-amino-2-chlorophenyl)methyl]-1H-pyrazol-3-yl}-5-[1-(3,5-dimethyl-1H-pyrazol-1-yl)ethyl]-1,3,4-thiadiazol-2-amine<br>See footnote (b) | 74<br>0.244 mmol | 78<br>0.244 mmol | $^1$H NMR (300 MHz, DMSO-d$_6$) δ ppm: 10.88 (br. s, 1H), 7.67 (d, 1H), 7.05 (d, 1H), 6.47-6.50 (m, 1H), 6.02 (d, 1H), 6.19 (d, 1H), 5.83 (br. s, 1H), 5.77 (q, 1H), 5.26 (br. s, 2H), 5.15 (br. s, 2H), 2.25 (s, 3H), 2.09 (s, 3H), 1.79 (d, 3H). [ES + MS] m/z 429 (MH$^+$) |
| 27 | N-{1-[(3-amino-2-methylphenyl)methyl]-1H-pyrazol-3-yl}-5-[1-(3,5-dimethyl-1H-pyrazol-1-yl)ethyl]-1,3,4-thiadiazol-2-amine<br>See footnote (c). | 75<br>0.186 mmol | 78<br>0.186 mmol | $^1$H NMR (300 MHz, DMSO-d$_6$) δ ppm: 10.84 (br. s, 1H), 7.54 (d, 1H), 6.80-6.85 (m, 1H), 6.57-6.60 (m, 1H), 6.30-6.32 (m, 1H), 5.91 (d, 1H), 5.85 (br. s, 1H), 5.78 (q, 1H), 5.12 (br. s, 2H), 4.83 (br. s, 2H), 2.26 (s, 3H), 2.11 (s, 3H), 2.03 (s, 3H), 1.80 (d, 3H),. [ES + MS] m/z 409 (MH$^+$) |

(a) Method (40_100) ACN/H2O, in neutral conditions.
(b) Method (30_100) ACN (0.1% TFA)/H$_2$O (0.1% TFA). Obtaining corresponding salt, that was basified with NH$_3$ (aq, 32%) partitioned between AcOEt/H$_2$O. Organic layer was dried over MgSO$_4$ (anh), filtered and solvent was eliminated.
(c) Method (20_100) ACN/H$_2$O, in neutral conditions.

Method C

Example 28

N-{1-[(2-chloro-6-fluorophenyl)methyl]-1H-pyrazol-3-yl}-5-[1-(3,5-dimethyl-1H-pyrazol-1-yl)ethyl]-1,3,4-thiadiazol-2-amine

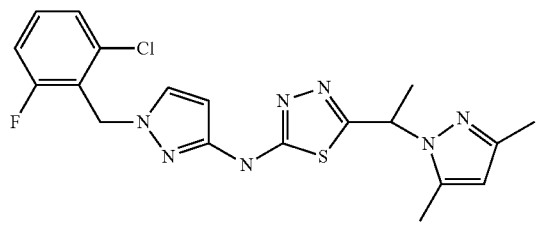 [SMILES: Cc1cc(C)n(C(C)c2nnc(Nc3ccn(Cc4c(F)cccc4Cl)n3)s2)n1]

Intermediate 78 (2-(3,5-dimethyl-1H-pyrazol-1-yl)propanohydrazide, 0.75 g, 4.1 mmol.) and Intermediate 57 (1-[(2-chloro-6-fluorophenyl)methyl]-3-isothiocyanato-1H-pyrazole, 1.1 g, 4.1 mmol.) were suspended in EtOH (30 mL) and the mixture was heated to reflux for 2 h. The white solid formed was then filtered off and washed with EtOH to give a hydrazinecarbothioamide intermediate (1.7 g, 3.8 mmol., 92%, [ES+MS] m/z 450 (MH$^+$)). This intermediate N-{1-[(2-chloro-6-fluorophenyl)methyl]-1H-pyrazol-3-yl}-2-[2-(3,5-dimethyl-1H-pyrazol-1-yl)propanoyl]hydrazinecarbothioamide (1.65 g, 3.7 mmol.) was dissolved in concentrated H$_2$SO$_4$ (15 mL) and the mixture was stirred for 2 h. Dropwise neutralisation with 33% aq. NH$_3$ under ice-bath temperature yielded a white precipitate that was filtered off and dried under vacuum to give the title compound as a white solid (1.26 g, 2.9 mmol., 78.4%). $^1$H NMR (300 MHz, CDCl$_3$) δ ppm: 7.21-7.34 (m, 3H), 7.05 (m, 1H), 5.98 (d, 1H), 5.82 (d, 1H), 5.69 (q, 1H), 5.36 (d, 2H), 2.30 (s, 3H), 2.26 (s, 3H), 1.99 (d, 2H); [ES+MS] m/z: 432 (MH$^+$).

Examples 29-33 were prepared by methods analogous to that described for Example 28 but replacing the isothiocyanate and hydrazide intermediates with those indicated in Table 3. When during neutralisation the solid was not filtered, the purification process is indicated as a footnote.

TABLE 3

| Ex. | Structure | Isothiocyanate intermediate | Hydrazide intermediate | Physical data |
|---|---|---|---|---|
| 29 | 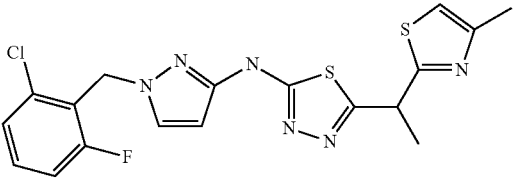<br>N-{1-[(2-chloro-6-fluorophenyl)methyl]-1H-pyrazol-3-yl}-5-[1-(4-methyl-1,3-thiazol-2-yl)ethyl]-1,3,4-thiadiazol-2-amine<br>See footnote (a) | 57<br>0.702 mmol | 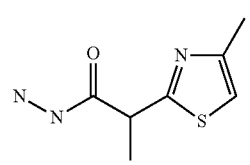<br>81<br>0.702 mmol | $^1$H NMR (300 MHz, DMSO-$d_6$) δ ppm: 7.71 (s, 1H), 7.46-7.21 (m, 5H), 5.92 (d, 1H), 5.32 (s, 2H), 4.87 (q, 1H), 2.35 (s, 3H), 1.71 (d, 3H). [ES + MS] m/z 435 (MH$^+$) |
| 30 | 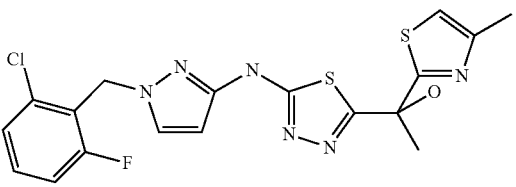<br>1-[5-({1-[(2-chloro-6-fluorophenyl)methyl]-1H-pyrazol-3-yl}amino)-1,3,4-thiadiazol-2-yl]-1-(4-methyl-1,3-thiazol-2-yl)ethanol<br>See footnote (a) | 57<br>0.328 mmol | 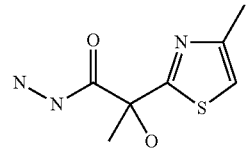<br>82<br>0.328 mmol | $^1$H NMR (300 MHz, DMSO-$d_6$) δ ppm: 10.84 (s, 1H), 7.69 (s, 1H), 7.43-7.21 (m, 5H), 5.90 (d, 1H), 5.32 (s, 2H), 2.29 (s, 3H), 1.97 (s, 3H). [ES + MS] m/z 451 (MH$^+$) |
| 31 | 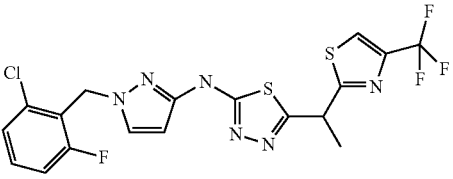<br>N-{1-[(2-chloro-6-fluorophenyl)methyl]-1H-pyrazol-3-yl}-5-{1-[4-(trifluoromethyl)-1,3-thiazol-2-yl]ethyl}-1,3,4-thiadiazol-2-amine | 57<br>0.773 mmol | 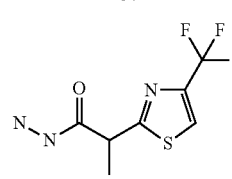<br>84<br>0.773 mmol | $^1$H NMR (300 MHz, DMSO-$d_6$) δ ppm: 8.50 (s, 1H), 7.72 (s, 1H), 7.45-7.20 (m, 4H), 5.92 (d, 1H), 5.33 (s, 2H), 5.06 (q, 1H), 1.76 (d, 3H). [ES + MS] m/z 489 (MH$^+$) |
| 32 | 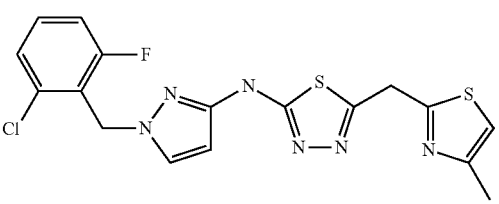<br>N-{1-[(2-chloro-6-fluorophenyl)methyl]-1H-pyrazol-3-yl}-5-[(4-methyl-1,3-thiazol-2-yl)methyl]-1,3,4-thiadiazol-2-amine | 57<br>0.209 mmol | 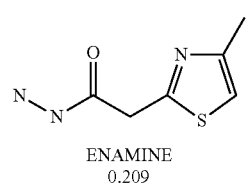<br>ENAMINE<br>0.209 mmol | $^1$H NMR (300 MHz, CDCl$_3$) δ ppm: 7.36-7.20 (m, 4H), 7.07-7.01 (m, 1H), 6.83 (m, 1H), 6.01 (d, 1H), 5.36 (d, 2H), 4.66 (s, 2H), 2.48 (s, 3H). [ES + MS] m/z 415 (MH$^+$) |

TABLE 3-continued

| Ex. | Structure | Isothiocyanate intermediate | Hydrazide intermediate | Physical data |
|---|---|---|---|---|
| 33 | 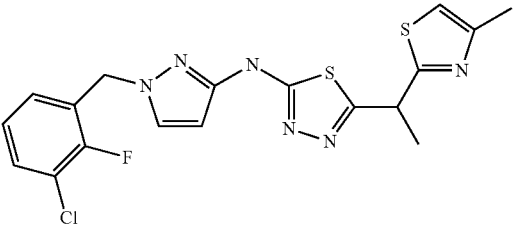<br>N-{1-[(3-chloro-2-fluorophenyl)methyl]-1H-pyrazol-3-yl}-5-[1-(4-methyl-1,3-thiazol-2-yl)ethyl]-1,3,4-thiadiazol-2-amine<br>See footnote (b) | 62<br>0.238 mmol | 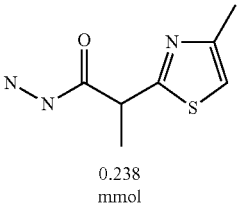<br>81<br>0.238 mmol | $^1$H NMR (300 MHz, DMSO-$d_6$) δ ppm: 10.90 (s, 1H), 7.66 (d, 1H), 7.56-7.50 (m, 1H), 7.20-7.15 (m, 3H), 5.99 (d, 1H), 5.31 (s, 2H), 4.88 (q, 1H), 2.33 (s, 3H), 1.72 (d, 3H). [ES + MS] m/z 435 (MH$^+$) |

(a) Resulting suspension was diluted with EtOAc and water. Organic phase was separated, washed with brine, dried over sodium sulphate and concentrated Crude was purified by chromatography on silica gel using a DCM/MeOH gradient to yield title compound.
(b) Aqueous mixture was extracted with ethyl acetate. Organic extract was washed with brine, dried over sodium sulphate and concentrated. Residue was triturated with ethyl ether and resulting solid was filtered and washed with ethyl ether.

Example 34

N-{1-[(4-chlorophenyl)methyl]-1H-pyrazol-3-yl}-5-[1-(3,5-dimethyl-1H-pyrazol-1-yl)ethyl]-1,3,4-thiadiazol-2-amine

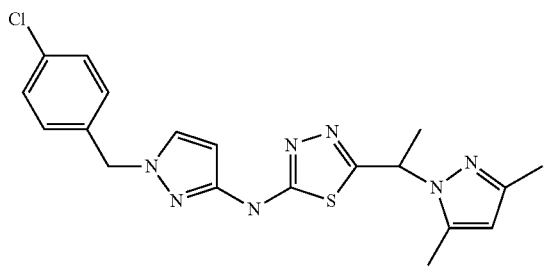 [SMILES: Cc1cc(C)n(C(C)c2nnc(Nc3ccn(Cc4ccc(Cl)cc4)n3)s2)n1]

Intermediate 50 (1-[(4-chlorophenyl)methyl]-1H-pyrazol-3-amine, 63 mg, 0.3 mmol.) was dissolved in a mixture of chloroform (1.2 mL) and aq. NaHCO$_3$ (sat.) (1.2 mL). Thiophosgene (41 mg, 0.36 mmol.) was then added and the mixture was vigorously stirred for 10 min. The organic phase was then separated off by means of an hydrophobic frit and was concentrated to dryness to give a pale yellowish oil (72 mg, [ES+MS] m/z: 250 (MH$^+$)). The crude oil and Intermediate 78 (53 mg, 0.29 mmol.) were dissolved in DCM (6 mL) and the mixture was stirred for 1 h 30 min. The resulting solution was concentrated to dryness to give a pale yellow oil (125 mg, [ES+MS] m/z: 432 (MH$^+$)) that was dissolved in concentrated H$_2$SO$_4$ (10 mL) and stirred at r.t. for 1 h 30 min. The resulting solution was carefully neutralised at ice-cold temperature with 28% aq. solution of NH$_3$ with formation of a white precipitate. The formed solids were filtered off, washed with water (2×) and dried under vacuum to give the title compound as a white solid (35 mg, 30%). $^1$H NMR (300 MHz, DMSO-$d_6$) δ ppm: 10.87 (s, 1H), 7.74 (d, 1H), 7.37 (d, 2H), 7.24 (d, 2H), 5.95 (d, 1H), 5.84 (s, 1H), 5.76 (q, 1H), 5.20 (s, 2H), 2.24 (s, 3H), 2.09 (s, 2H), 1.78 (d, 3H); [ES+MS] m/z: 414 (M$^+$).

Example 35

5-[1-(3,5-dimethyl-1H-pyrazol-1-yl)ethyl]-N-(1-{[4-(trifluoromethyl)phenyl]methyl}-1H-pyrazol-3-yl)-1,3,4-thiadiazol-2-amine

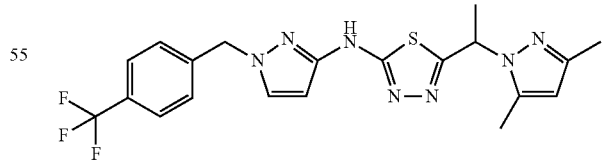

The compound was prepared starting from Intermediate 54 in an analogous manner to Example 34. $^1$H NMR (300 MHz, DMSO-$d_6$) δ ppm: 7.78 (d, 1H), 7.67 (d, 2H), 7.42 (d, 2H), 5.98 (d, 1H), 5.82 (s, 1H), 5.76 (q, 1H), 5.33 (s, 2H), 2.23 (s, 3H), 2.06 (s, 2H), 1.78 (d, 3H); [ES+MS] m/z: 448 (MH+).

Example 36

N-{1-[(2-chloro-5-fluorophenyl)methyl]-1H-pyrazol-3-yl}-5-[1-(3,5-dimethyl-1H-pyrazol-1-yl)ethyl]-1,3,4-thiadiazol-2-amine

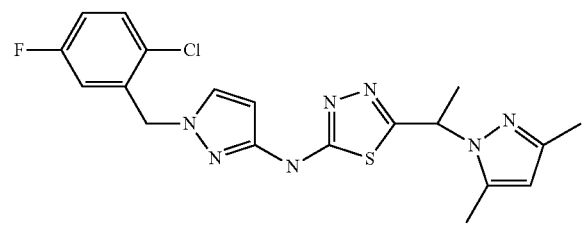 [SMILES: Cc1cc(C)n(C(C)c2nnc(Nc3ccn(Cc4cc(F)ccc4Cl)n3)s2)n1]

Intermediate 21 (N-{1-[(2-chloro-5-fluorophenyl)methyl]-1H-pyrazol-3-yl}acetamide, 320 mg, 1.2 mmol.) was dissolved in EtOH (10 mL) and aq. 25% NaOH (14 mL) was added and the mixture was heated to reflux overnight. The volatile EtOH was evaporated off, and the aqueous solution was further dissolved in aq. sat. NaCl. The aqueous layer was then extracted with EtOAc (3×15 mL), dried over $Na_2SO_4$ and concentrated to dryness to give a colourless oil (197 mg, [ES+MS] m/z: 226 (MH+)). The oil was dissolved in a mixture of chloroform (5 mL) and aq. sat. $NaHCO_3$ (5 mL). To the resulting solution, thiophosgene (120 mg, 1.04 mmol.) was added and the mixture was allowed to react for 20 min. The organic layer was then separated off by means of an hydrophobic frit and concentrated under vacuum to give a pale yellow oil (248 mg, [ES+MS] m/z: 268 (MH+)). This crude and Intermediate 78 (110 mg, 0.93 mmol) were dissolved in DCM (10 mL) and the mixture was allowed to react overnight. The resulting solution was concentrated to dryness and suspended in concentrated $H_2SO_4$ (15 mL) and stirred at r.t. for 2 h. The resulting solution was carefully neutralised at ice-cold temperature with 28% aq. solution of $NH_3$ with formation of a white precipitate. The formed solids were filtered off, washed with water (2×) and dried under vacuum and purified by HPLC (Agilent 1200, Sunfire-19, 40 to 100% ACN/water, 21 min) to give the title compound as a white solid (95 mg, 18%). $^1$H NMR (300 MHz, DMSO-$d_6$) δ ppm: 10.91 (br s, 1H), 7.78 (d, 1H), 7.52 (dd, 1H), 7.22 (m, 1H), 6.89 (m, 1H), 5.99 (d, 1H), 5.82 (s, 1H), 5.75 (q, 1H), 5.30 (s, 2H), 2.23 (s, 3H), 2.07 (s, 3H), 1.77 (d, 2H); [ES+MS] m/z: 433 (MH+).

Example 37

N-{1-[(2-chloro-6-fluorophenyl)methyl]-1H-pyrazol-3-yl}-5-[(3,5-dimethyl-1H-pyrazol-1-yl)methyl]-1,3-thiazol-2-amine

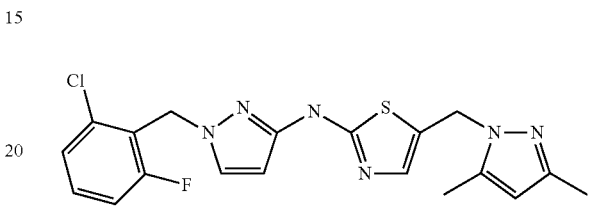

Over a solution of Intermediate 85 (2-chloro-5-[(3,5-dimethyl-1H-pyrazol-1-yl)methyl]-1,3-thiazole, 40 mg, 0.18 mmol) in Toluene (1 ml), 1-[(2-chloro-6-fluorophenyl)methyl]-1H-pyrazol-3-amine (ARTCHEM, 44 mg, 0.19 mmol), sodium t-butoxide (25 mg, 0.26 mmol), BINAP (7 mg, 0.011 mmol) and $Pd_2(dba)_3$ (5 mg, 0.006 mmol) were added successively. The resulting suspension was deoxygenated by bubbling argon for 5 minutes and heated in a sealed vessel in the microwave for 30 min at 120° C. The reaction mixture was filtered, Toluene was evaporated and the residue purified by chromatography (silica gel cartridge, Hex/EtOAc) to afford the title compound. $^1$H NMR (300 MHz, DMSO-$d_6$) 5 ppm: 7.65 (s, 1H); 7.44-7.24 (m, 3H); 7.11 (s, 1H), 5.94 (s, 1H); 5.78 (s, 1H); 5.32 (s, 2H); 5.17 (s, 2H); 2.27 (s, 3H); 2.07 (s, 3H). [ES+MS] m/z: 417 (MH+).

The following compounds in Table 4 (Examples 38 to 65) were purchased from ARTCHEM and tested in the InhA enzymatic and TB growth inhibition assays. Those compounds can be prepared using analogous procedures to those described above.

TABLE 4

| Example | Structure | Name |
| --- | --- | --- |
| 38 | ![structure] | N-{1-[(2-chloro-6-fluorophenyl)methyl]-1H-pyrazol-3-yl}-5-[1-(3-methyl-1H-pyrazol-1-yl)ethyl]-1,3,4-thiadiazol-2-amine |
| 39 | ![structure] | N-{1-[(2-chloro-6-fluorophenyl)methyl]-1H-pyrazol-3-yl}-5-[(3-methyl-1H-pyrazol-1-yl)methyl]-1,3,4-thiadiazol-2-amine |

TABLE 4-continued

| Example | Structure | Name |
|---|---|---|
| 40 | 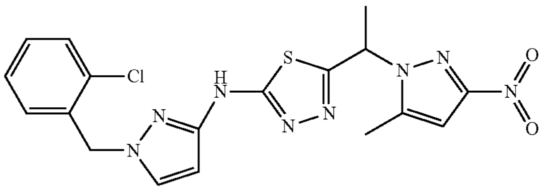 [SMILES: Cc1cc([N+](=O)[O-])nn1C(C)c1nnc(Nc2ccn(Cc3ccccc3Cl)n2)s1] | N-{1-[(2-chlorophenyl)methyl]-1H-pyrazol-3-yl}-5-[1-(5-methyl-3-nitro-1H-pyrazol-1-yl)ethyl]-1,3,4-thiadiazol-2-amine |
| 41 | 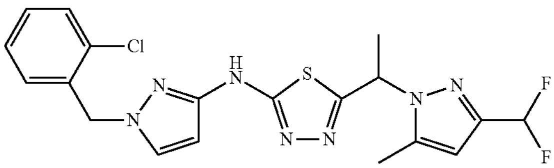 [SMILES: Cc1cc(C(F)F)nn1C(C)c1nnc(Nc2ccn(Cc3ccccc3Cl)n2)s1] | N-{1-[(2-chlorophenyl)methyl]-1H-pyrazol-3-yl}-5-{1-[3-(difluoromethyl)-5-methyl-1H-pyrazol-1-yl]ethyl}-1,3,4-thiadiazol-2-amine |
| 42 | 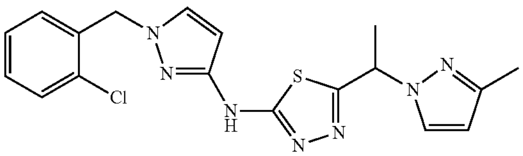 [SMILES: Cc1ccn(C(C)c2nnc(Nc3ccn(Cc4ccccc4Cl)n3)s2)n1] | N-{1-[(2-chlorophenyl)methyl]-1H-pyrazol-3-yl}-5-[1-(3-methyl-1H-pyrazol-1-yl)ethyl]-1,3,4-thiadiazol-2-amine |
| 43 | 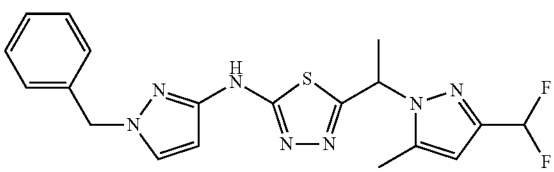 [SMILES: Cc1cc(C(F)F)nn1C(C)c1nnc(Nc2ccn(Cc3ccccc3)n2)s1] | 5-{1-[3-(difluoromethyl)-5-methyl-1H-pyrazol-1-yl]ethyl}-N-[1-(phenylmethyl)-1H-pyrazol-3-yl]-1,3,4-thiadiazol-2-amine |
| 44 | 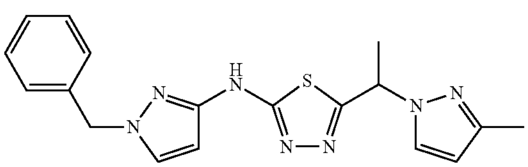 [SMILES: Cc1ccn(C(C)c2nnc(Nc3ccn(Cc4ccccc4)n3)s2)n1] | 5-[1-(3-methyl-1H-pyrazol-1-yl)ethyl]-N-[1-(phenylmethyl)-1H-pyrazol-3-yl]-1,3,4-thiadiazol-2-amine |
| 45 | 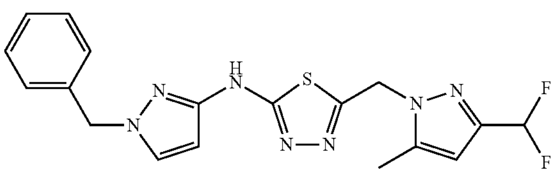 [SMILES: Cc1cc(C(F)F)nn1Cc1nnc(Nc2ccn(Cc3ccccc3)n2)s1] | 5-{[3-(difluoromethyl)-5-methyl-1H-pyrazol-1-yl]methyl}-N-[1-(phenylmethyl)-1H-pyrazol-3-yl]-1,3,4-thiadiazol-2-amine |
| 46 | 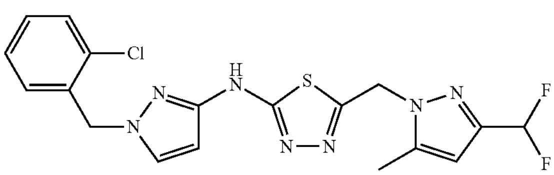 [SMILES: Cc1cc(C(F)F)nn1Cc1nnc(Nc2ccn(Cc3ccccc3Cl)n2)s1] | N-{1-[(2-chlorophenyl)methyl]-1H-pyrazol-3-yl}-5-{[3-(difluoromethyl)-5-methyl-1H-pyrazol-1-yl]methyl}-1,3,4-thiadiazol-2-amine |
| 47 | 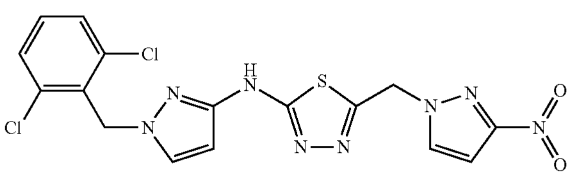 [SMILES: O=[N+]([O-])c1ccn(Cc2nnc(Nc3ccn(Cc4c(Cl)cccc4Cl)n3)s2)n1] | N-{1-[(2,6-dichlorophenyl)methyl]-1H-pyrazol-3-yl}-5-[(3-nitro-1H-pyrazol-1-yl)methyl]-1,3,4-thiadiazol-2-amine |
| 48 | 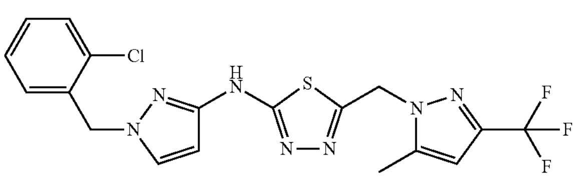 [SMILES: Cc1cc(C(F)(F)F)nn1Cc1nnc(Nc2ccn(Cc3ccccc3Cl)n2)s1] | N-{1-[(2-chlorophenyl)methyl]-1H-pyrazol-3-yl}-5-{[5-methyl-3-(trifluoromethyl)-1H-pyrazol-1-yl]methyl}-1,3,4-thiadiazol-2-amine |

TABLE 4-continued

| Example | Structure | Name |
|---|---|---|
| 49 | 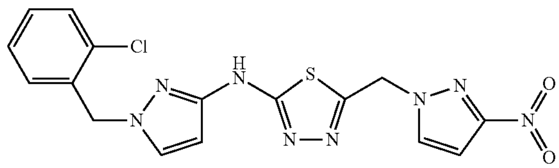 [SMILES: O=[N+]([O-])c1ccn(Cc2nnc(Nc3ccn(Cc4ccccc4Cl)n3)s2)n1] | N-{1-[(2-chlorophenyl)methyl]-1H-pyrazol-3-yl}-5-[(3-nitro-1H-pyrazol-1-yl)methyl]-1,3,4-thiadiazol-2-amine |
| 50 | 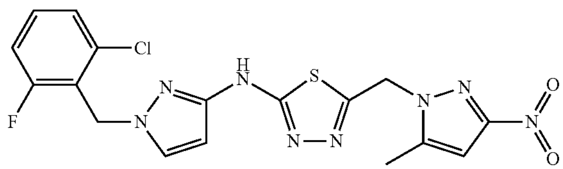 [SMILES: Cc1cc([N+](=O)[O-])nn1Cc1nnc(Nc2ccn(Cc3c(F)cccc3Cl)n2)s1] | N-{1-[(2-chloro-6-fluorophenyl)methyl]-1H-pyrazol-3-yl}-5-[(5-methyl-3-nitro-1H-pyrazol-1-yl)methyl]-1,3,4-thiadiazol-2-amine |
| 51 | 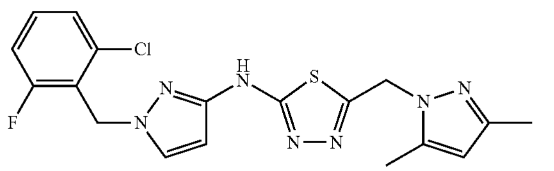 [SMILES: Cc1cc(C)n(Cc2nnc(Nc3ccn(Cc4c(F)cccc4Cl)n3)s2)n1] | N-{1-[(2-chloro-6-fluorophenyl)methyl]-1H-pyrazol-3-yl}-5-[(3,5-dimethyl-1H-pyrazol-1-yl)methyl]-1,3,4-thiadiazol-2-amine |
| 52 | 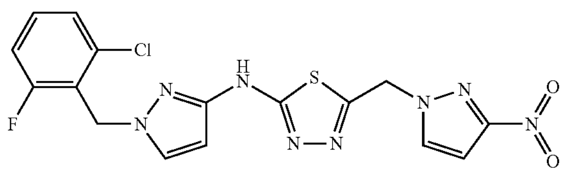 [SMILES: O=[N+]([O-])c1ccn(Cc2nnc(Nc3ccn(Cc4c(F)cccc4Cl)n3)s2)n1] | N-{1-[(2-chloro-6-fluorophenyl)methyl]-1H-pyrazol-3-yl}-5-[(3-nitro-1H-pyrazol-1-yl)methyl]-1,3,4-thiadiazol-2-amine |
| 53 | 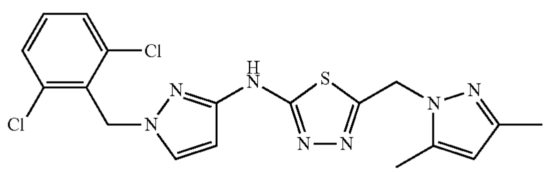 [SMILES: Cc1cc(C)n(Cc2nnc(Nc3ccn(Cc4c(Cl)cccc4Cl)n3)s2)n1] | N-{1-[(2,6-dichlorophenyl)methyl]-1H-pyrazol-3-yl}-5-[(3,5-dimethyl-1H-pyrazol-1-yl)methyl]-1,3,4-thiadiazol-2-amine |
| 54 | 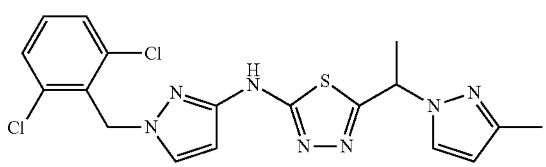 [SMILES: Cc1ccn(C(C)c2nnc(Nc3ccn(Cc4c(Cl)cccc4Cl)n3)s2)n1] | N-{1-[(2,6-dichlorophenyl)methyl]-1H-pyrazol-3-yl}-5-[1-(3-methyl-1H-pyrazol-1-yl)ethyl]-1,3,4-thiadiazol-2-amine |
| 55 | 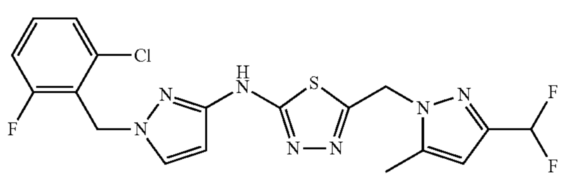 | N-{1-[(2-chloro-6-fluorophenyl)methyl]-1H-pyrazol-3-yl}-5-([3-(difluoromethyl)-5-methyl-1H-pyrazol-1-yl]methyl}-1,3,4-thiadiazol-2-amine |
| 56 | 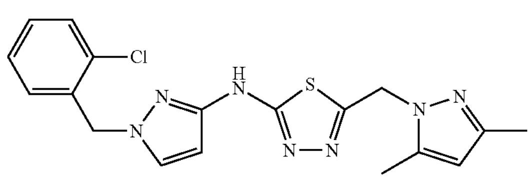 [SMILES: Cc1cc(C)n(Cc2nnc(Nc3ccn(Cc4ccccc4Cl)n3)s2)n1] | N-{1-[(2-chlorophenyl)methyl]-1H-pyrazol-3-yl}-5-[(3,5-dimethyl-1H-pyrazol-1-yl)methyl]-1,3,4-thiadiazol-2-amine |
| 57 | 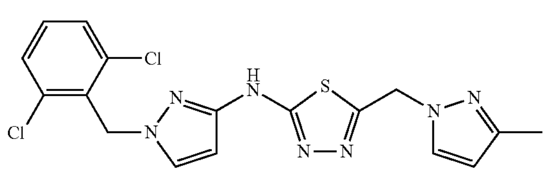 [SMILES: Cc1ccn(Cc2nnc(Nc3ccn(Cc4c(Cl)cccc4Cl)n3)s2)n1] | N-{1-[(2,6-dichlorophenyl)methyl]-1H-pyrazol-3-yl}-5-[(3-methyl-1H-pyrazol-1-yl)methyl]-1,3,4-thiadiazol-2-amine |

TABLE 4-continued

| Example | Structure | Name |
|---|---|---|
| 58 | 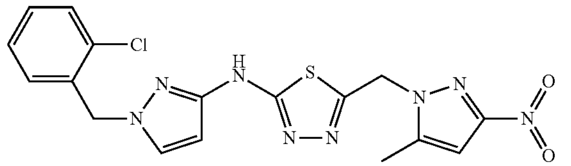 [SMILES: Cc1cc([N+](=O)[O-])nn1Cc1nnc(Nc2ccn(Cc3ccccc3Cl)n2)s1] | N-{1-[(2-chlorophenyl)methyl]-1H-pyrazol-3-yl}-5-[(5-methyl-3-nitro-1H-pyrazol-1-yl)methyl]-1,3,4-thiadiazol-2-amine |
| 59 | 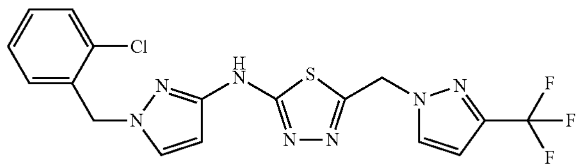 | N-{1-[(2-chlorophenyl)methyl]-1H-pyrazol-3-yl}-5-{[3-(trifluoromethyl)-1H-pyrazol-1-yl]methyl}-1,3,4-thiadiazol-2-amine |
| 60 | 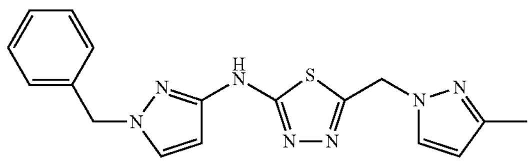 [SMILES: Cc1ccn(Cc2nnc(Nc3ccn(Cc4ccccc4)n3)s2)n1] | 5-[(3-methyl-1H-pyrazol-1-yl)methyl]-N-[1-(phenylmethyl)-1H-pyrazol-3-yl]-1,3,4-thiadiazol-2-amine |
| 61 | 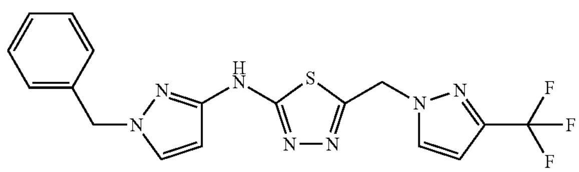 [SMILES: FC(F)(F)c1ccn(Cc2nnc(Nc3ccn(Cc4ccccc4)n3)s2)n1] | N-[1-(phenylmethyl)-1H-pyrazol-3-yl]-5-{[3-(trifluoromethyl)-1H-pyrazol-1-yl]methyl}-1,3,4-thiadiazol-2-amine |
| 62 | 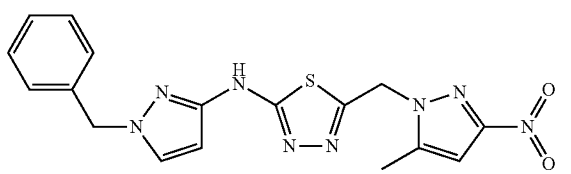 [SMILES: Cc1cc([N+](=O)[O-])nn1Cc1nnc(Nc2ccn(Cc3ccccc3)n2)s1] | 5-[(5-methyl-3-nitro-1H-pyrazol-1-yl)methyl]-N-[1-(phenylmethyl)-1H-pyrazol-3-yl]-1,3,4-thiadiazol-2-amine |
| 63 | 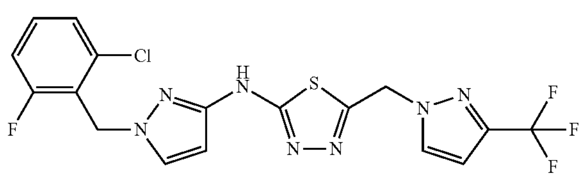 [SMILES: Fc1cccc(Cl)c1Cn1ccc(Nc2nnc(Cn3ccc(C(F)(F)F)n3)s2)n1] | N-{1-[(2-chloro-6-fluorophenyl)methyl]-1H-pyrazol-3-yl}-5-{[3-(trifluoromethyl)-1H-pyrazol-1-yl]methyl}-1,3,4-thiadiazol-2-amine |
| 64 | 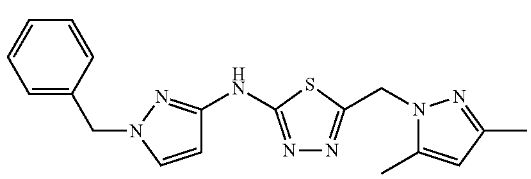 [SMILES: Cc1cc(C)n(Cc2nnc(Nc3ccn(Cc4ccccc4)n3)s2)n1] | 5-[(3,5-dimethyl-1H-pyrazol-1-yl)methyl]-N-[1-(phenylmethyl)-1H-pyrazol-3-yl]-1,3,4-thiadiazol-2-amine |
| 65 | 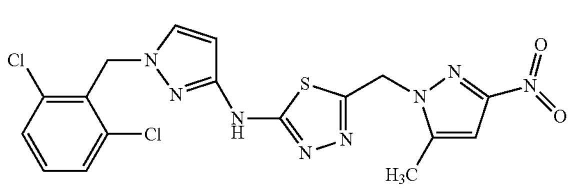 [SMILES: Cc1cc([N+](=O)[O-])nn1Cc1nnc(Nc2ccn(Cc3c(Cl)cccc3Cl)n2)s1] | N-{1-[(2,6-dichlorophenyl)methyl]-1H-pyrazol-3-yl}-5-[1-(5-methyl-3-nitro-1H-pyrazol-1-yl)methyl]-1,3,4-thiadiazol-2-amine |

Chiral Separation of Racemate Example 38

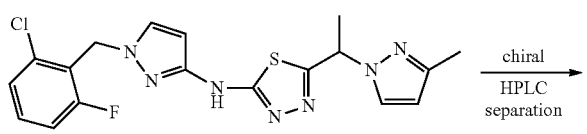

Example 38

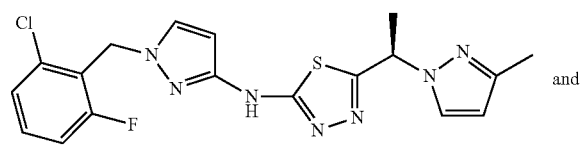

Isomer 1
Example 66

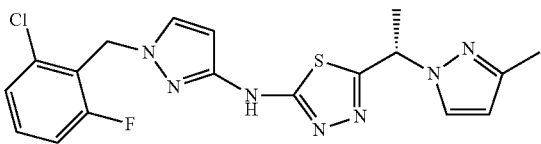

Isomer 2
Example 67

38 mg of Example 38 (racemic mixture) were separated using mixture of hexanes-ethanol 40:60 with a CHIRAL-PAK-AD 20×250 mm column, F=17 mL/min, 254 nm. 38 mg were dissolved in a mixture of 3 mL of ethanol/isopropanol/methanol with heating (product is very insoluble). 4 injections were needed to purify the whole sample. Between injections dissolved sample started to precipitate so additional heating before each injection was needed. Separation was achieved and appropriate fractions were collected to afford both enantiomers that were additionally purified using a 1 g silica gel cartridge and a mixture DCM/MeOH (both solvents HPLC grade) 25:1.

Example 66

N-{1-[(2-chloro-6-fluorophenyl)methyl]-1H-pyrazol-3-yl}-5-[(1R)-1-(3-methyl-1H-pyrazol-1-yl)ethyl]-1,3,4-thiadiazol-2-amine Isomer 1

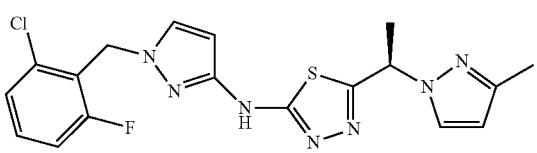

Isomer 1, first elution in HPLC: 10.5 mg, white solid. $^1$H NMR (300 MHz, CDCl$_3$) δ ppm: 7.41 (d, 1H), 7.36 (d, 1H), 7.22-7.32 (m, 3H), 7.02-7.09 (m, 1H), 6.09 (d, 1H), 6.01 (d, 1H), 5.76 (q, 1H), 5.38 (d, 2H), 2.35 (s, 3H), 2.02 (d, 3H). [ES+MS] m/z 418 (MH$^+$). Analytical Chiral HPLC conditions: CHIRALPAK-AD 4.6×150 mm column, method: eluent isocratic mixture ACN 0.1% isoprylamine/MeOH 0.1% isopropylamine ratio 85/15, flow: 1 mL/min. Rt: 4.43 min. αD=+0.88°. The absolute configurations were determined by ab initio vibrational circular dichroism (VCD)

Example 67

N-{1-[(2-chloro-6-fluorophenyl)methyl]-1H-pyrazol-3-yl}-5-[(1S)-1-(3-methyl-1H-pyrazol-1-yl)ethyl]-1,3,4-thiadiazol-2-amine Isomer 2

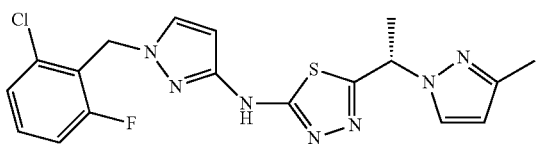

Isomer 2, second elution in HPLC: 10.5 mg, white solid. $^1$H NMR (300 MHz, CDCl$_3$) δ ppm: 7.42 (d, 1H), 7.37 (d, 1H), 7.22-7.32 (m, 3H), 7.03-7.09 (m, 1H), 6.09 (d, 1H), 5.99 (d, 1H), 5.76 (q, 1H), 5.38 (d, 2H), 2.35 (s, 3H), 2.02 (d, 3H). [ES+MS] m/z 418 (MH$^+$). Analytical Chiral HPLC conditions: CHIRALPAK-AD 4.6×150 mm column, method: eluent isocratic mixture ACN 0.1% isoprylamine/MeOH 0.1% isopropylamine ratio 85/15, flow: 1 mL/min. Rt: 6.70 min. αD=−1.47°. The absolute configurations were determined by ab initio vibrational circular dichroism (VCD)

Chiral Separation of Racemate Example 28

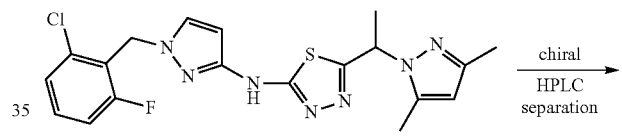

Example 28

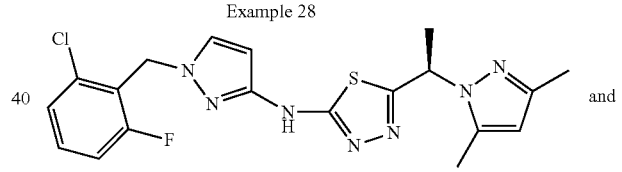

Isomer 1
Example 68

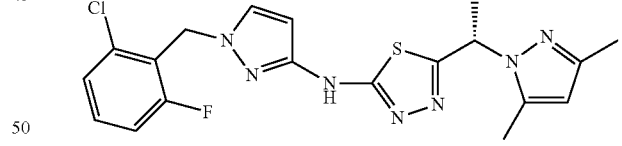

Isomer 2
Example 69

20 mg of Example 28 (racemic mixture) were separated using mixture of hexanes-ethanol 50:50 with a CHIRAL-PAK-AD 20×250 mm column, F=17 mL/min, 254 nm. 20 mg were dissolved in a mixture of 32 mL of ethanol/isopropanol/methanol (methanol is the major solvent; product is highly insoluble) with heating. 16 injections were needed to purify the whole sample. Between injections dissolved sample started to precipitate so additional heating before each injection was needed. Separation was achieved and appropriate fractions were collected to afford both enantiomers that were additionally purified first using a 500 mg silica gel cartridge with mixtures DCM/MeOH (both solvents HPLC grade) 25:1 and finally, using reverse phase preparative HPLC (column SUNFIRE 19×150 mm, 3.5 mm; gradient H₂O-acetonitrile: 0 min 60:40; 3 min 60:40; 15 min 0:100; 20 min 0:100; 254 nm; F=17 mL/min. Appropriate fractions were collected to afford:

Example 68

N-{1-[(2-chloro-6-fluorophenyl)methyl]-1H-pyrazol-3-yl}-5-[(1R)-1-(3,5-dimethyl-1H-pyrazol-1-yl)ethyl]-1,3,4-thiadiazol-2-amine Isomer 1

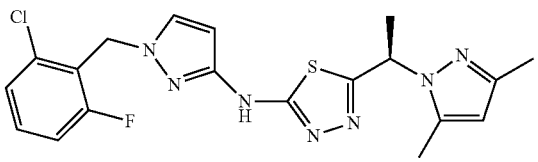

Isomer 1, first elution in HPLC: 3.5 mg, white solid. ¹H NMR (300 MHz, CDCl₃) δ ppm: 7.36 (d, 1H), 7.22-7.33 (m, 3H), 7.04-7.10 (m, 1H), 5.97 (d, 1H), 5.83 (s, 1H), 5.70 (q, 1H), 5.38 (d, 2H), 2.30 (s, 3H), 2.27 (s, 3H), 2.00 (d, 3H). [ES+MS] m/z 432 (MH⁺). Analytical Chiral HPLC conditions: CHIRALPAK-AD 4.6×150 mm column, method: eluent isocratic mixture ACN 0.1% isoprylamine/MeOH 0.1% isopropylamine ratio 85/15, flow: 1 mL/min. Rt: 2.67 min Example 69

N-{1-[(2-chloro-6-fluorophenyl)methyl]-1H-pyrazol-3-yl}-5-[(1S)-1-(3,5-dimethyl-1H-pyrazol-1-yl)ethyl]-1,3,4-thiadiazol-2-amine Isomer 2

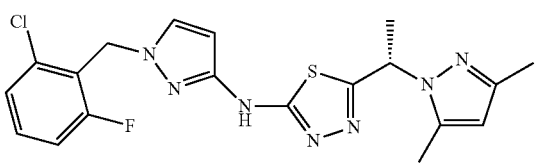

Isomer 2, second elution in HPLC: 1.7 mg, white solid. ¹H NMR (300 MHz, CDCl₃) δ ppm: 7.36 (d, 1H), 7.23-7.33 (m, 3H), 7.04-7.10 (m, 1H), 5.97 (d, 1H), 5.83 (s, 1H), 5.71 (q, 1H), 5.38 (d, 2H), 2.30 (s, 3H), 2.27 (s, 3H), 2.00 (d, 3H). [ES+MS] m/z 432 (MH⁺). Analytical Chiral HPLC conditions: CHIRALPAK-AD 4.6×150 mm column, method: eluent isocratic mixture ACN 0.1% isoprylamine/MeOH 0.1% isopropylamine ratio 85/15, flow: 1 mL/min. Rt: 3.39 min Chiral Separation of Racemate Example 30

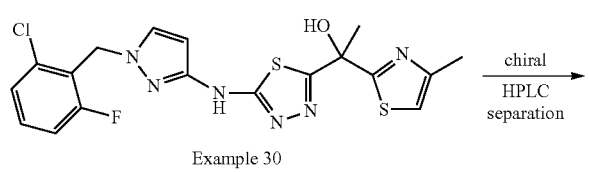

Example 30

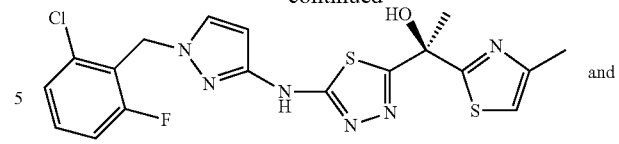

Isomer 1
Example 70

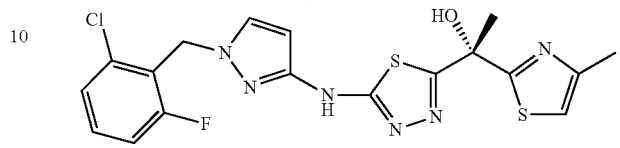

Isomer 2
Example 71

29 mg of Example 30 (racemic mixture) were separated using a CHIRALPAK-AD 20×250 mm column, F=17 mL/min, 254 nm and an isocratic mixture of ACN, 0.1% isopropylamine-(MeOH-iPrOH 60:40), 0.1% isopropylamine 90:10. Product was dissolved in 1.5 mL of methanol (HPLC grade). Separation was achieved and appropriate fractions were collected to afford both enantiomers:

Example 70

(1S)-1-[5-({1-[(2-chloro-6-fluorophenyl)methyl]-1H-pyrazol-3-yl}amino)-1,3,4-thiadiazol-2-yl]-1-(4-methyl-1,3-thiazol-2-yl)ethanol Isomer 1

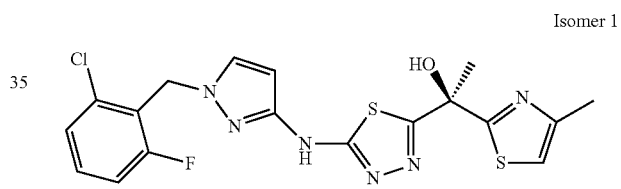

Analytical Chiral HPLC conditions: CHIRALPAK-AD 4.6×150 mm column, method: eluent isocratic mixture ACN 0.1% isoprylamine/(MeOH/Isopropanol 60:40) 0.1% isopropylamine ratio 90/10, flow: 1 mL/min. Rt: 6.02 min Example 71

(1R)-1-[5-({1-[(2-chloro-6-fluorophenyl)methyl]-1H-pyrazol-3-yl}amino)-1,3,4-thiadiazol-2-yl]-1-(4-methyl-1,3-thiazol-2-yl)ethanol Isomer 2

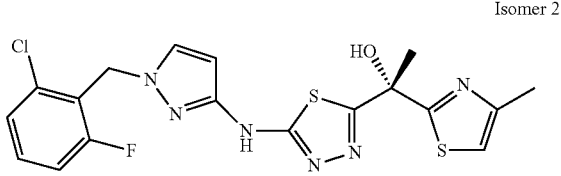 [SMILES: Cc1csc([C@@](C)(O)c2nnc(Nc3ccn(Cc4c(F)cccc4Cl)n3)s2)n1]

Analytical Chiral HPLC conditions: CHIRALPAK-AD 4.6×150 mm column, method: eluent isocratic mixture ACN 0.1% isoprylamine/(MeOH/Isopropanol 60:40) 0.1% isopropylamine ratio 90/10, flow: 1 mL/min. Rt: 15.20 min The following compounds in Table 5 (Examples 72 to 82) were prepared using the procedures described above for Examples 1 or 28, (purification details are given) and were tested in the InhA enzymatic and TB growth inhibition assays.

TABLE 5

| Ex. | Structure | Isothiocyanate intermediate | Hydrazide intermediate | Example method | Purification | Physical data |
|---|---|---|---|---|---|---|
| 72 | N-{1-[(2-chloro-6-fluorophenyl)methyl]-1H-pyrazol-3-yl}-5-[1-(methyloxy)-1-(4-methyl-1,3-thiazol-2-yl)ethyl]-1,3,4-thiadiazol-2-amine | 57 0.172 mmol | 92 0.172 mmol | Example 28 | a), b) and c) | $^1$H NMR (300 MHz, DMSO-d$_6$) δ ppm: 11.00 (br. s, 1H), 7.72 (d, 1H), 7.18-7.47 (m, 4H), 5.89 (d, 1H), 5.32 (s, 2H), 3.23 (s, 3H), 2.30 (s, 3H), 1.99 (s, 3H). [ES + MS] m/z 465 (MH$^+$) |
| 73 | N-{1-[(2,6-difluorophenyl)methyl]-1H-pyrazol-3-yl}-5-[(methyloxy)(4-methyl-1,3-thiazol-2-yl)methyl]-1,3,4-thiadiazol-2-amine | 70 1.043 mmol | 93 1.043 mmol | Example 28 | a) and d) | $^1$H NMR (300 MHz, DMSO-d$_6$) δ ppm: 10.95 (br. s, 1H), 7.72 (d, 1H), 7.37-7.48 (m, 2H), 7.05-7.14 (m, 2H), 5.93 (d, 1H), 5.91 (s, 1H), 5.26 (s, 2H), 3.40 (s, 3H), 2.32 (s, 3H). [ES + MS] m/z 435 (MH$^+$) |
| 74 | N-{1-[(2-chloro-6-fluorophenyl)methyl]-1H-pyrazol-3-yl}-5-[1-methyl-1-(4-methyl-1,3-thiazol-2-yl)ethyl]-1,3,4-thiadiazol-2-amine | 57 0.703 mmol | 94 0.703 mmol | Example 28 | a) and c) | $^1$H NMR (300 MHz, DMSO-d$_6$) δ ppm: 10.85 (br. s, 1H), 7.72 (d, 1H), 7.20-7.46 (m, 4H), 5.91 (d, 1H), 5.32 (s, 2H), 2.35 (s, 3H), 1.82 (s, 6H). [ES + MS] m/z 449 (MH$^+$) |
| 75 | 5-[1-(3,5-dimethyl-1H-pyrazol-1-yl)ethyl]-N-{1-[(4-fluorophenyl)methyl]-1H-pyrazol-3-yl}-1,3,4-thiadiazol-2-amine | 114 0.917 mmol | 78 1.101 mmol | Example 1 | c) | $^1$H NMR (300 MHz, DMSO-d$_6$) δ ppm: 10.85 (br. s, 1H), 7.73 (d, 1H), 7.25-7.32 (m, 2H), 7.10-7.18 (m, 2H), 5.96 (d, 1H), 5.84 (s, 1H), 5.77 (q, 1H), 5.18 (s, 2H), 2.24 (s, 3H), 2.09 (s, 3H), 1.79 (d, 3H). [ES + MS] m/z 398 (MH$^+$) |

TABLE 5-continued

| Ex. | Structure | Isothiocyanate intermediate | Hydrazide intermediate | Example method | Purification | Physical data |
|---|---|---|---|---|---|---|
| 76 | N-{1-[(2,6-difluorophenyl)methyl]-1H-pyrazol-3-yl}-5-[1-(3-methyl-1H-pyrazol-1-yl)ethyl]-1,3,4-thiadiazol-2-amine | 70<br>0.297 mmol | 0.297 mmol<br>ARTCHEM | Example 1 | c) | $^1$H NMR (300 MHz, DMSO-d$_6$) δ ppm: 10.85 (br. s, 1H), 7.74 (d, 1H), 7.70 (d, 1H), 7.39-7.50 (m, 1H), 7.05-7.15 (m, 2H), 6.09 (d, 1H), 5.93 (d, 1H), 5.81 (q, 1H), 5.24 (s, 2H), 2.18 (s, 3H), 1.81 (d, 3H). [ES + MS] m/z 402 (MH$^+$) |
| 77 | 5-[1-(3,5-dimethyl-1H-pyrazol-1-yl)ethyl]-N-{1-[(2,3,6-trifluorophenyl)methyl]-1H-pyrazol-3-yl}-1,3,4-thiadiazol-2-amine | 115<br>0.557 mmol | 78<br>0.613 mmol | Example 1 | b) | $^1$H NMR (300 MHz, DMSO-d$_6$) δ ppm: 10.87 (br. s, 1H), 7.75 (d, 1H), 7.45-7.58 (m, 1H), 7.10-7.19 (m, 1H), 5.93 (d, 1H), 5.84 (s, 1H), 5.75 (q, 1H), 5.29 (s, 2H), 2.24 (s, 3H), 2.10 (s, 3H), 1.78 (d, 3H). [ES + MS] m/z 434 (MH$^+$) |
| 79 | 1-[5-({1-[(3-chloro-2-fluorophenyl)methyl]-1H-pyrazol-3-yl}amino)-1,3,4-thiadiazol-2-yl]-1-(4-methyl-1,3-thiazol-2-yl)ethanol | 62<br>0.730 mmol | 82<br>0.730 mmol | Example 28 | e) and b) | $^1$H NMR (300 MHz, DMSO-d$_6$) δ ppm: 10.88 (br. s, 1H), 7.76 (d, 1H), 7.49-7.56 (m, 1H), 7.10-7.29 (m, 4H), 5.98 (d, 1H), 5.32 (s, 2H), 2.29 (s, 3H), 1.97 (s, 3H). [ES + MS] m/z 451 (MH$^+$) |
| 80 | 1-[5-({1-[(2,3-difluorophenyl)methyl]-1H-pyrazol-3-yl}amino)-1,3,4-thiadiazol-2-yl]-1-(4-methyl-1,3-thiazol-2-yl)ethanol | 65<br>0.919 mmol | 82<br>0.919 mmol | Example 28 | e) and b) | $^1$H NMR (300 MHz, DMSO-d$_6$) δ ppm: 10.88 (br. s, 1H), 7.76 (d, 1H), 6.96-7.43 (m, 5H), 5.98 (d, 1H), 5.32 (s, 2H), 2.29 (s, 3H), 1.97 (s, 3H). [ES + MS] m/z 435 (MH$^+$) |
| 81 | N-{1-[(2,6-difluoro-3-methylphenyl)methyl]-1H-pyrazol-3-yl}-5-[1-(3,5-dimethyl-1H-pyrazol-1-yl)ethyl]-1,3,4-thiadiazol-2-amine | 116<br>1.086 mmol | 78<br>1.086 mmol | Example 1 | b) | $^1$H NMR (300 MHz, DMSO-d$_6$) δ ppm: 10.84 (br. s, 1H), 7.70 (d, 1H), 7.25-7.35 (m, 1H), 6.95-7.03 (m, 1H), 5.92 (d, 1H), 5.84 (s, 1H), 5.75 (q, 1H), 5.23 (s, 2H), 2.24 (s, 3H), 2.21 (s, 3H), 2.10 (s, 3H), 1.78 (d, 3H). [ES + MS] m/z 430 (MH$^+$) |

TABLE 5-continued

| Ex. | Structure | Isothiocyanate intermediate | Hydrazide intermediate | Example method | Purification | Physical data |
|---|---|---|---|---|---|---|
| 82 | 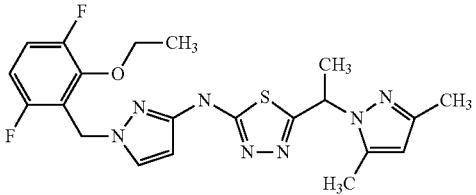<br>5-[1-(3,5-dimethyl-1H-pyrazol-1-yl)ethyl]-N-(1-{[2-(ethyloxy)-3,6-difluorophenyl]methyl}-1H-pyrazol-3-yl)-1,3,4-thiadiazol-2-amine | 117<br>0.271 mmol | 78<br>0.271 mmol | Example 20 | b) and f) | $^1$H NMR (300 MHz, DMSO-d$_6$) δ ppm: 10.85 (br. s, 1H), 7.68 (d, 1H), 7.26-7.36 (m, 1H), 6.92-7.01 (m, 1H), 5.90 (d, 1H), 5.83 (s, 1H), 5.74 (q, 1H), 5.21 (s, 2H), 4.11 (q, 2H), 2.23 (s, 3H), 2.09 (s, 3H), 1.78 (d, 3H), 1.31 (t, 3H). [ES + MS] m/z 460 (MH$^+$) | a) Aqueous mixture was extracted with EtOAc. Organic extract was washed with brine, dried over sodium sulphate and concentrated.
b) Crude was purified by chromatography on silica gel using a Hexane/EtOAc gradient.
c) Crude was purified by chromatography on silica gel using a DCM/MeOH gradient.
d) Residue was triturated with ethanol, filtered and dried under vacuum.
e) Resulting precipitate was filtered, washed with water several times, and dried under vacuum.
f) Preparative HPLC using XTERRA Chromatography Column (19 mm × 150 mm), Method (40_80) ACN (0.1% TFA)/H$_2$O (0.1% TFA).

Example 78

1-[5-({1-[(2,6-difluorophenyl)methyl]-1H-pyrazol-3-yl}amino)-1,3,4-thiadiazol-2-yl]-1-(4-methyl-1,3-thiazol-2-yl)ethanol

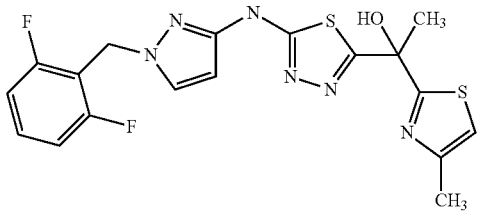 [SMILES: Cc1csc(C(C)(O)c2nnc(Nc3ccn(Cc4c(F)cccc4F)n3)s2)n1]

A solution of Intermediate 82 (168 mg, 0.835 mmol) and Intermediate 70 (210 mg, 0.835 mmol) in Ethanol (10 mL) was heated under reflux for 1 h. The hydrazinecarbothioamide intermediate was obtained [ES+MS] m/z 453 (MH$^+$). Reaction mixture was concentrated. Residue was placed in an ice-bath and treated carefully and dropwise with sulfuric acid (3 mL, 0.835 mmol). Reaction mixture was allowed to reach rt over 4 hours. Reaction mixture was placed in an ice-bath and treated carefully and cautiously with 37% aq. NH$_3$ (15 mL) until pH was basic. Then the mixture was diluted with EtOAc (100 mL) and water. Phases were separated and the organic was washed with brine, dried over sodium sulfate and concentrated to give 360 mg of crude. Purified by chromatography on silica gel using a linear gradient, 0->70% EtOAc-Hex to yield the title compound (130 mg, 35.8% yield). $^1$H NMR (300 MHz, DMSO-d$_6$) δ ppm: 10.83 (br.s, 1H), 7.69 (d, 1H), 7.38-7.49 (m, 1H), 7.20-7.26 (m, 2H), 7.05-7.15 (m, 2H), 5.93 (d, 1H), 5.25 (s, 2H), 2.29 (s, 3H), 1.97 (s, 3H). [ES+MS] m/z 435 (MN$^+$)

The following compounds in Table 6 (Examples 83 to 86) were prepared following the procedures described above for Examples 1 or 28, (purification details are given) and were tested in the InhA enzymatic and TB growth inhibition assays.

TABLE 6

| Ex. | Structure | Isothiocyanate intermediate | Hydrazide intermediate | Example method | Purification | Physical data |
|---|---|---|---|---|---|---|
| 83 | 1-[5-({1-[(2-fluoro-3-methylphenyl)methyl]-1H-pyrazol-3-yl}amino)-1,3,4-thiadiazol-2-yl]-1-(4-methyl-1,3-thiazol-2-yl)ethanol<br>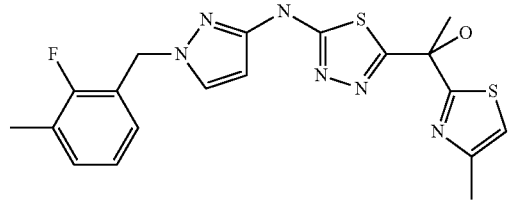 | 69<br>0.189 mmol | 82<br>0.189 mmol | Example 28 | No further purification | $^1$H NMR (300 MHz, DMSO-d$_6$) δ ppm: 7.70 (d, 1H), 7.18-7.29 (m, 3H), 6.95-7.06 (m, 2H), 5.94 (d, 1H), 5.24 (s, 2H), 2.29 (s, 3H), 2.23 (d, 3H), 1.97 (s, 3H). [ES+MS] m/z 431 (MH$^+$) |

TABLE 6-continued

| Ex. | Structure | Isothiocyanate intermediate | Hydrazide intermediate | Example method | Purification | Physical data |
|---|---|---|---|---|---|---|
| 84 | 1-[5-({1-[(2,6-difluoro-3-methylphenyl)methyl]-1H-pyrazol-3-yl}amino)-1,3,4-thiadiazol-2-yl]-1-(4-methyl-1,3-thiazol-2-yl)ethanol 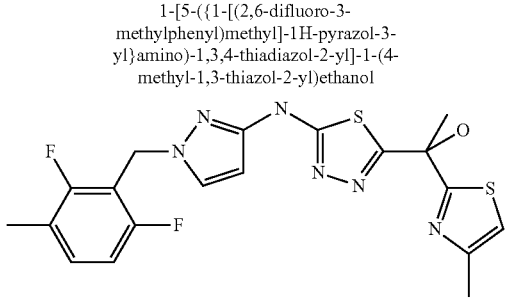 [SMILES: Cc1csc(C(C)(O)c2nnc(Nc3ccn(Cc4c(F)ccc(C)c4F)n3)s2)n1] | 116 0.199 mmol | 82 <br> 0.199 mmol | Example 28 | a) and b) | ¹H NMR (300 MHz, DMSO-d₆) δ ppm: 10.82 (br.s, 1H), 7.68 (d, 1H), 7.19-7.34 (m, 3H), 6.95-7.03 (m, 1H), 5.92 (d, 1H), 5.23 (s, 2H), 2.29 (s, 3H), 2.20 (s, 3H), 1.97 (s, 3H). [ES+ MS] m/z 449 (MH⁺) |
| 85 | N-{1-[(2,6-difluoro-3-methylphenyl)methyl]-1H-pyrazol-3-yl}-5-[1-(4-methyl-1,3-thiazol-2-yl)ethyl]-1,3,4-thiadiazol-2-amine 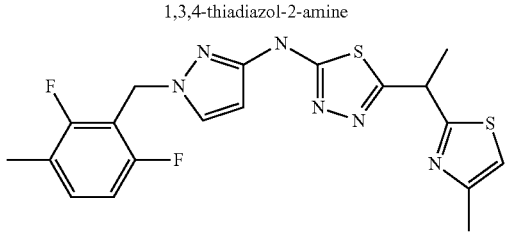 | 116 0.520 mmol | 81 <br> 0.520 mmol | Example 1 | c) | ¹H NMR (300 MHz, DMSO-d₆) δ ppm: 7.70 (d, 1H), 7.19-7.34 (m, 2H), 6.95-7.04 (m, 1H), 5.94 (d, 1H), 5.24 (s, 2H), 4.87 (q, 1H), 2.35 (s, 3H), 2.18 (s, 3H), 1.72 (d, 3H). [ES+ MS] m/z 433 (MH⁺) |
| 86 | 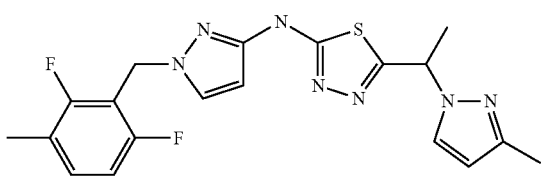 <br> N-{1-[(2,6-difluoro-3-methylphenyl)methyl]-1H-pyrazol-3-yl}-5-[1-(3-methyl-1H-pyrazol-1-yl)ethyl]-1,3,4-thiadiazol-2-amine | 116 0.520 mmol | 0.520 mmol ARTCHEM | Example 1 | No further purification | ¹H NMR (300 MHz, DMSO-d₆) δ ppm: 7.73 (d, 1H), 7.69 (d, 1H), 7.25-7.35 (m, 1H), 6.95-7.04 (m, 1H), 6.07 (d, 1H), 5.93 (d, 1H), 5.82 (q, 1H), 5.23 (s, 2H), 2.20 (s, 3H), 2.17 (s, 3H), 1.81 (d, 3H). [ES+ MS] m/z 416 (MH⁺) | a) Aqueous mixture was extracted with EtOAc. Organic extract was washed with brine, dried over sodium sulphate and concentrated.

bc) Crude was purified by chromatography on silica gel using a DCM/MeOH gradient.

c) Preparative HPLC using XBRIDGE Chromatography Column (19 mm × 150 mm), Method (40_100) ACN/H₂O (0.1% NH₄CO₃ 10 mM).

Example 87

N-{1-[(3-amino-2,6-difluorophenyl)methyl]-1H-pyrazol-3-yl}-5-[1-(3,5-dimethyl-1H-pyrazol-1-yl)ethyl]-1,3,4-thiadiazol-2-amine

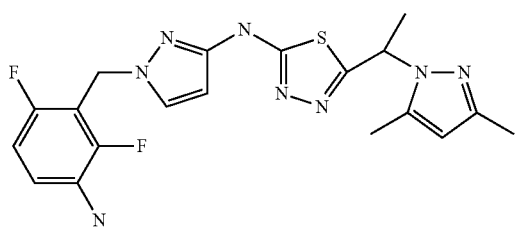 [SMILES: Cc1cc(C)n(C(C)c2nnc(Nc3ccn(Cc4c(F)ccc(N)c4F)n3)s2)n1]

A solution of Intermediate 120 (N-{2,4-difluoro-3-[(3-isothiocyanato-1H-pyrazol-1-yl)methyl]phenyl}acetamide, 80 mg, 0.259 mmol) and Intermediate 78 (2-(3,5-dimethyl-1H-pyrazol-1-yl)propanohydrazide, 48 mg, 0.259 mmol) in 5 ml of DCM (anh) was stirred at room temperature overnight. Reaction mixture was concentrated under vacuum to give N-[3-({3-[({2-[2-(3,5-dimethyl-1H-pyrazol-1-yl)propanoyl]hydrazino}carbonothioyl)amino]-1H-pyrazol-1-yl}methyl)-2,4-difluorophenyl]acetamide (145 mg, 0.296 mmol) as an orange solid [ES+MS] m/z 491 (MH+)]. This solid, without further purification, was dissolved in H$_2$SO$_4$ (conc) 4 mL and stirred at room temperature during 45 min. Resulting mixture was neutralized with 32% NH$_3$ (aq) under ice-bath until basic pH. Then, reaction mixture was partitioned with AcOEt (×3) (15 mL). Organic layers were washed with distilled water (10 mL), and dried over MgSO$_4$(anh), filtered and concentrated to give a solid that was purified by HPLC preparative XBRIDGE__10 using ACN: NH$_4$CO$_3$(aq, 0.1%) (30__100). Two different compounds were isolated as solids, they were characterized as:

Intermediate 122

N-(3-{[3-({5-[1-(3,5-dimethyl-1H-pyrazol-1-yl)ethyl]-1,3,4-thiadiazol-2-yl}amino)-1H-pyrazol-1-yl]methyl}-2,4-difluorophenyl)acetamide

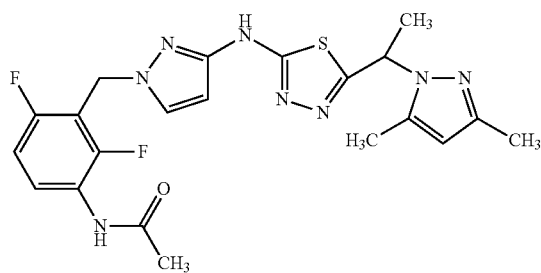 [SMILES: CC(=O)Nc1ccc(F)c(Cn2ccc(Nc3nnc(C(C)n4nc(C)cc4C)s3)n2)c1F]

(20 mgr, 0.042 mmol, yield 21%) $^1$H NMR (300 MHz, DMSO-d$_6$) δ ppm: 10.83 (br.s, 1H), 9.72 (br.s, 1H), 7.68-7.86 (m, 2H), 7.01-7.11 (m, 1H), 5.95 (s, 1H), 5.84 (s, 1H), 5.75 (q, 1H), 5.26 (s, 2H), 2.24 (s, 3H), 2.10 (s, 3H), 2.05 (s, 3H), 1.79 (d, 3H). [ES+MS] m/z 473 (MH+); and Title compound Example 87 N-{1-[(3-amino-2,6-difluorophenyl)methyl]-1H-pyrazol-3-yl}-5-[1-(3,5-dimethyl-1H-pyrazol-1-yl)ethyl]-1,3,4-thiadiazol-2-amine (13 mgr, 0.030 mmol, yield 15%) $^1$H NMR (300 MHz, DMSO-d$_6$) δ ppm: 10.82 (br.s, 1H), 7.63 (s, 1H), 6.68-6.83 (m, 2H), 5.95 (s, 1H), 5.84 (s, 1H), 5.75 (q, 1H), 5.18 (s, 2H), 5.02 (s, 2H), 2.24 (s, 3H), 2.11 (s, 3H), 1.79 (d, 3H). [ES+MS] m/z 431 (MH+)

Example 88

1-[5-({1-[(3-amino-2-fluorophenyl)methyl]-1H-pyrazol-3-yl}amino)-1,3,4-thiadiazol-2-yl]-1-(4-methyl-1,3-thiazol-2-yl)ethanol

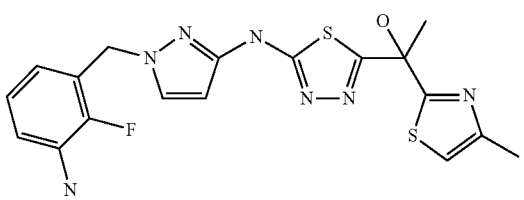 [SMILES: Cc1csc(C(C)(O)c2nnc(Nc3ccn(Cc4cccc(N)c4F)n3)s2)n1]

Intermediate 121 ethyl (2-fluoro-3-{[3-({5-[-1-hydroxy-1-(4-methyl-1,3-thiazol-2-ylethyl]-1,3,4-thiadiazol-2-yl}amino)-1H-pyrazol-1-yl]methyl}phenyl)carbamate (108 mg, 0.214 mmol) was dissolved in 4 ml of THF (anh) under nitrogen atmosphere. Then, N,N,N-tributyl-1-butanaminium fluoride (ALDRICH, 214 µL, 0.214 mmol) was added and the reaction mixture was heated under reflux. After 2 h 45 min more N,N,N-tributyl-1-butanaminium fluoride (ALDRICH, 214 µL, 0.214 mmol) was added and reaction mixture was stirred at room temperature overnight. Reaction was diluted adding 20 ml of THF, and more N,N,N-tributyl-1-butanaminium fluoride (ALDRICH, 214 µL, 0.214 mmol) was added and temperature was fixed at 50° C. for 1 h 30 min, stirring. Then, solvents were eliminated under vacuum and crude of reaction was purified by chromatography on silica, using a DCM/MeOH (0-30-50%) gradient. A second purification was carried out using a SunFire chromatography column with a gradient of (25__100) ACN(0.1% Formic Acid)/Water(0.1% Formic Acid) as eluent to yield the title compound as a white solid (15 mg, 15%). $^1$H NMR (300 MHz, DMSO-d$_6$) δ ppm: 10.84 (br.s. 1H), 7.65 (d, 1H), 7.28 (s, 1H), 7.20 (s, 1H), 6.62-6.82 (m, 2H), 6.25-6.33 (m, 1H), 5.95 (d, 1H), 5.10-5.20 (m, 4H), 2.29 (s, 3H), 1.79 (s, 3H). [ES+MS] m/z 432 (MH+).

Chiral Separation of Racemate Example 78

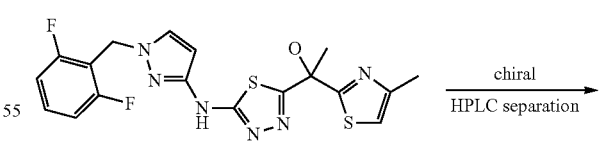

Example 78

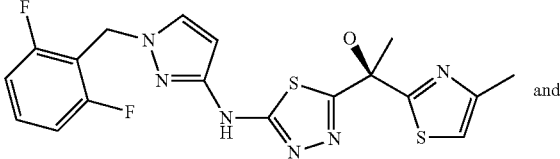

Isomer 1
Example 91

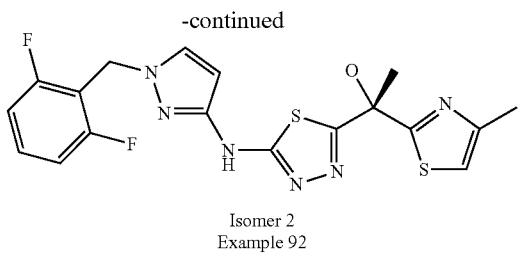

Isomer 2
Example 92

78 mg of Example 78 (racemic mixture) were separated using a CHIRALPAK-AD 20×250 mm column, F=17 mL/min, 254 nm and an isocratic mixture of ACN, 0.1% isopropylamine-(MeOH-iPrOH 60:40), 0.1% isopropylamine 90:10. Product was dissolved in 3.5 mL of MeOH/ACN (1 mL MeOH and 2.5 mL ACN, HPLC grade). Two injections were needed. Separation was achieved and appropriate fractions were collected to afford both enantiomers:

Example 89

(1S)-1-[5-({1-[(2,6-difluorophenyl)methyl]-1H-pyrazol-3-yl}amino)-1,3,4-thiadiazol-2-yl]-1-(4-methyl-1,3-thiazol-2-yl)ethanol Isomer 1

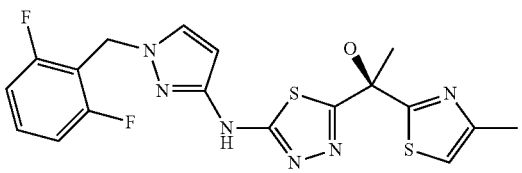

Isomer 1, first elution in HPLC: 28 mg, light orange solid. $^1$H NMR (300 MHz, DMSO-$d_6$) δ ppm: 10.82 (br.s, 1H), 7.69 (s, 1H), 7.39-7.49 (m, 1H), 7.24 (s, 1H), 7.22 (s, 1H), 7.06-7.14 (m, 2H), 5.93 (s, 1H), 5.25 (s, 2H), 2.29 (s, 3H), 1.97 (s, 3H). [ES+MS] m/z 435 (MH$^+$).

Analytical Chiral HPLC conditions: CHIRALPAK-AD-H 4.6×150 mm column, method: eluent isocratic mixture ACN, 0.1% isopropylamine-(MeOH-iPrOH 60:40), 0.1% isopropylamine ratio 90:10, flow: 1 mL/min. Rt: 3.89 min. $\alpha_D$=+101.55°. The absolute configurations were determined by ab initio vibrational circular dichroism (VCD).

Example 90

(1R)-1-[5-({1-[(2,6-difluorophenyl)methyl]-1H-pyrazol-3-yl}amino)-1,3,4-thiadiazol-2-yl]-1-(4-methyl-1,3-thiazol-2-yl)ethanol Isomer 2

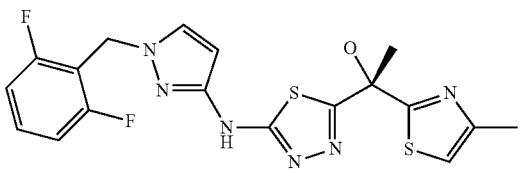

Isomer 2, second elution in HPLC: 41 mg, pale yellow solid. $^1$H NMR (300 MHz, DMSO-$d_6$) δ ppm: 10.83 (br.s, 1H), 7.69 (s, 1H), 7.39-7.49 (m, 1H), 7.24 (s, 1H), 7.22 (s, 1H), 7.06-7.14 (m, 2H), 5.93 (s, 1H), 5.25 (s, 2H), 2.29 (s, 3H), 1.97 (s, 3H). [ES+MS] m/z 435 (MH+).

Analytical Chiral HPLC conditions: CHIRALPAK-AD-H 4.6×150 mm column, method: eluent isocratic mixture ACN, 0.1% isopropylamine-(MeOH-iPrOH 60:40), 0.1% isopropylamine ratio 90:10, flow: 1 mL/min. Rt: 5.93 min. $\alpha D$=−96.08°. The absolute configurations were determined by ab initio vibrational circular dichroism (VCD).;

Biological Activity

*Mycobacterium tuberculosis* H37Rv Inhibition Assay (Whole Cell Assay)

The measurement of the minimum inhibitory concentration (MIC) for each tested compound was performed in 96 wells flat-bottom, polystyrene microtiter plates. Ten two-fold drug dilutions in neat DMSO starting at 400 μM were performed. Five μl of these drug solutions were added to 95 μl of Middlebrook 7H9 medium. (Lines A-H, rows 1-10 of the plate layout). Isoniazid was used as a positive control, 8 two-fold dilution of Isoniazid starting at 160 μg/ml was prepared and 5 μl of this control curve was added to 95 μl of Middlebrook 7H9 medium (Difco catalogue ref. 271310). (Row 11, lines A-H). 5 μl of neat DMSO were added to row 12 (growth and Blank controls).

The inoculum was standardised to approximately 1×10$^7$ cfu/ml and diluted 1 in 100 in Middlebrook 7H9 broth (Middlebrook ADC enrichment, a dehydrated culture media which supports growth of mycobacterial species available from Becton Dickinson Catalogue Ref. 211887), to produce the final inoculum of H37Rv strain (ATCC25618). One hundred μl of this inoculum was added to the entire plate but G-12 and H-12 wells (Blank controls). All plates were placed in a sealed box to prevent drying out of the peripheral wells and they were incubated at 37° C. without shaking for six days. A resazurin solution was prepared by dissolving one tablet of resazurin (Resazurin Tablets for Milk Testing; Ref 330884Y VWR International Ltd) in 30 ml sterile PBS (phosphate buffered saline). 25 μl of this solution was added to each well. Fluorescence was measured (Spectramax M5 Molecular Devices, Excitation 530 nm, Emission 590 nm) after 48 hours to determine the MIC value.

Results of the *Mycobacterium tuberculosis* H37Rv Inhibition Assay (Whole Cell Assay)

Unless otherwise stated hereinbelow, all Examples were tested in the whole cell assay. Intermediates 121 and 122 were also tested in this assay.

Examples 7, 10, 12, 13, 23, 24, 28, 30, 38, 70, 76-81, 83, 84, 86 and 89, described hereinabove were found to have an MIC value of 1 μM or less. For example, Example 89 was found to have an MIC value of 0.2 μM.

Examples 3, 6, 14-16, 19, 20, 22, 25, 29, 33, 39, 40, 42, 44, 54, 66, 67, 69, 71, 72, 74, 85 and 87 and Intermediate 121 described hereinabove were found to have an MIC value of 4 μM or less, but above 1 μM.

Examples 1, 4, 5, 21, 27, 32, 34, 36, 37, 41, 43 and 82 described hereinabove were found to have an MIC value of 10 μM or less, but above 4 μM.

Examples 2, 8, 9, 11, 17, 18, 26, 31, 35, 45-53, 55-64, 68, 73, 75 and 90 and Intermediate 122 described hereinabove were found to have an MIC value of greater than 10 μM.

Example 65 was not tested in the whole cell assay.

In one aspect, compounds of the invention have an MIC value of 4 μM or less in the *Mycobacterium tuberculosis* H37Rv Inhibition Assay (Whole Cell Assay).

*Mycobacterium tuberculosis* InhA Inhibition Assay (Enzyme Assay)

InhA is able to reduce 2-trans enoyl-CoA esters with concomitant oxidation of NADH to NAD$^+$. The assay format is based on the kinetic detection of NADH consumption.

Assay for InhA inhibition is carried out with mycobacterium recombinant protein expressed and purified form *E. coli*. Standard assay conditions for the determination of kinetic constants and inhibitors activity use 5 nM of InhA, 50 μM of Dodecenoyl-CoA synthesized and purified as described by Quernard et al (DDCoA) and 50 μM of NADH as substrates, and it is carried out in 30 mM PIPES buffer pH 6.8, containing 0.05% of BSA. Solutions of compounds to be tested are prepared in 100% DMSO; eight one-third dilutions starting at 25 (or 1 μM for the most potent compounds) were made for doses-response curves. Triclosan is used as positive control in every experiment. One μl of compounds is added to the wells containing 25 μl of the DDCoA+NADH mix, the reaction is started by adding 50 μl of the enzyme solution. Fluorescence from NADH is followed at room temperature during 20 minutes in a fluorescent plate reader (excitation at 340 nM; emission at 480 nM). IC$_{50}$ values are determined using initial velocities of NADH consumption.

Quernard A, Sacchettini J C, Dessen A, et al. Enzymatic characterization of the target for isoniazid in *Mycobacterium tuberculosis*. Biochemistry 1995; 34:8235-41.

Results of the *Mycobacterium tuberculosis* InhA Inhibition Assay (Enzyme Assay)

Unless otherwise stated hereinbelow, all Examples were tested in the enzyme assay. Intermediates 121 and 122 were also tested in this assay.

Examples 1-16, 19-33, 36-43, 46, 47, 49-51, 53-57, 66-72, 74 and 76-89 and Intermediate 121 described hereinabove were found to have an IC$_{50}$ value of less than 0.05 μg/ml. For example, Example 89 was found to have an IC$_{50}$ value of 0.002 μg/ml.

Examples 17, 18, 34, 44, 45, 48, 52, 73, 75 and 90 and Intermediate 122 described hereinabove were found to have an IC$_{50}$ value of less than 0.10 μg/ml but more than 0.05 μg/ml.

Examples 35 and 58-64 described hereinabove were found to have an IC$_{50}$ value of less than 0.50 μg/ml but more than 0.10 μg/ml.

Example 65 described hereinabove was found to have an IC$_{50}$ value of greater than 0.50 μg/ml.

In one aspect, compounds of the invention have an IC$_{50}$ value of less than 0.05 μg/ml in the *Mycobacterium tuberculosis* InhA Inhibition Assay (Enzyme Assay).

All publications, including but not limited to patents and patent applications cited in this specification are herein incorporated by reference as if each individual publication were specifically and individually indicated to be incorporated by reference as though fully set forth.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

The invention claimed is:

1. A method of treating tuberculosis in a mammal, which method comprises the administration to a mammal in need of such treatment an effective amount of a compound of Formula (I), or a pharmaceutically acceptable salt thereof, (I)

wherein:
either X is N and Y is CR$^5$; or X is C and Y is S;
Z is selected from N and CH;
R$^1$ is selected from H and Me,
R$^2$ is selected from H, OH, OMe and Me;
each R$^3$ is independently selected from C$_{1-3}$alkyl, F, Cl, Br, CF$_3$ and NH$_2$;
R$^4$ is selected from Me, CF$_3$, NO$_2$ and CHF$_2$;
R$^5$ is selected from H, Me and CHF$_2$;
R$^6$ is selected from H and Me; and
p is 0-3.

2. The method of claim 1 wherein in the compound R$^1$ is Me,

3. The method of treatment according to claim 1 wherein the compound is selected from:

N-{1-[(2-chloro-6-fluorophenyl)methyl]-1H-pyrazol-3-yl}-5-[1-(3-methyl-1H-pyrazol-1-yl)ethyl]-1,3,4-thiadiazol-2-amine N-{1-[(2-chloro-6-fluorophenyl)methyl]-1H-pyrazol-3-yl}-5-[(3-methyl-1H-pyrazol-1-yl)methyl]-1,3,4-thiadiazol-2-amine N-{1-[(2-chlorophenyl)methyl]-1H-pyrazol-3-yl}-5-[1-(5-methyl-3-nitro-1H-pyrazol-1-yl)ethyl]-1,3,4-thiadiazol-2-amine N-{1-[(2-chlorophenyl)methyl]-1H-pyrazol-3-yl}-5-{1-[3-(difluoromethyl)-5-methyl-1H-pyrazol-1-yl]ethyl}-1,3,4-thiaoliazol-2-amine N-{1-[(2-chlorophenyl)methyl]-1H-pyrazol-3-yl}-5-[1-(3-methyl-1H-pyrazol-1-yl)ethyl]-1,3,4-thiadiazol-2-amine 5-{1-[3-(difluoromethyl)-5-methyl-1H-pyrazol-1-yl]ethyl}-N-[1-(phenylmethyl)-1H-pyrazol-3-yl]-1,3,4-thiadiazol-2-amine 5-[1-(3-methyl-1H-pyrazol-1-yl)ethyl]-N-[1-(phenylmethyl)-1H-pyrazol-3-yl]-1,3,4-thiadiazol-2-amine 5-{[3-(difluoromethyl)-5-methyl-1H-pyrazol-1-yl]methyl}-N-[1-(phenylmethyl)-1H-pyrazol-3-yl]-1,3,4-thiadiazol-2-amine N-{1-[(2-chlorophenyl)methyl]-1H-pyrazol-3-yl}-5-{[3-(difluoromethyl)-5-methyl-1H-pyrazol-1-yl]methyl}-1,3,4-thiadiazol-2-amine N-{1-[(2,6-dichlorophenyl)methyl]-1H-pyrazol-3-yl}-5-[(3-nitro-1H-pyrazol-1-yl)methyl]-1,3,4-thiadiazol-2-amine N-{1-[(2-chlorophenyl)methyl]-1H-pyrazol-3-yl}-5-{[5-methyl-3-(trifluoromethyl)-1H-pyrazol-1-yl]methyl}-1,3,4-thiadiazol-2-amine N-{1-[(2-chlorophenyl)methyl]-1H-pyrazol-3-yl}-5(3-nitro-1H-pyrazol-1-yl)methyl-1,3,4-thiadiazol-2-amine N-{1-[(2-chloro-6-fluorophenyl)methyl]-1H-pyrazol-3-yl}-5-[(5-methyl-3-nitro-1H-pyrazol-1-yl)methyl]-1,3,4-thiadiazol-2-amine N-{1-[(2-chloro-6-fluorophenyl)methyl]-1H-pyrazol-3-yl}-5-[(3,5-dimethyl-1H-pyrazol-1-yl)methyl]-1,3,4-thiadiazol-2-amine N-{1-[(2-chloro-6-fluorophenyl)methyl]-1H-pyrazol-3-yl}-5-[(3-nitro-1H-pyrazol-1-yl)methyl]-1,3,4-thiadiazol-2-amine N-{1-[(2,6-dichlorophenyl)methyl]-1H-pyrazol-3-yl}-5-[(3,5-dimethyl-1H-pyrazol-1-yl)methyl]-1,3,4-thiadiazol-2-amine N-{1-[(2,6-dichlorophenyl)methyl]-1H-pyrazol-3-yl}-5-[1-(3-methyl-1H-pyrazol-1-yl)ethyl]-1,3,4-thiadiazol-2-amine N-{1-[(2-chloro-6-fluorophenyl)methyl]-1H-pyrazol-3-yl}-5-{[3-(difluoromethyl)-5-methyl-1H-pyrazol-1-yl]methyl}-1,3,4-thiadiazol-2-amine N-{1-[(2-chlorophenyl)methyl]-1H-pyrazol-3-yl}-5-[(3,5-dimethyl-1H-pyrazol-1-yl)methyl]-1,3,4-thiadiazol-2-amine N-{1-[(2,6-dichlorophenyl)methyl]-1H-pyrazol-3-yl}-5-[(3-methyl-1H-pyrazol-1-yl)methyl]-1,3,4-thiadiazol-2-amine N-{1-[(2-chlorophenyl)methyl]-1H-pyrazol-3-yl}-5-[(5-methyl-3-nitro-1H-pyrazol-1-yl)methyl]-1,3,4-thiadiazol-2-amine N-{1-[(2-chlorophenyl)methyl]-1H-pyrazol-3-yl}-5-{[3-(trifluoromethyl)-1H-pyrazol-1-yl]methyl}-1,3,4-thiadiazol-2-amine 5-[(3-methyl-1H-pyrazol-1-yl)methyl]-N-[1-(phenylmethyl)-1H-pyrazol-3-yl]-1,3,4-thiadiazol-2-amine N[1-(phenylmethyl)-1H-pyrazol-3-yl]-5-{[3-(trifluoromethyl)-1H-pyrazol-1-yl]methyl}-1,3,4-thiadiazol-2-amine 5-[(5-methyl-3-nitro-1H-pyrazol-1-yl)methyl]-N-[1-(phenylmethyl)-1H-pyrazol-3-yl]-1,3,4-thiadiazol-2-amine N-{1-[(2-chloro-6-fluorophenyl)methyl]-1H-pyrazol-3-yl}-5-{[3-(trifluoromethyl)-1H-pyrazol-1-yl]methyl}-1,3,4-thiadiazol-2-amine 5-[(3,5-dimethyl-1H-pyrazol-1-yl)methyl]-N-[1-(phenylmethyl)-1H-pyrazol-3-yl]-1-1,3,4-thiadiazol-2-amine and N-{1-[(2,6-dichlorophenyl)methyl]-1H-pyrazol-3-yl}-5-[1-(5-methyl-3-nitro-1H-pyrazol-1-yl)methyl]-1,3,4-thiadiazol-2-amine, or a pharmaceutically acceptable salt thereof for use in therapy.

4. The method of claim 1 wherein the mammal is a human.

5. A compound of Formula (I), or a pharmaceutically acceptable salt thereof:

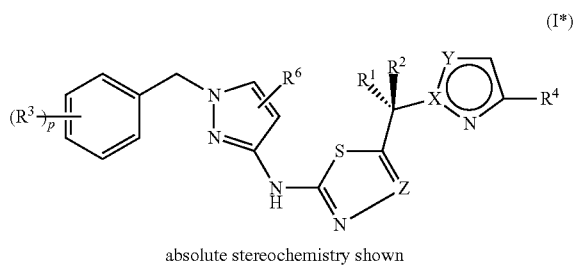

(I*)

absolute stereochemistry shown wherein:
either X is N and Y is CR$^5$; or X is C and Y is S;
Z is selected from N and CH;
R$^1$ is Me, R$^2$ is selected from H, OH, and OMe;
each R$^3$ is independently selected from C$_{1-3}$alkyl, F, Cl, Br, CF$_3$ and NH$_2$;
R$^4$ is Me;
R$^5$ is selected from H, Me and CHF$_2$;
R$^6$ is selected from H and Me; and
p is 0-3.

6. The compound of claim 5 selected from:
N-{1-[(2-chloro--6-fluorophenyl)methyl]-1H-pyrazol-3-yl}-5-[(1S)-1-(3-methyl-1H-pyrazol-1-yl)ethyl]-1,3,4-thiadiazol-2-amine N-{1-[(2-chloro-6-fluorophenyl)methyl]-1H-pyrazol-3-yl}-5-[(1S)-1-(3,5-dimethyl-1H-pyrazol-1-yl)ethyl]1,3,4-thiadiazol-2-amine (1S)-1-[5-({1-[(2-chloro-6-fluorophenyl)methyl]-1H-pyrazol-3-yl}amino)-1,3,4-thiadiazol-2-yl]-1-(4-methyl-1,3-thiazol-2-yl)ethanol (1S)-1-[5-({1-[(2,6-difluorophenyl)methyl]-1H-pyrazol-3-yl}amino)- 1,3,4-thiadiazol-2-yl]-1-(4-methyl-1,3-thiazol-2-yl)ethanol, or a pharmaceutically acceptable salt thereof.

7. The compound of claim 6 which is (1S)-1-[5-({1-[(2,6-difluorophenyl)methyl]-1H-pyrazol-3-yl}amino)-1,3,4-thiadiazol-2-yl]-1-(4-methyl-1,3-thiazol-2-yl)ethanol, or a pharmaceutically acceptable salt thereof.

8. The compound of claim 6 which is (1S)-1-[5-({1-[(2,6-difluorophenyl)methyl]-1H-pyrazol-3-yl}amino)-1,3,4-thiadiazol-2-yl]-(4-methyl-1,3-thiazol-2-yl)ethanol.

9. A method of treatment of tuberculosis in mammals, which method comprises the administration to a mammal in need of such treatment an effective amount of a compound or a pharmaceutically acceptable salt thereof as defined in claim 5.

10. The method as claimed in claim 9 wherein the mammal is a human.

11. A pharmaceutical composition comprising a compound or a pharmaceutically acceptable salt thereof as defined in claim 5 and one or more pharmaceutically acceptable carriers, excipients or diluents.

12. A combination comprising a compound of Formula (1*) or pharmaceutically acceptable salt thereof as defined in claim 5 together with one or more additional therapeutic agents.

13. The combination as claimed in claim 12 wherein the one or more additional therapeutic agent is an anti-tuberculosis agent.

14. A compound of Formula (I), or a pharmaceutically acceptable salt thereof, (I)

wherein:
X is C and Y is S;
Z is selected from N and CH;
R$^1$ is selected from H and Me,
R$^2$ is selected from H, OH, OMe and Me;
each R$^3$ is independently selected from C$_{1-3}$alkyl, F, Cl, Br, CF$_3$ and NH$_2$;

$R^4$ is selected from Me, $CF_3$, $NO_2$ and $CHF_2$;
$R^6$ is selected from H and Me; and
p is 0-3.

15. The compound or a pharmaceutically acceptable salt thereof as claimed in claim 14 wherein $R^1$ is Me.

16. The compound or a pharmaceutically acceptable salt thereof as claimed in claim 15 wherein $R^2$ is selected from H, OH and OMe and which has the absolute stereochemistry shown in Formula (I*):

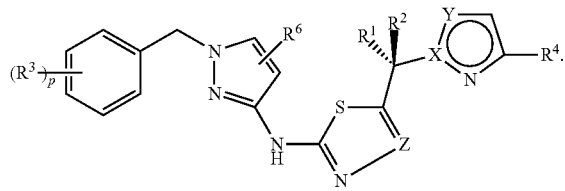

17. A method of treatment of tuberculosis in mammals, which method comprises the administration to a mammal in need of such treatment an effective amount of a compound, or a pharmaceutically acceptable salt thereof, as defined in claim 16.

18. The method as claimed in claim 17, wherein the mammal is a human.

19. A pharmaceutical composition comprising a compound or a pharmaceutically acceptable salt thereof as defined in claim 16 and one or more pharmaceutically acceptable carriers, excipients or diluents.

20. A combination comprising a compound or pharmaceutically acceptable salt thereof as claimed in claim 16 together with one or more additional therapeutic agents.

21. A combination as claimed in claim 20, wherein the one or more additional therapeutic agent is an anti-tuberculosis agent.

* * * * *